United States Patent [19]
Chang et al.

[11] Patent Number: 6,093,550
[45] Date of Patent: Jul. 25, 2000

[54] UNIQUE ASSOCIATED KAPOSI'S SARCOMA VIRUS SEQUENCES AND USES THEREOF

[75] Inventors: Yuan Chang; Patrick S. Moore, both of New York, N.Y.

[73] Assignee: The Trustees of Columbia University in the City of New York, New York, N.Y.

[21] Appl. No.: 09/183,688

[22] Filed: Oct. 30, 1998

Related U.S. Application Data

[60] Division of application No. 08/343,101, Nov. 21, 1994, Pat. No. 5,830,759, which is a continuation-in-part of application No. 08/292,365, Aug. 18, 1994, abandoned.

[51] Int. Cl.[7] .............................. G01N 33/53; C12N 5/00; A61K 39/245; C07H 21/04
[52] U.S. Cl. .................... 435/7.1; 424/229.1; 424/230.1; 536/23.72; 435/325; 435/372.2; 435/235.1
[58] Field of Search .................. 435/7.1, 325, 372.2, 435/235.1; 424/229.1, 230.1; 536/23.72

[56] References Cited

PUBLICATIONS

Ioachim et al., Cytomegalovirus, Angiomatosis, and Kaposi's Sarcome: New Observations of a Debated Relationship, Modern Pathology, vol. 5, No. 2, 169–178, see Abstract and pp. 170 and 173, 1992.

*Primary Examiner*—Hankyel Park
*Attorney, Agent, or Firm*—John P. White; Cooper & Dunham LLP

[57] ABSTRACT

This invention provides an isolated DNA molecule which is at least 30 nucleotides in length and which uniquely defines a herpesvirus associated with Kaposi's sarcoma. This invention provides an isolated herpesvirus associated with Kaposi's sarcoma. This invention provides an isolated peptide encoded by the isolated DNA molecule. Further, this invention provides an isolated DNA virus wherein the viral DNA is about 270 kb in size; wherein the DNA encodes a thymidine kinase; and wherein the viral DNA is capable of selectively hybridizing to a nucleic acid probe selected from the group consisting of SEQ. ID NOs: 10–12. This invention provides an antibody specific to the peptide. Antisense and triplex oligonucleotide molecules are also provided. This invention provides a transgenic nonhuman mammal and a cell line containing at least a portion of the isolated DNA molecule. This invention provides a method of vaccinating a subject for KS, prophylaxis diagnosing or treating a subject with KS and detecting expression of a DNA virus associated with Kaposi's sarcoma in a cell.

24 Claims, 28 Drawing Sheets

FIG. 3A-1

SEQ. ID. NO. 1

| | | | | | |
|---|---|---|---|---|---|
| GAGCGCTGCC | ATGGAGGCGA | CCTTGGAGCA | ACGACCTTTC | CCGTACCTCG | CCACGGAGGC | 60
| CAACCTCCTA | ACGCAGATTA | AGGAGTCGGC | TGCCGACGGA | CTCTTCAAGA | GCTTTCAGCT | 120
| ATTGCTCGGC | AAGGACGCCA | GAGAAGGCAG | TGTCCGTTTC | GAAGCGCTAC | TGGGCGTATA | 180
| TACCAATGTG | GTGGAGTTTG | TTAAGTTTCT | GGAGACCGCC | CTCGCCGCCG | CTTGCGTCAA | 240
| TACCGAGTTC | AAGGACCTGC | GGAGAATGAT | AGATGGAAAA | ATACAGTTTA | AATTTCAAT | 300
| GCCCACTATT | GCCCACGGAG | ACGGGAGGAG | GCCCAACAAG | CAGAGACAGT | ATATCGTCAT | 360
| GAAGGCTTGC | AATAAGCACC | ACATCGGTGC | GGAGATTGAG | CTTGCGGCCG | CAGACATCGA | 420
| GCTTCTCTTC | GCCGAGAAAG | AGACGCCCTT | GGACTTCACA | GAGTACGCGG | GTGCCATCAA | 480
| GACGATTACG | TCGGCTTTGC | AGTTTGGTAT | GGACGCCCTA | GAACGGGGGC | TAGTGGACAC | 540
| GGTTCTCGCA | GTTAAACTTC | GGCACGCTCC | ACCCGTCTTT | ATTTTAAAGA | CGCTGGGGCA | 600
| TCCCGTCTAC | TCTGAGAGGG | GCCTCAAAAA | GTGCGTCAAG | TCTGACATGG | TATCCATGTT | 660
| CAAGGCACAC | CTCATAAACA | TTCATTTTTT | TCTAGATAAG | GCCGAGCTCA | TGACAAGGGG | 720
| GAAGCAGTAT | GTCCTAACCA | TGCTCTCCGA | CATGCTGGCC | GCGGTGTGCG | AGGATACCGT | 780
| CTTTAAGGGT | GTCAGCACGT | ACACCACGGC | CTCTGGGCAG | CAGGTGGCCG | GCGTCCTGGA | 840
| GACGACGGAC | AGCGTCATGA | GACGGCTGAT | GAACCTGCTG | GGGCAAGTGG | AAAGTGCCAT | 900
| GTCCGGGCCC | GCGGCCTACG | CCAGCTACGT | TGTCAGGGGT | GCCAACCTCG | TCACCGCCGT | 960
| TAGCTACGGA | AGGGCGATGA | GAAACTTTGA | ACAGTTTATG | GCACGCATAG | TGGACCATCC | 1020
| AACGTCTGCG | TCTGTGGAAG | GTGACAAGGC | CGCTCTCCGG | AGACACGACG | AGATTCAGAG | 1080
| AACCCGCATC | GCCGCCTCTC | TCGTCAAGAT | AGGGGATAAG | TTTGTGGCCA | TTGAAAGTTT | 1140
| GCAGCGCATG | TACAACGAGA | CTCAGTTTCC | CTGCCCACTG | AACCGGCGCA | TCCAGTACAC | 1200
| CTATTTCTTC | CCTGTTGGCC | TTCACCTTCC | CGTGCCCCGC | TACTCGACAT | CCGTCTCAGT | 1260
| CAGGGGCGTA | GAATCCCCGG | CCATCCAGTC | GACCGAGACG | TGGGTGGTTA | ATAAAAACAA | 1320
| CGTGCCTCTT | TGCTTCGGTT | ACCAAAACGC | CCTCAAAAGC | ATATGCCACC | CTCGAATGCA | 1380
| CAACCCCACC | AGTCAGCCGC | CGGCACAAAA | CCAAGCTTTT | CCCGATCCCG | ACGGGGACA | 1440
| TGGGTACGGT | CTCAGGTATG | AGCAGACGCC | AAACATGAAC | CTATTCAGAA | CGTTCCACCA | 1500
| GTATTACATG | GGGAAAAACG | TGGCATTTGT | TCCCGATGTG | GCCCAAAAAG | CGCTCGTAAC | 1560
| CACGGAGGAT | CTACTGCACC | CAACCTCTCA | CCGTCTCCTC | AGATTGGAGG | TCCACCCCTT | 1620
| CTTTGATTTT | TTTGTGCACC | CCTGTCCTGG | AGCGAGAGGA | TCGTACCGCG | CCACCCACAG | 1680
| AACAATGGTT | GGAAATATAC | CACAACCGGT | CGCTCCAAGG | GAGTTTCAGG | AAAGTAGAGG | 1740
| GGCGCAGTTC | GACGCTGTGA | CGAATATGAC | ACACGTCATA | GACCAGCTAA | CTATTGACGT | 1800
| CATACAGGAG | ACGGCATTTG | ACCCCGCGTA | TCCCCTGTTC | TGCTATGTAA | TCGAAGCAAT | 1860
| GATTCACGGA | CAGGAAGAAA | AATTCGTGAT | GAACATGCCC | CTCATTGCCC | TGGTCATTCA | 1920
| AACCTACTGG | GTCAACTCGG | GAAAACTGGC | GTTTGTGAAC | AGTTATCACA | TGGTTAGATT | 1980
| CATCTGTACG | CATATGGGGA | TTGGAAGCAT | CCCTAAGGAG | GCGCACGGCC | ACTACCGGAA | 2040
| AATCTTAGGC | GAGCTCATCG | GCCTTGAGCA | GGCGCTTCTC | AAGCTCGCGG | GACACGAGAC | 2100

FIG. 3A-2

```
GGTGGGTCGG ACGCCGATCA CACATCTGGT TTCGGCTCTC CTCGACCCGC ATCTGCTGCC 2160
TCCCTTTGCC TACCACGATG TCTTTACGGA TCTTATGCAG AAGTCATCCA GACAACCCAT 2220
AATCAAGATC GGGGATCAAA ACTACGACAA CCCTCAAAAT AGGGCGACAT TCATCAACCT 2280
CAGGGGTCGC ATGGAGGACC TAGTCAATAA CCTTGTTAAC ATTTACCAGA CAAGGGTCAA 2340
TGAGGACCAT GACGAGAGAC ACGTCCTGGA CGTGGCGCCC CTGGACGAGA ATGACTACAA 2400
CCCGGTCCTC GAGAAGCTAT TCTACTATGT TTTAATGCCG GTGTGCAGTA ACGGCCACAT 2460
GTGCGGTATG GGGGTCGACT ATCAAAACGT GGCCCTGACG CTGACTTACA ACGGCCCCGT 2520
CTTTGCGGAC GTCGTGAACG CACAGGATGA TATTCTACTG CACCTGGAGA ACGGAACCTT 2580
GAAGGACATT CTGCAGGCAG GCGACATACG CCGACGGTGG ACATGATCAG GGTGCTGTGC 2640
ACCTCGTTTC TGACGTGCCC TTTCGTCACC CAGGCCGCTC GCGTGATCAC AAAGCGGGAC 2700
CCGGCCCAGA GTTTTGCCAC GCACGAATAC GGGAAGGATG TGGCGCAGAC CGTGCTTGTT 2760
AATGGCTTTG GTGCGTTCGC GGTGGCGGAC CGCTCTGCCG AGGCGGCGGA GACTATGTTT 2820
TATCCGGTAC CCTTTAACAA GCTCTACGCT GACCCGTTGG TGGCTGACAC ACTGCATCCG 2880
CTCCTGCCAA ACTATGTCAC CAGGCTCCCC AACCAGAGAA ACGCGGTGGT CTTTAACGTG 2940
CCATCCAATC TCATGGCAGA ATATGAGGAA TGGCACAAGT CGCCCGTCGC GGCGTATGCC 3000
GCGTCTTGTC AGGCCACCCC GGGCGCCATT AGCGCCATGG TGAGCATGCA CCAAAAACTA 3060
TCTGCCCCCA GTTTCATTTG CCAGGCAAAA CACCGCATGC ACCCTGGTTT TGCCATGACA 3120
GTCGTCAGGA CGGACGAGGT TCTAGCAGAG CACATCCTAT ACTGCTCCAG GGCGTCGACA 3180
TCCATGTTTG TGGGCTTGCC TTCGGTGGTA CGGCGCGAGG TACGTTCGGA CGCGGTGACT 3240
TTTGAAATTA CCCACGAGAT CGCTTCCCTG CACACCGCAC TTGGCTACTC ATCAGTCATC 3300
GCCCCGGCCC ACGTGGCCGC CATAACTACA GACATGGGAG TACATTGTCA GGACCTCTTT 3360
ATGATTTTCC CAGGGGACGC GTATCAGGAC CGCCAGCTGC ATGACTATAT CAAAATGAAA 3420
GCGGGCGTGC AAACCGGCTC ACCGGGAAAC AGAATGGATC ACGTGGGATA CACTGCTGGG 3480
GTTCCTCGCT GCGAGAACCT GCCCGGTTTG AGTCATGGTC AGCTGGCAAC CTGCAGATA 3540
ATTCCCACGC CGGTCACATC TGACGTTGCC TATTTCCAGA CCCCCAGCAA CCCCCGGGGG 3600
CGTGCGGCGT CGGTCGTGTC GTGTGATGCT TACAGTAACG AAAGCGCAGA GCGTTTGTTC 3660
TACGACCATT CAATACCAGA CCCCGCGTAC GAATGCCGGT CCACCAACAA CCCGTGGGCT 3720
TCGCAGCGTG GCTCCCTCGG CGACGTGCTA TACAATATCA CCTTTCGCCA GACTGCGCTG 3780
CCGGGCATGT ACAGTCCTTG TCGGCAGTTC TTCCACAAGG AAGACATTAT GCGGTACAAT 3840
AGGGGGTTGT ACACTTTGGT TAATGAGTAT TCTGCCAGGC TTGCTGGGGC CCCCGCCACC 3900
AGCACTACAG ACCTCCAGTA CGTCGTGGTC AACGGTACAG ACGTGTTTTT GGACCAGCCT 3960
TGCCATATGC TGCAGGAGGC CTATCCCACG CTCGCCGCCA GCCACAGAGT TATGCTTGCC 4020
GAGTACATGT CAAACAAGCA GACACACGCC CCAGTACACA TGGGCCAGTA TCTCATTGAA 4080
GAGGTGGCGC CGATGAAGAG ACTATTAAAG CTCGGAAACA AGGTGGTGTA TTAGCTAACC 4140
CTTCTAGCGT TGGCTAGTCA TGGCACTCGA CAAGAGTATA GTGGTTAACT TCACCTCCAG 4200
```

FIG. 3A-3

```
ACTCTTCGCT GATGAACTGG CCGCCCTTCA GTCAAAAATA GGGAGCGTAC TGCCGCTCGG 4260
AGATTGCCAC CGTTTACAAA ATATACAGGC ATTGGGCCTG GGGTGCGTAT GCTCACGTGA 4320
GACATCTCCG GACTACATCC AAATTATGCA GTATCTATCC AAGTGCACAC TCGCTGTCCT 4380
GGAGGAGGTT CGCCCGGACA GCCTGCGCCT AACGCGGATG GATCCCTCTG ACAACCTTCA 4440
GATAAAAAAC GTATATGCCC CCTTTTTTCA GTGGGACAGC AACACCCAGC TAGCAGTGCT 4500
ACCCCCATTT TTTAGCCGAA AGGATTCCAC CATTGTGCTC GAATCCAACG GATTTGACCC 4560
CGTGTTCCCC ATGGTCGTGC CGCAGCAACT GGGGCACGCT ATTCTGCAGC AGCTGTTGGT 4620
GTACCACATC TACTCCAAAA TATCGGCCGG GGCCCCGGAT GATGTAAATA TGGCGGAACT 4680
TGATCTATAT ACCACCAATG TGTCATTTAT GGGGCGCACA TATCGTCTGG ACGTAGACAA 4740
CACGGATCCA CGTACTGCCC TGCGAGTGCT TGACGATCTG TCCATGTACC TTTGTATCCT 4800
ATCAGCCTTG GTTCCCAGGG GGTGTCTCCG TCTGCTCACG GCGCTCGTGC GGCACGACAG 4860
GCATCCTCTG ACAGAGGTGT TTGAGGGGGT GGTGCCAGAT GAGGTGACCA GGATAGATCT 4920
CGACCAGTTG AGCGTCCCAG ATGACATCAC CAGGATGCGC GTCATGTTCT CCTATCTTCA 4980
GAGTCTCAGT TCTATATTTA ATCTTGGCCC CAGACTGCAC GTGTATGCCT ACTCGGCAGA 5040
GACTTTGGCG GCCTCCTGTT GGTATTCCCC ACGCTAACGA TTTGAAGCGG GGGGGGTATG 5100
GCGTCATCTG ATATTCTGTC GGTTGCAAGG ACGGATGACG GCTCCGTCTG TGAAGTCTCC 5160
CTGCGTGGAG GTAGGAAAAA AACTACCGTC TACCTGCCGG ACACTGAACC CTGGGTGGTA 5220
GAGACCGACG CCATCAAAGA CGCCTTCCTC AGCGACGGGA TCGTGATATG GCTCGAAAGC 5280
TTCATCGTGG TGCCCTGCCC TCAAATTCTC ACAACGGCTT GAGGATGGTG CTTTTTTGTT 5340
ATTGTTACTT GCAAAATTGT GTGTACCTAG CCCTGTTTCT GTGCCCCCTT AATCCTTACT 5400
TGGTAACTCC CTCAAGCATT GAGTTTGCCG AGCCCGTTGT GGCACCTGAG GTGCTCTTCC 5460
CACACCCGGC TGAGATGTCT CGCGGTTGCG ATGACGCGAT TTTCTGTAAA CTGCCCTATA 5520
CCGTGCCTAT AATCAACACC ACGTTTGGAC GCATTTACCC GAACTCTACA CGCGAGCCGG 5580
ACGGCAGGCC TACGGATTAC TCCATGGCCC TTAGAAGGGC TTTTGCAGTT ATGGTTAACA 5640
CGTCATGTGC AGGAGTGACA TTGTGCCGCG GAGAAACTCA GACCGCATCC CGTAACCACA 5700
CTGAGTGGGA AAATCTGCTG GCTATGTTTT CTGTGATTAT CTATGCCTTA GATCACAACT 5760
GTCACCCGGA AGCACTGTCT ATCGCGAGCG GCATCTTTGA CGAGCGTGAC TATGGATTAT 5820
TCATCTCTCA GCCCCGGAGC GTGCCCTCGC CTACCCCTTG CGACGTGTCG TGGGAAGATA 5880
TCTACAACGG GACTTACCTA GCTCGGCCTG GAAACTGTGA CCCCTGGCCC AATCTATCCA 5940
CCCCTCCCTT GATTCTAAAT TTTAAATAAA GGTGTGTCAC TGGTTACACC ACGATTAAAA 6000
ACCACTCACT GAGATGTCTT TTTAACCGCT AAGGGATTAT ACCGGGATTT AAAACCGCCC 6060
ACTGATTTTT TTACGCTAAG AGTTGGGTGC TTGGGGGGTT TTGCATTGCT CTGTTGTAAA 6120
CTATATATAA GTTAAACCAA AATTCGCAGG GAGACAAGGT GACGGTGGTG AGAACTCAGT 6180
TGAGAGTCAG AGAATACAGT GCTAATCAGG GTAGATGAGC ATGACTTTCC CCGTCTCCAG 6240
```

FIG. 3A-4

```
TCACCGGAGG AATGGTGGAC GGCTCCGTCC TGGTGCGAAT GGCCACCAAG CCTCCCGTGA 6300
TTGGTCTTAT AACAGTGCTC TTCCTCCTAG TCATAGGCGC CTGCGTCTAC TGCTGCATTC 6360
GCGTGTTCCT GGCGGCTCGA CTGTGGCGCG CCACCCCACT AGGCAGGGCC ACCGTGGCGT 6420
ATCAGGTCCT TCGCACCCTG GGACCGCAGG CCGGGTCACA TGCACCGCCG ACGGTGGGCA 6480
TAGCTACCCA GGAGCCCTAC CGTACAATAT ACATGCCAGA TTAGAACGGG GTGTGTGCTA 6540
TAATGGATGG CTATGGGGGG GGGCTGTAGA TAATTGAGCG CTGTGCTTTT ATTGTGGGGA 6600
TATGGGCTTG TACATGTGTC TATCATCGGT AGCCATAAAA TGGGCCATGA CAACTGCCAC 6660
AAGTAAGTCG TCCGACATGT GCTTTTGCTT GGCGCTGTAT GACTGCCCTC CATCCCTAAG 6720
CGGGACGCAC TTGATCGCGC GGACCTGTTC TACCAGGTAG GTCACCGGGT CAAATGATAT 6780
TTTGATGGTG TTGGACACCA CCGTCTGGCT GGCGCTCAGG GTGCCGGAGT TCAGAGCGTA 6840
GATGAATGTC TCAAACGCGG AGGATTTCTC GCCTCCCAAC ATGTAAATTG GCCACTGCAG 6900
GGCGCTGCTC TTGTCAGTAT AGTGTAGAAA ATGTATGGGG AGCGGGCATA TTTCGTTAAG 6960
GACGGTTGCA ATGGCCACCC CAGAATCTTG GCTGCTGTTG CCTTCGAACG CGGTTCACGC 7020
GCTCAATTGT GGGGTGGAGC ACAGCGATCG CCTTAATCAT CGTGCATCGG CAGGACGCTA 7080
TCTCGTAAGC AGCTGGCCCA GTGAGGTCGC GCAGGAAGAA ATGCTCCATG CCCAATATGA 7140
GGCTTCTGGT GGGAGTCTGA GTACTCGTGA CAACGGCGCC CACCATGTAC CGGACGCCTC 7200
CGTGTTGTTC GTATACGCGG GGTCGATGTA AACAAACAGC TGTTTTCCAA GGCACTTCTG 7260
AACCTGCTGG GCGGTGTGTC TACCCGACAC ATGTCAAACT GTGTCAGCGC TGCGTCACCC 7320
ACCACGCGGT AAAGCGTACG ATTTGACGAC GCTGCTCCCT CGCCCATTAG TTCGGTGTCG 7380
AATGCCCCCT CCATAAAGAG GTTGGTGGTG GTTTTGATGG ATTCGTCGAT GGTGATGTAC 7440
GTCGGAATGT GCAGTCTGTA ACAAGGACAG GACACTAGTG CGTCTTGCAG GTGGAAATCT 7500
TCTCGGTGGT CCGCACACAC GTAACTGACC ACATTCAGCA TCTTTTCCTG GGCGTTCCTG 7560
AGGTTAAGCA GGAAACTCGT GGAGCGGTCT GACGAGTTCA CGGATGATAT AAATATAAGC 7620
TTGGCGTCTT TCTGAAGCAT GAAACCCAGA ATAGCCGGCA GTGCATCCTT TTTAATAAAA 7680
TTCGCCTCGT CTACGTAGAG CAGGTTAAAG GTCTGTCCCC GAATGCTCTG CAGACACGGA 7740
AAGACACAAA AGAGGGCTC ATAAGCGGCT AACAGTAAAG GAGAGGAGGC GAACAGTGCG 7800
TGGCTCTTGG TTCTTGGGAA TAAAAGGGGG CGTGTGTGCC GATCGATCGT ATGGGTGAGC 7860
CAGTGGATCC TGGACATGTG GTGAATGAGA AAGATTTTGA GGAGTGTGAA CAATTTTTCA 7920
GTCAACCCCT TAGGGAGCAA GTGGTCGCGG GGGTCAGGGC ACTCGACGGC CTCGGTCTCG 7980
CTGACTCTCT ATGTCACAAA ACAGAAAGAC TCTGCCTGCT GATGGACCTG GTGGGCACGG 8040
AGTGCTTTGC GAGGGTGTGC CGCCTAGACA CCGGTGCGAA ATGAAGAGTG TGGCGAGTCC 8100
CTTATGTCAG TTCCACGGCG TGTTTTGCCT GTACCAGTGT CGCCAGTGCC TGGCATACCA 8160
CGTGTGTGAT GGGGGCGCCG AATGCGTTCT CCTGCATACG CCGGAGAGCG TCATCTGCGA 8220
ACTAACGGGT AACTGCATGC TCGGCAACAT TCAAGAGGGC CAGTTTTTAG GGCCGGTACC 8280
```

FIG. 3A-5

```
GTATCGGACT TTGGATAACC AGGTTGACAG GGACGCATAT CACGGGATGC TAGCGTGTCT 8340
GAAACGGGAC ATTGTGCGGT ATTTGCAGAC ATGGCCGGAC ACCACCGTAA TCGTGCAGGA 8400
AATAGCCCTG GGGGACGGCG TCACCGACAC CATCTCGGCC ATTATAGATG AAACATTCGG 8460
TGAGTGTCTT CCCGTACTGG GGGAGGCCCA AGGCGGGTAC GCCCTGGTCT GTAGCATGTA 8520
TCTGCACGTT ATCGTCTCCA TCTATTCGAC AAAAACGGTG TACAACAGTA TGCTATTTAA 8580
ATGCACAAAG AATAAAAAGT ACGACTGCAT TGCCAAGCGG GTGCGGACAA AATGGATGCG 8640
CATGCTATCA ACGAAGATA CGTAGGTCCT CGCTGCCACC GTTTGGCCCA CGTGGTGCTG 8700
CCTAGGACCT TTCTGCTGCA TCACGCCATA CCCCTGGAGC CCGAGATCAT CTTTTCCACC 8760
TACACCCGGT TCAGCCGGTC GCCAGGGTCA TCCCGCCGGT TGGTGGTGTG TGGGAAACGT 8820
GTCCTGCCAG GGGAGGAAAA CCAACTTGCG TCTTCACCTT CTGGTTTGGC GCTTAGCCTG 8880
CCTCTGTTTT CCCACGATGG GAACTTTCAT CCATTTGACA TCTCGGTACT GCGCATTTCC 8940
TGCCCTGGTT CTAATCTTAG TCTTACTGTC AGATTTCTCT ATCTATCTCT GGTGGTGGCT 9000
ATGGGGGCGG GACGGAATAA TGCGCGGAGT CCGACCGTTG ACGGGGTATC GCCGCCAGAG 9060
GGCGCCGTAG CCCACCCTTT GGAGGAACTG CAGAGGCTGG CGCGTGCTAC GCCGGACCCG 9120
GCACTCACCC GTGGACCGTT GCAGGTCCTG ACCGGCCTTC TCCGCGCAGG GTCAGACGGA 9180
GACCGCGCCA CTCACCACAT GGCGCTCGAG GCTCCGGGAA CCGTGCGTGG AGAAAGCCTA 9240
GACCCGNCTG TTTCACAGAA GGGGGCAGCG CGCACACGCC ACAGGCCACC CCCCGTGCGA 9300
CTGAGCTTCA ACCCCGTCAA TGNCGATGTA CCCGCTACCT GGNGAGACGC CACTAACGTG 9360
TACTCGGGTG CTCCCTACTA TGTGTGTGTT TACGAACGCG GTGG              9404
```

FIG. 3B

SEQ. ID. NO. 2

```
GGATCCCTCT GACAACCTTC AGATAAAAAA CGTATATGCC CCCTTTTTTC AGTGGGACAG    60

CAACACCCAG CTAGCAGTGC TACCCCCATT TTTTAGCCGA AAGGATTCCA CCATTGTGCT   120

CGAATCCAAC GGATTTGACC CCGTGTTCCC CATGGTCGTG CCGCAGCAAC TGGGGCACGC   180

TATTCTGCAG CAGCTGTTGG TGTACCACAT CTACTCCAAA ATATCGGCCG GGGCCCCGGA   240

TGATGTAAAT ATGGCGGAAC TTGATCTATA TACCACCAAT GTGTCATTTA TGGGGCGCAC   300

ATATCGTCTG GACGTAGACA ACACGGATCC                                    330
```

FIG. 3C

SEQ. ID. NO. 3

```
GGATCCGCTG GCAGGTGGGC GCGCACCCTCG TCGGGTAGCT TGGAGACAAA CAGCTCCAGG    60
CCAGTCCGCG CCGTAGCGCC TGCAGGTGCC TCACCACCGG GCCCGGGTCA TGCGATCTGT   120
TTAGTCCGGA GAAGATAGGG CCCTTGGGAA GCCGCTGAAC CAGCTCCAGG GTCTCCAAGA   180
TGCGCACCGG TTGTCGGAGC TGTCGCGATA GAGGTTAGGG TAGGTGTCCG GTCCGTCCGT   240
GGGCTCAAAC CTGCCCAGAC ACACCACTGT CTGCTGGGGG ATCATCCTTC TCAGGGAGAT   300
GCATTCTTTG GAAGTAGTGG TAGAGATGGA GCAGACTGCC AGGGCGTTGC AGGAGTGGTG   360
GCGATGGTGC GCACCGTTTT TAAGAAACCC CCCAGGGGTGG GGACTCCCGC TCCCTGCAGC   420
ATCTCGGCCT GCTGTACGTC CTTGGCGAAT ATGCGACGAA ATCGGCTGTG CGCACGGGGT   480
CCCAGGGCCG GTCCGGTGGC ATACAGGCCG GTGAGGGCCC CCTGGGTCTG TCCGCCTGGA   540
AACAGGGTGC TGTGAAACAA CAGGTTGCAA GGCCGGCGAAT ACCCCTCTGC ACGCTGCTGT   600
GGACGTGGGT GTATGCTCCG TGGATCC                                      627
```

FIG. 3D

SEQ. ID. NO. 4

```
CCGCAGCTCT AATACGACTC ACTATAGGGC GTCGACTCGA TCAAATAGCG ATACAGCTGC    60
CCTCCTGTTG ATGTTGGCCT CCAGAGCCGA CTTAATAAAC TCTCTTTTAG AGTTGGTTGA   120
GTCCATTCTC CTTGATCATG GTGATGATCG CCGGTATGTC ATACGATGGG ATGATTAGAT   180
AGTCGCCCGT AGTTGGACAC CTTTGGGTCT GAACATTGCC TGTTATATAC TGGGTCCCTT   240
TTCCACTCAA CAGTAGGATT CCACCCACGT GGTCCCCTGA CCGCAATTAT GCTATTTTGC   300
TGATATATGT GACACAAGAG GCAGGTGTGG GAAATGTAAG TGTCGGAAGC ATCTATGATT   360
TTCATCTGAC TCACTACCCT TTGTATCCGA GAAGTAGCGA ATGGCGGGCG GCAAGCGCCA   420
TGTCCCGGAA AAATCTCCGT ATAGAAACTT GGTGTACTTC AGGGCATGAT TAACGAACGA   480
CAAAAGATCC CGTTTGGAGC GTACATGTGA CCTGGAAGTA GCACCGGGCC CGGGTAACCG   540
CAGTGCTGTT TGTACAGGCA ACAGTCGGCC CGACAAAAAG AGGCGGGTCC GTTGAACAGC   600
AGCCATAGCA ACGGAAGGGG GTCGTCAGGA AGAAGACCCT TCCAAGTTCC GGGGTCACAC   660
AGGCCATCTA CAGCCTCCCG AAGGAGCGCA TCCTTATTCA GAGTCAAAGC CCACGTCCAC   720
TCCTCGGTAG TATAGTGGTT GTAGAACACC TGGCCCTTTT CGTGTGTTTC TACGTGAGAC   780
GGGTCCAGTG CGATTCCTC  ACCCGCCGCC CCGAAACCCT GCCCGAGGAC TCTCTGGAGC   840
TTCTCCAGTC TAGGCAAGTG GAGATTACTA AAGTCTGGCC GCAAGGCCGG CCGGCCACTG   900
CAGATTGGCT GGACCCTCGG TCATCACGTT GGAAACCAAG AGGAAGCTGT TCAGGGGAGT   960
TTCTATCANC TTAAATTGTC CAGGTGTGTT CTCGGTAAGG TCCAGGGCAA GTTGTNCGCC  1020
CTTGACGTAC CTACTGGTCA CCTCCGGGTC ACCCTCGGAC ACGAGCGAGC TCAAAGCAAA  1080
CATGCTGCTC AGCCGACACA GGGAGCGTCT TGCCGACAAC CTGGAGGAGA CCGACAAAGA  1140
CGGCGGAGAG AGGTGGGAAC TGAGTGCCCC GACATTCACG CGACACTGTC CCAAAACGGC  1200
ACGGATGGCG CACCCTTTTA TTGGNGTGGT GCACAGAATA AACTCATACA GTTCGGTCCT  1260
GGAAACATAC TGCACACGGG ACCATCCCGC CACGCCCACG TCAGCAAATC CCGACGTGGG  1320
AACCCCCAGA CCGTCCGAGG ACAACGTCCC CGCAAAGNCG CGCCTATTGG AGTCCCTATC  1380
AACATACTTG NAGATGCGGT GTGTGCGCGA GGACGCGCAC GTCTCCACGG NCGATCAACT  1440
GGTCGAGTAC CAGGCGGNCA GAAAAACACA CGACTCCCTG CACGCCTGCT CTGTCTACCG  1500
CGAAACTTCA GGCTTTTCTG GTTAACCTTT CGGTCCTTTC TGAACGGGTG TTACGTTC    1558
```

FIG. 3E
SEQ. ID. NO. 5

```
GCGGCCGCGA GCTCAATTAA CCCTCACTAA AGGGAGTCGA CTCGATCGAG TCGGAGAGTT    60
GGCACAGGCC TTGAGCTCGC TGTGACGTTC TCACGGTGTT GGTTGGGATC AGCTGGTGAC   120
TCAGACAAGT CTTGAGCTCT ACAACGTAAC ATACGGGCTG ATGCCCACCC GATACCAGAA   180
TTACGCAGTC GGCAATTCTG TGCCCTAGAG TCACCTCAAA GAATAATCTG TGGTGTCCAA   240
GGGGAGGGTT CTGGGGCCGG CTACTTAGAA ACCGCCATAG ATCGGGCAGG GTGGAGTACT   300
TGAGGAGCCG GCGGTAGGTG GCCAGGTGGG CCGGTTACCT GCTCTTTTGC GTGCTGCTGG   360
AAGCCTGCTC AGGGATTTCT TAACCTCGGC CTCGGTTGGA CGTACCATGG CAGAAGGCGG   420
TTTTGGAGCG GACTCGGTGG GGCGCGGCGG AGAAAAGGCC TCTGTGACTA GGGGAGGCAG   480
GTGGGACTTG GGGAGCTCGG ACGACGAATC AAGCACCTCC ACAACCAGCA CGGATATGGA   540
CGACCTCCCT GAGGAGAGGA AACCACTAAC GGGAAAGTCT GTAAAAACCT CGTACATATA   600
CGACGTGCCC ACCGTCCCGA CCAGCAAGCC GTGGCATTTA ATGCACGACA ACTCCCTCTA   660
CGCAACGCCT AGGTTTCCGC CCAGACCTCT CATACGGCAC CCTTCCGAAA AAGGCAGCAT   720
TTTTGCCAGT CGGTTGTCAG CGACTGACGA CGACTCGGGA GACTACGCGC CAATGGATCG   780
CTTCGCCTTC CAGAGCCCCA GGGTGTGTGG TCGCCCTCCC CTTCCGCCTC CAAATCACCC   840
ACCTCCGGCA ACTAGGCCGG CAGACGCGTC AATGGGGGAC GTGGGCTGGG CGGATCTGCA   900
GGGACTCAAG AGGACCCCAA AGGGATTTTT AAAAACATCT ACCAAGGGGG GCAGTCTCAA   960
AGCCCGTGGA CGCGATGTAG GTGACCGTCT CAGGGACGGC GGCTTTGCCT TTAGTCCTAG  1020
GGGCGTGAAA TCTGCCATAG GGCAAAACAT TAAATCATGG TTGGGATCG GAGAATCATC  1080
GGCGACTGCT GTCCCCGTCA CCACGCAGCT TATGGTACCG GTGCACCTCA TTAGAACGCC  1140
TGTGACCGTG GACTACAGGA ATGTTTATTT GCTTTACTTA GAGGGGGTAA TGGGTGTGGG  1200
CAAATCAACG CTGGTCAACG CCGTGTGCGG GATCTTGCCC CAGGAGAGAG TGACAAGTTT  1260
TCCCGAGCCC ATGGTGTACT GGACGAGGGC ATTTACAGAT TGTTACAAGG AAATTTCCCA  1320
CCTGATGAAG TCTGGTAAGG CGGGAGACCC GCTGACGTCT GCCAAAATAT ACTCATGCCA  1380
AAACAAGTTT TCGCTCCCCT TCCGGACGAA CGCCACCGCT ATCCTGCGAA TGATGCAGCC  1440
CTGGAACGTT GGGGGTGGGT CTGGGAGGGG CACTCACTGG TGCGTCTTTG ATAGGCATCT  1500
CCTCTCCCCA GCAGTGGTGT TCCCTCTCAT GCACCTGAAG CACGGCGCCT ATCTTTTGAT  1560
CACTTCTTTC AATTACTTTC CATCTTTAGA GCCACAGAAG GCGACGTGGT CGCCATTCTC  1620
ACCCTCTCCA GCGCCGAGTC GTTGCGGCGG GTCAGGGCGA GGGGAAGAAA GAACGACGGG  1680
ACGGTGGAGC AAAACTACAT CAGAGAATTG GCGTGGGCTT ATCACGCCGT GTACTGTTCA  1740
TGGATCATGT TGCAGTACAT CACTGTGGAG CAGATGGTAC AACTATGCGT ACAAACCACA  1800
AATATTCCGG AAATCTGCTT CCGCAGCGTG CGCCTGGCAC ACAAGGAGGA AACTTTGAAA  1860
AACCTTCACG AGCAGAGCAT GCTACCTATG ATACACCGGT GTACTGGATC CCGTGAGACA  1920
TCATCCCGTC GTGATCGAGC TTTGCTTTTG TTTCTTCACA GAGCTGAGAA AATTACAATT  1980
TATCGTAGCC GACGCGGATA AGTTCCACGA CGACGTATGC GGCCTGTGGA CCGAAATCTA  2040
CAGGCAGATC CTGTCCAATC CGGCTATTAA ACCCAGGGCC ATCAACTGGC CAGCATTAGA  2100
GAGCCAGTCT AAAGCAGTTA ATCACCTAGA GGAGACATGC AGGGTCTAGC CTTCTTGGCG  2160
GCCCTTGCAT GCTGGCGATG CATATCGTTG ACATGTGGAG CCACTGGCGC GTTGCCGACA  2220
ACGGCGACGA CAATAACCCG CTCCGCCACG CAGCTCATCA ATGGGAGAAC CAACCTCTCC  2280
ATAGAACTGG AATTCAACGG CACTAGTTTT TTTCTAAATT GGCAAAATCT GTTGAATGTG  2340
ATCACGGAGC CGGCCCTGAC AGAGTTGTGG ACCTCCGCCG AAGTCGCCGA GGACCTCAGG  2400
GTAACTCTGA AAAAGAGGCA AAGTCTTTTT TTCCCCAACA AGACAGTTGT GATCTCTGGA  2460
GACGGCCATC GCTATACGTG CGAGGTGCCG ACGTCGTCGC AAACTTATAA CATCACCAAG  2520
GGCTTTTACT ATAGCGCTCT GCCCGGGCAC CTTGGCGGAT TTGGGATCAA CGCGCGTCTG  2580
GTACTGGGTG ATATCTTCGC ATCAAAATGG TCGCTATTCG CGAGGGACAC CCCAGAGTAT  2640
CGGGCGTTTT ACCCAATGAA TGTCATGGCC GTCAAGTTTT CCATATCCAT TGGCAACAAC  2700
GAGTCCGGCG TAGCGCTCTA TGGAGTGGTG TCGGAAGATT TCGTGGTCGT CACGCTCCAC  2760
AACAGGTCCA AAGAGGCTAA CGAGACGGCG TCCCATCTTC TGTTCGGTCT CCCGGATTCA  2820
CTGCCATCTC TGAAGGGCCA TGCCACCTAT GATGAACTCT CGTTCGCCCG AAACGCAAAA  2880
TATGCGCTAG TGGCGATCCT GCCTAAAGAT TCTTACCAGA CACTCCTTAC AGAGAATTGC  2940
ACTCGCATAT TTCTGAACAT GACGGAGTCG ACG                                2973
```

FIG. 3F

SEQ. ID. NO. 6

```
GAGTCTCTAA TCCTGAAGTC CCGATGCCAC TGTTGTTCGA AAAGTTTGGG ACTCCGGACT    60
CGTCTACCCT GCCACTCTAC GCGGCTAGGC ACCCGGAACT ATCGTTGCTA CGGATCATGC   120
TCTCACCGCA CCCCTACGCG TTAAGAAGCC ACTTGTGCGT AGGCGAAGAG ACCGCATCTC   180
TTGGCGTTTA CCTGCACTCC AAGCCAGTCG TACGCGGCCA NGAATTCGAG GACACGCAGA   240
TACTACCGGA GTGCCGGCTG GCCATAACGA GCGACCAGTC TTATACCAAC TTTAAGATTA   300
TAGATCGCC AGCGGGATGC CGTCGCGTCC CCATACACGC CGCGAACAAG CGTGTCGTCA    360
TCGACGAGGC CGCCAACCGC ATAAAGGTGT TTGACCCAGA GTCGCCTTTA CCGCGTCACC   420
CCATAACACC CNNTGCCGGT CAGACCAGAT CTATACTGAA ACACAACATC GCACAGGTTT   480
GCGAACGGGA TATCGTGTCA CTTAACACAG ACAACGAGGC CGCGTCTATG TTCTACATGA   540
TTGGACTCAG GCGGCCGAGA CTCGGAGAAA GCCCGGTCTG TGACTTCAAC ACCGTTACCA   600
TCATGGAGCG TGCTAACAAC TCGATAACTT TTCTACCCAA GCTAAAACTG AACCGGCTAC   660
AACACCTGTT CCTGAAGCAC GTGTTNNTGC GCAGCATGGG GCTGGAAAAC ATCGTGTCGT   720
GTTTCTCATC GCTGTACGGC GCAGAACTTG CCCCTGCGAA AACACACGAG CGGGAGTTCT   780
TCGGCGCTCT GCTAGAAAGA CTCAAACGTC GGGTGGAGGA CGCGGTCTTC TGCCTGAATA   840
CCATAGAGGA TTTCCCGTTT AGGGAACCCA TTCGCCAACC CCCAGATTGT TCCAAGGTGC   900
TTATAGAAGC CATGGAAAAG TACTTTATGA TGTGTAGCCC CAAAGACCGT CAAAGCGCCG   960
CATGGCTAGG TGCAGGGGTG GTCGAACTGA TATGTGACGG CAATCCACTT TCTGAGGTGC  1020
TCGGATTTCT TGCCAAGTAT ATGCCCATAC AAAAAGAATG CACAGGAAAC CTTTTAAAAA  1080
TCTACGCTTT ATTGACCGTC TAATAAAGGA TGGAAAACAG TCTGTAAAGA AAGTAGATAA  1140
CCCCCGAGAA CCCAATAAAA GAGAGAATTA GAAACAAAGC ACTGNNTGCG CGTCTTCTAT  1200
ACATGCCCCT TATCTCCACT ACGGTCCCGT TGTCCCTCAG CCACAAATAA TGAATGTGTA  1260
GGTTGTTATT ATCAAAGAAA CATGAGAGAC CTAAAAAGAG GTTGGTCTGC ACCCTTTCAT  1320
TAGTGACATA CATGAGAGAC TGCAGGCCAT CGCTCTCGTC GTAGCTCATG ATTACAGAGT  1380
CACAAAGGGG GCAACCTCTT CTTGGTGTGC                                  1410
```

FIG. 3G

SEQ. ID. NO. 7

```
CTCTTTTGGG AAAAGCGGGT CGACGGTACA GCGGCGAAGG TTTAATAATT GACGGTGGCG   60
GAGTGTTTAC GCGCGGACAG ATAGACACCG ACAACTACCT ACCTGCGGTG GGATCATGGG  120
AACTTACCGA TGATTGTGAT AAACCCTGCG AATTCAGGGA GCTACGCTCG CTGTATCTTC  180
CCGCGCTACT AACGTGCACC ATATGTTACA AAGCCATGTT CAGGATAGTG TGCAGGTACC  240
TGGAGTTCTG GGAGTTCGAA CAGTGTTTTC ATGCGTTTCT GGCGGTGTTG CCCCATAGTC  300
TACAACCCAC AATCTATCAA AATTATTTTG CACTCCTGGA GAGCCTGAAG CATCTCTCGT  360
TTTCAATAAT GCCACCCGCA TCCCCAGACG CACAGCTACA TTTTTTAAAG TTTAACATCA  420
GCAGCTTCAT GGCCACGTGG GGGTGGCACG GAGAGCTGGT CTCNNTGCGC CGTGCCATCG  480
CTCACAACGT AGAGCGACTG CCCACCGTGC TGAAGAACGC TTATCGATA             529
```

FIG. 3H

SEQ. ID. NO. 8

```
AAAGTTTAAC ATCAGCAGCT TCATGGCCAC GTGGGGGTGG CACGGAGAGC TGGTCTNNCT     60
GCGCCGTGCC ATCGCTCACA ACGCAGAGCG ACTGCCCACC GTGCTGAAGA ACCTGTCGAA    120
ACAGAGTAAG CACCAGGACG TCAAGGTTAA CGGACGGGAT CTGGTGGGCT TTCAGCTGGC    180
TCTAAACCAG CTCGTGTCCC GTCTGCACGT AAAAATCCAA CGCAAGGACC CCGGACCAAA    240
GCCATACAGG GTGGTCGTCA GTACCCCAGA TTGTACCTAC TATCTAGTGT ATCCGGGCAC    300
ACCGGCCATC TACAGACTCG TCATGTGTAT GCAGTGGCA GACTGCATCG GCCACTCGTG    360
CAGCGGACTG CACCCCTGCG CAAACTTTTT AGGCACCCAC GAGACACCGC GTCTCCTGCC    420
GGCGACGCTT TCAAGAATCC GGTACGCGCC GAAAGACCGG CGAGCAGCCA TGAAAGGAAA    480
TTTGCAGGCG TGCTTCCAAC GATACGCGGC CACGGACGCG CGGACTCTGG GCAGCTCTAC    540
AGTGTCAGAC ATGCTGGAAC CCACAAAACA CGTCAGTTTG GAAAACTTCA AGATACCAT    600
ATTCAACACC AACATGGTGA TTAACACTAA GATAAGCTGC CACGTTCCTA ACACCCTGCA    660
AAAGACTATT TTAAACATCC CCAGATTGAC CAACAATTTT GTTATACGAA AGTACTCCGT    720
AAAGGAACCT TCTTTTACCA TAAGCGTGTT TTTTTCCGAC CACTTTCTC AACATGTGTC    780
AATAAACATC AACATCAGTG GGGACATGCT GCACTTTCTC TTCGCAATGG GTACGCTGAA    840
ATGCTTTCTG CCAATCAGGC ACATATTTCC TGTATCGATA GCAAATTGGA ACTCCACGTT    900
GGACCTGCAC GGACTGGAAA ACCAGTACAT GGTGAGAATG GGGCGAAAAA ACGTATTTTG    960
GACCACAAAC TTTCCATCTG TGGTCTCCAG CAAGGATGGG CTAAACGTGT CCTGGTTTAA   1020
GGCCGCGACA GCCACGATTT CGGGCAGCCT CTTGTGGAAC AGATTCGCCA AAAATAGAAT   1080
CGANNTGGCG CCCATTCTCA CGGACCAGCA CGCGCGCATC GACGGAAACA AAAGGTTCCT   1200
ATTCTCCCTA CTTGAGCACA GAAACCGTTC CCAAATACAG ACGCTACACA AAAGGTTCCT   1200
GGAGTGTCTG GTGGAATGCT GTTCGTTTCT CAGGCTTGAC GTGGCTTGCA TTAGGCGAGC   1260
CGCCGCCCGG GGCCTGTTTG ACTTCTCAAA GAAGATAATC AGTCACACTA AAAGC        1315
```

FIG. 31

SEQ. ID. NO. 9

```
GCAATGCAAA CTTCATTTCG TTCGTCGCCA CCACGGGTCA TCGGTTCGCC GCTCTAAAGC      60
CACAAATTGT CCGTCACGCC ATTCGCAAAC TAGGCCTGCA CTGGCGCCAC CGAACGGCCG     120
CGTCCAACGA GCAGACACCG CCAGCCGATC CCCGCGTACG TTGCGTCCGT CCGCTGGTCT     180
AAGCTATGTT ACGAGTTCCG GACGTGAAGG CTAGTCTAGT AGAGNNGCGG CGCGCCTGTC     240
GACAGGCGAG CGCGTGTTTC ACGTCTTGAC CTCTCCGGCG GTGGCCGRCCA TGGTGGGAG    299
```

FIG. 3J

SEQ. ID. NO. 10

```
AGCCGAAAGG ATTCCACCAT TGTGCTCGAA TCCAACGGAT TTGACCCCGT GTTCCCATG    60
GTCGTGCCGC AGCAACTGGG GCACGCTATT CTGCAGCAGC TGTTGGTGTA CCACATCTAC  120
TCCAAAATAT CGGCCGGGGC CCCGGATGAT GTAAATATGG CGGAACTTGA TCTATATACC  180
ACCAATGTGT CATTTATGGG GCGCACATAT CGTCTGGACG TAGACAACAC GGA         233
```

FIG. 3K

SEQ. ID. NO. 11

| | | | | | |
|---|---|---|---|---|---|
|GAAATTACCC|ACGAGATCGC|TTCCCTGCAC|ACCGCACTTG|GCTACTCATC|AGTCATCGCC| 60
|CCGGCCCACG|TGGCCGCCAT|AACTACAGAC|ATGGGAGTAC|ATTGTCAGGA|CCTCTTTATG| 120
|ATTTTCCCAG|GGGACGCGTA|TCAGGACCGC|CAGCTGCATG|ACTATATCAA|AATGAAAGCG| 180
|GGCGTGCAAA|CCGGCTCACC|GGGAAACAGA|ATGGATCACG|TGGGATACAC|TGCTGGGGTT| 240
|CCTCGCTGCG|AGAACCTGCC|CGGTTTGAGT|CATGGTCAGC|TGGCAACCTG|CGAGATAATT| 300
|CCCACGCCGG|TCACATCTGA|CGTTGCCT| | | | 328

FIG. 3L

SEQ. ID. NO. 12

```
AACACGTCAT GTGCAGGAGT GACATTGTGC CGCGGAGAAA CTCAGACCGC ATCCCGTAAC    60
CACACTGAGT GGGAAAATCT GCTGGCTATG TTTTCTGTGA TTATCTATGC CTTAGATCAC   120
AACTGTCACC CG                                                       132
```

FIG. 4A   1 2 3 4 5 6 7 8 9 10 11 12 13 14 15 16 17 18 19 — M
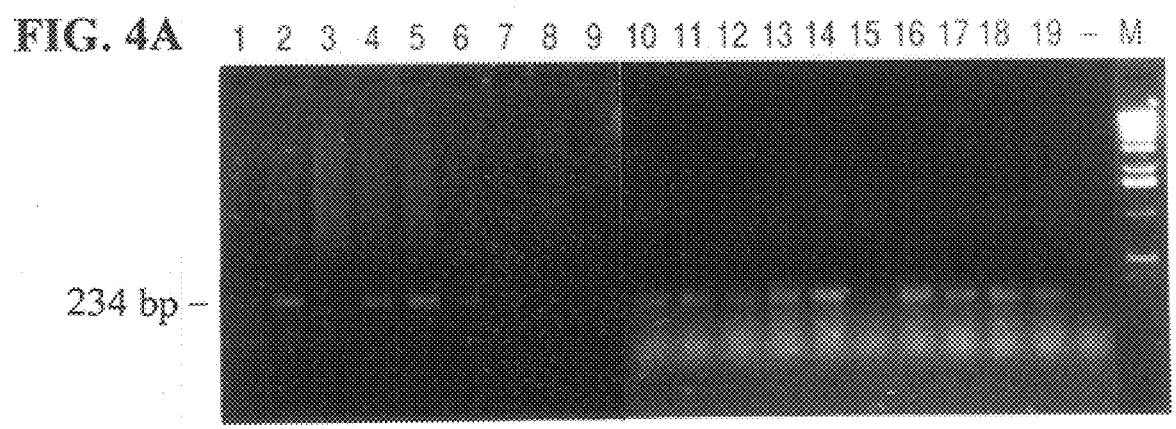
234 bp —
FIG. 4B

FIG. 6

```
              1
HSVSA  MLTDKTIIMS  LTSRLFADEI  TKLQKKIGSI  LPLQDPHKLQ  SLDTLGLNAV   50
   KS  MALDKSIVVN  FTSRLFADEL  AALQSKIGSV  LPLGDCHRLQ  NIQALGLGCV
  EBV  ..MDLKVVVS  LSSRLYTDEI  AKMQQRIGCI  LPLASTHGTQ  NMQGLGLGQV

51
HSVSA  CSRDVFPDYV  HMFSYLSKCT  LAILEEVNPD  NLILTRLDPS  ETYQIKNVYE  100
   KS  CSRETSPDYI  QIMQYLSKCT  LAVLEEVRPD  SLRLTRMDPS  DNLQIKNVYA
  EBV  YSLEIVPDYV  SMYNYLSDCT  LAVLDEVSVD  SLILTKIVPG  QTYAIKNKYQ

101
HSVSA  PMFQWDGFSN  LTVIPPVFGR  QQATVTLESN  GFDLVFPSVV  PSDLAQAIIG  150
   KS  PFFQWDSNTQ  LAVLPPFFSR  KDSTIVLESN  GFDPVFPMVV  PQQLGHAILQ
  EBV  PFFQWHGTGS  LSVMPPVFGR  EHATVKLESN  DVDIVFPMVL  PTPIAEEVLQ

151
HSVSA  KILLYNLYSR  LVESDP.EIN  IEEVNMYTTN  VTHMGRHYML  DINHNPNEA  200
   KS  QLLVYHIYSK  ISAGAPDDVN  MAELDLYTTN  VSFMGRTYRL  DVDNTDPRTA
  EBV  KILLFNVYSR  VVMQAPGNAD  MLDVHMHLGS  VSYLGHHYEL  ALPEVPGPLG

201
HSVSA  LKSLDDLAVY  TCILSALIPR  ACLRVLTILM  RHDQHELLDV  FRGIVPREVY  250
   KS  LRVLDDLSMY  LCILSALVPR  GCLRLLTALV  RHDRHPLTEV  FEGVVPDEVT
  EBV  LALDNLSLY   FCIMVTLLPR  ASMRLVRGLI  RHEHHDLLNL  FQEMVPDEIA

251
HSVSA  EIDANALSIG  DDITRMTTFI  TYLQSLSSIF  NLGAKLHLSS  YASETQTATC  300
   KS  RIDLDQLSVP  DDITRMRVMF  SYLQSLSSIF  NLGPRLHVYA  YSAETLAASC
  EBV  RIDLDDLSVA  DDLSRMRVMM  TYLQSLASLF  NLGPRLATAA  YSQETLTATC

301
HSVSA  WISYC
   KS  WMYSPR
  EBV  WLR
```

FIG. 7A-1

SEQ. ID. NO. 18

Leu Glu Gln Arg Pro Phe Pro Tyr Leu Ala Thr Glu Ala Asn Leu Leu
1               5                   10                  15

Thr Gln Ile Lys Glu Ser Ala Ala Asp Gly Leu Phe Lys Ser Phe Gln
            20                  25                  30

Leu Leu Leu Gly Lys Asp Ala Arg Glu Gly Ser Val Arg Phe Glu Ala
        35                  40                  45

Leu Leu Gly Val Tyr Thr Asn Val Val Glu Phe Val Lys Phe Leu Glu
    50                  55                  60

Thr Ala Leu Ala Ala Ala Cys Val Asn Thr Glu Phe Lys Asp Leu Arg
65                  70                  75                  80

Arg Met Asp Gly Lys Ile Gln Phe Lys Ile Ser Met Pro Thr Ile Ala
                85                  90                  95

His Gly Asp Gly Arg Arg Pro Asn Lys Gln Arg Gln Tyr Ile Val Met
            100                 105                 110

Lys Ala Cys Asn Lys His His Ile Gly Ala Glu Ile Glu Leu Ala Ala
        115                 120                 125

Ala Asp Ile Glu Leu Leu Phe Ala Glu Lys Glu Thr Pro Leu Asp Phe
    130                 135                 140

Thr Glu Tyr Ala Gly Ala Ile Lys Thr Ile Thr Gly Ala Leu Gln Phe
145                 150                 155                 160

Gly Met Asp Ala Leu Glu Arg Cys Leu Val Asp Thr Val Leu Ala Val
                165                 170                 175

Lys Leu Arg His Ala Pro Pro Val Phe Ile Leu Lys Thr Leu Gly His
            180                 185                 190

Pro Val Tyr Ser Glu Arg Gly Leu Lys Lys Cys Val Lys Ser Asp Met
        195                 200                 205

Val Ser Met Phe Lys Ala His Leu Ile Asn Ile His Phe Phe Leu Asp
    210                 215                 220

Lys Ala Glu Leu Met Thr Arg Gly Lys Gln Tyr Val Leu Thr Met Leu
225                 230                 235                 240

Ser Asp Met Leu Ala Ala Val Cys Glu Asp Thr Val Phe Lys Gly Val
                245                 250                 255

Ser Thr Tyr Thr Thr Ala Ser Gly Gln Gln Val Ala Gly Val Leu Glu
            260                 265                 270

Thr Thr Asp Ser Val Met Arg Arg Leu Met Asn Leu Leu Gly Gln Val
        275                 280                 285

Glu Ser Ala Met Ser Gly Pro Ala Ala Tyr Ala Ser Tyr Val Val Arg
290                 295                 300

Gly Ala Asn Leu Val Thr Ala Val Ser Tyr Gly Arg Ala Met Arg Asn
305                 310                 315                 320

Phe Glu Gln Phe Met Ala Arg Ile Val Asp His Pro Thr Ser Ala Ser
                325                 330                 335

Val Glu Gly Asp Lys Ala Ala Leu Arg Arg His Asp Glu Gln Arg Thr
            340                 345                 350

FIG. 7A-2

Arg Ile Ala Ala Ser Leu Val Lys Ile Gly Asp Lys Phe Val Ala Ile
         355                 360                 365

Glu Ser Leu Gln Arg Met Tyr Asn Glu Thr Gln Phe Pro Cys Pro Leu
    370                 375                 380

Asn Arg Arg Ile Gln Tyr Thr Tyr Phe Phe Pro Val Gly Leu His Leu
385                 390                 395                     400

Pro Val Pro Arg Tyr Ser Thr Ser Val Ser Val Arg Gly Val Glu Ser
                405                     410                 415

Pro Ala Ile Gln Ser Thr Glu Thr Trp Val Val Asn Lys Asn Asn Val
            420                 425                 430

Pro Leu Cys Phe Gly Tyr Gln Asn Ala Leu Lys Ser Ile Cys His Pro
        435                 440                 445

Arg Met His Asn Pro Thr Ser Gln Pro Pro Ala Gln Asn Gln Ala Phe
    450                 455                 460

Pro Asp Pro Asp Gly Gly His Gly Tyr Gly Leu Arg Tyr Glu Gln Thr
465                 470                 475                 480

Pro Asn Met Asn Leu Phe Arg Thr Phe His Gln Tyr Tyr Met Gly Lys
                485                 490                 495

Asn Val Ala Phe Val Pro Asp Val Ala Gln Lys Ala Leu Val Thr Thr
            500                 505                 510

Glu Asp Leu Leu His Pro Thr Ser His Arg Leu Leu Arg Leu Glu Val
        515                 520                 525

His Pro Phe Phe Asp Phe Phe Val His Pro Cys Pro Gly Ala Arg Gly
    530                 535                 540

Ser Tyr Arg Ala Thr His Arg Thr Met Val Gln Asn Ile Pro Gln Pro
545                 550                 555                 560

Val Ala Pro Arg Glu Phe Gln Glu Ser Arg Gly Ala Gln Phe Asp Ala
                565                 570                 575

Val Thr Asn Met Thr His Val Ile Asp Gln Leu Thr Ile Asp Val Ile
            580                 585                 590

Gln Glu Thr Ala Phe Asp Pro Ala Tyr Pro Leu Phe Cys Tyr Val Ile
        595                 600                 605

Glu Ala Met Ile His Gly Gln Glu Lys Phe Val Met Asn Met Pro
    610                 615                 620

Leu Ile Ala Leu Val Ile Gln Thr Tyr Trp Val Asn Ser Gly Lys Leu
625                 630                 635                 640

Ala Phe Val Asn Gly Tyr His Met Val Arg Phe Ile Cys Thr His Met
            645                 650                 655

Gly Ile Gly Ser Ile Pro Lys Glu Ala His Gly His Tyr Arg Lys Ile
        660                 665                 670

Leu Gly Glu Leu Ile Gly Leu Glu Gln Ala Leu Leu Lys Leu Ala Gly
    675                 680                 685

His Glu Thr Val Gly Arg Thr Pro Ile Thr His Leu Val Ser Ala Leu
    690                 695                 700

FIG. 7A-3

Leu Asp Pro His Leu Leu Pro Pro Phe Ala Tyr His Asp Val Phe Thr
705                710                715                720

Asp Leu Met Gln Lys Ser Ser Arg Gln Pro Ile Ile Lys Ile Gly Asp
            725                730                735

Gln Asn Tyr Asp Asn Pro Gln Asn Arg Ala Thr Phe Ile Asn Leu Arg
            740                745                750

Gly Arg Met Glu Asp Leu Val Asn Asn Leu Val Asn Ile Tyr Gln Thr
            755                760                765

Arg Val Asn Glu Asp His Asp Glu Arg His Val Leu Asp Val Ala Pro
    770                775                780

Leu Asp Glu Asn Asp Tyr Asn Pro Val Leu Glu Lys Leu Phe Tyr Tyr
785                790                795                800

Val Leu Met Pro Val Cys Ser Asn Gly His Met Cys Gly Met Gly Val
            805                810                815

Asp Tyr Gln Asn Val Ala Leu Thr Leu Thr Tyr Asn Gly Pro Val Phe
            820                825                830

Ala Asp Val Val Asn Ala Gln Asp Asp Ile Leu Leu His Leu Glu Asn
        835                840                845

Gly Thr Leu Lys Asp Ile Leu Gln Ala Gly Asp Ile Arg
    850                855                860

FIG. 7B

SEQ. ID. NO. 19

```
Pro Thr Val Asp Met Ile Arg Val Leu Cys Thr Ser Phe Leu Thr Cys
 1           5                   10                  15
Pro Phe Val Thr Gln Ala Ala Arg Val Ile Thr Lys Arg Asp Pro Ala
            20                  25                  30
Gln Ser Phe Ala Thr His Glu Tyr Gly Lys Asp Val Ala Gln Thr Val
            35                  40                  45
Leu Val Asn Gly Phe Gly Ala Phe Ala Val Ala Asp Arg Ser Ala Glu
        50                  55                  60
Ala Ala Glu Thr Met Phe Tyr Pro Val Pro Phe Asn Lys Leu Tyr Ala
 65                  70                  75                  80
Asp Pro Leu Val Ala Asp Thr Leu His Pro Leu Leu Pro Asn Tyr Val
                85                  90                  95
Thr Arg Leu Pro Asn Gln Arg Asn Ala Val Val Phe Asn Val Pro Ser
                100                 105                 110
Asn Leu Met Ala Glu Tyr Glu Glu Trp His Lys Ser Pro Val Ala Ala
            115                 120                 125
Tyr Ala Ala Ser Cys Gln Ala Thr Pro Gly Ala Ile Ser Ala Met Val
    130                 135                 140
Ser Met His Gln Lys Leu Ser Ala Pro Ser Phe Ile Cys Gln Ala Lys
145                 150                 155                 160
His Arg Met His Pro Gly Phe Ala Met Thr Val Val Arg Thr Asp Glu
                165                 170                 175
Val Leu Ala Glu His Ile Leu Tyr Cys Ser Arg Ala Ser Thr Ser Met
                180                 185                 190
Phe Val Gly Leu Pro Ser Val Val Arg Arg Glu Val Arg Ser Asp Ala
        195                 200                 205
Val Thr Phe Glu Ile Thr His Glu Ile Ala Ser Leu His Thr Ala Leu
    210                 215                 220
Gly Tyr Ser Ser Val Ile Ala Pro Ala His Val Ala Ala Ile Thr Thr
225                 230                 235                 240
Asp Met Gly Val His Cys Gln Asp Leu Phe Met Ile Phe Pro Gly Asp
                245                 250                 255
Ala Tyr Gln Asp Arg Gln Leu His Asp Tyr Ile Lys Met Lys Ala Gly
            260                 265                 270
```

FIG. 7C

SEQ. ID. NO. 20

Gly Val Pro Arg Cys Glu Asn Leu Pro Gly Leu Ser His Gly Gln Leu
1           5               10              15

Ala Thr Cys Glu Ile Leu Pro Thr Pro Val Thr Ser Asp Val Ala Tyr
        20              25              30

Phe Gln Thr Pro Ser Asn Pro Arg Gly Arg Ala Ala Ser Val Val Ser
    35              40              45

Cys Asp Ala Tyr Ser Asn Glu Ser Ala Glu Arg Leu Phe Tyr Asp His
    50              55              60

Ser Ile Pro Asp Pro Ala Tyr Glu Cys Arg Ser Thr Asn Asn Pro Trp
65              70              75              80

Ala Ser Gln Arg Gly Ser Leu Gly Asp Val Leu Tyr Asn Ile Thr Phe
                85              90              95

Arg Gln Thr Ala Leu Pro Gly Met Tyr Ser Pro Cys Arg Gln Phe Phe
            100             105             110

His Lys Glu Asp Ile Met Arg Tyr Asn Arg Gly Leu Tyr Thr Leu Val
        115             120             125

Asn Glu Tyr Ser Ala Arg Leu Ala Gly Ala Pro Ala Thr Ser Thr Thr
    130             135             140

Asp Leu Gln Tyr Val Val Val Asn Gly Thr Asp Val Phe Leu Asp Gln
145             150             155             160

Pro Cys His Met Leu Gln Glu Ala Tyr Pro Thr Leu Ala Ala Ser His
                165             170             175

Arg Val Met Leu Ala Glu Tyr Met Ser Asn Lys Gln Thr His Ala Pro
            180             185             190

Val His Met Gly Gln Tyr Leu Ile Glu Glu Val Ala Pro Met Lys Arg
        195             200             205

Leu Leu Lys Leu Gly Asn Lys Val Val Tyr
210             215

UNIQUE ASSOCIATED KAPOSI'S SARCOMA VIRUS SEQUENCES AND USES THEREOF

This application is a divisional application of Ser. No. 08/343,101, filed Nov. 21, 1994 U.S. Pat. No. 5,830,759 which is a continuation-in-part application of U.S. Ser. No. 08/292,365, filed on Aug. 18, 1994 now abandoned, which is incorporated herein by reference.

FIELD OF THE INVENTION

This invention relates to a novel isolated herpesvirus that is associated with Kaposi's sarcoma (KS). Methods and compositions relating to the detection and treatment of the virus and KS are described.

BACKGROUND OF THE INVENTION

Throughout this application, various publications may be referenced by Arabic numerals in brackets. Full citations for these publications may be found at the end of the specification immediately preceding the claims. The disclosures of the publications cited herein are in their entirety hereby incorporated by reference into this application to more fully describe the state of the art to which this invention pertains.

Kaposi's sarcoma (KS) is the most common neoplasm occurring in persons with acquired immunodeficiency syndrome (AIDS). Approximately 15–20% of AIDS patients develop this neoplasm which rarely occurs in immunocompetent individuals [13, 14]. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS [6, 15, 55, 83]. KS is uncommon among adult AIDS patients infected through heterosexual or parenteral HIV transmission, or among pediatric AIDS patients infected through vertical HIV transmission [77]. Agents previously suspected of causing KS include cytomegalovirus, hepatitis B virus, human papillomavirus, Epstein-Barr virus, human herpesvirus 6, human immunodeficiency virus (HIV), and Mycoplasma penetrans [18, 23, 85, 91, 92]. Non-infectious environmental agents, such as nitrite inhalants, also have been proposed to play a role in KS tumorigenesis [33]. Extensive investigations, however, have not demonstrated an etiologic association between any of these agents and AIDS-KS [37, 44, 46, 90].

SUMMARY OF THE INVENTION

This invention provides an isolated DNA molecule which is at least 30 nucleotides in length and which uniquely defines a herpesvirus associated with Kaposi's sarcoma. This invention provides an isolated herpesvirus associated with Kaposi's sarcoma.

This invention provides an isolated peptide encoded by the isolated DNA molecule. Further, this invention provides an isolated DNA virus wherein the viral DNA is about 270 kb in size; wherein the DNA encodes a thymidine kinase; and wherein the viral DNA is capable of selectively hybridizing to a nucleic acid probe selected from the group consisting of SEQ. ID NOs: 10–12.

This invention provides an antibody specific to the peptide. Antisense and triplex oligonucleotide molecules are also provided. Further, this invention provides a transgenic nonhuman mammal and a cell line containing at least a portion of the isolated DNA molecule.

This invention provides a method of vaccinating a subject for KS, prophylaxis diagnosing or treating a subject with KS and detecting expression of a DNA virus associated with Kaposi's sarcoma in a cell.

BRIEF DESCRIPTION OF THE FIGURES

FIGS. 3A–3L: Nucleotide sequences of the DNA herpesvirus associated with KS (KSHV) (FIG. 3A), KS 330Bam (FIG. 3B), KS 3R (FIG. 3C), KS 627Bam (FIG. 3D), KS 5–5.9F (FIG. 3E), KS 3.5.9 (FIG. 3F), KS 5.5.9 (FIG. 3G), KS 2.5.9 (FIG. 3H), and KS 6.5.9 (FIG. 3I). FIG. 3A is the extended nucleotide sequence of a 9404 bp segment, derived from a genomic library of a KS lesion. An entire open reading frame from bp 4160–5077 is homologous to the ORF26 site of herpesvirus saimiri and the BDLF1 of EBV open reading frames (55% and 56% respectively). The ORF26 site of the herpesvirus saimiri codes for the virion polypeptide 23 (VP23). The start methionine codon is at bp 4160 and stop codon at bp 5075 for this reading frame. The KS330Bam sequence is internal to this reading frame at bp 4420–4749 and has a Pvu II site between 4612–4613 marking the junction between the 1.1 and 3.0 kb fragments cloned from the KS genomic library. Base pairs 5398–6056 are homologous to the corresponding regions of the (minor) capsid protein open reading frames of Epstein-Barr virus (EBV). The Bam HI restriction sites (GGATCC) are at bp 4420–4425 and bp 4744–4749, the primer set for KS330$_{234}$ is at bp 4514–4533 and bp 4737–4745, and the internal probe used to detect the PCR amplification product is at bp 4605–4629. In FIGS. 3B and 3C Bam HI the restriction sites (GGATCC) are underlined. Base pairs 5398–6056 are homologous to the corresponding regions of the major capsid protein open reading frames ORF27 (66%) of herpesvirus saimiri and BcLF1 (68%) of Epstein-Barr virus (EBV). Base pairs 5398–6056 are homologous to the corresponding regions of the DNA molecule which encodes a polypeptide which is homologous to at least a portion of a herpesvirus saimiri and EBV tegument polypeptides. FIG. 3E is a DNA molecules which encode a polypeptide which are homologous to at least a portion of the EBV thymidine kinase (TK) polypeptide.

FIGS. 4A–4B: PCR amplification of a representative set of KS-derived DNA samples using $KS330_{234}$ primers. FIG. 4A shows the agarose gel of the amplification products from 19 KS DNA samples (lanes 1–19) and FIG. 43 shows specific hybridization of the PCR products to a $^{32}P$ end-labelled 25 bp internal oligonucleotide (FIG. 3B) after transfer of the gel to a nitrocellulose filter. Negative samples in lanes 3 and 15 respectively lacked microscopically detectable KS in the sample or did not amplify the constitutive p53 exon 6, suggesting that these samples were negative for technical reasons. An additional 8 AIDS-KS samples were amplified and all were positive for $KS330_{234}$. Lane 20 is a negative control and Lane M is a molecular weight marker.

FIG. 6: Comparison of amino acid homologies between EBV ORF BDLF1, HSVSA ORF 26 and a 918 bp reading frame of the Kaposi's sarcoma agent which includes KS330Bam. Amino acid identity is denoted by reverse lettering. In HSVSA, ORF 26 encodes a minor capsid VP23 which is a late gene product.

FIGS. 7A–7C: Amino acid sequence of the KSHV major capsid protein fragment (SEQ ID NOs: 18–20).

DETAILED DESCRIPTION OF THE INVENTION

Definitions

Figure 1:
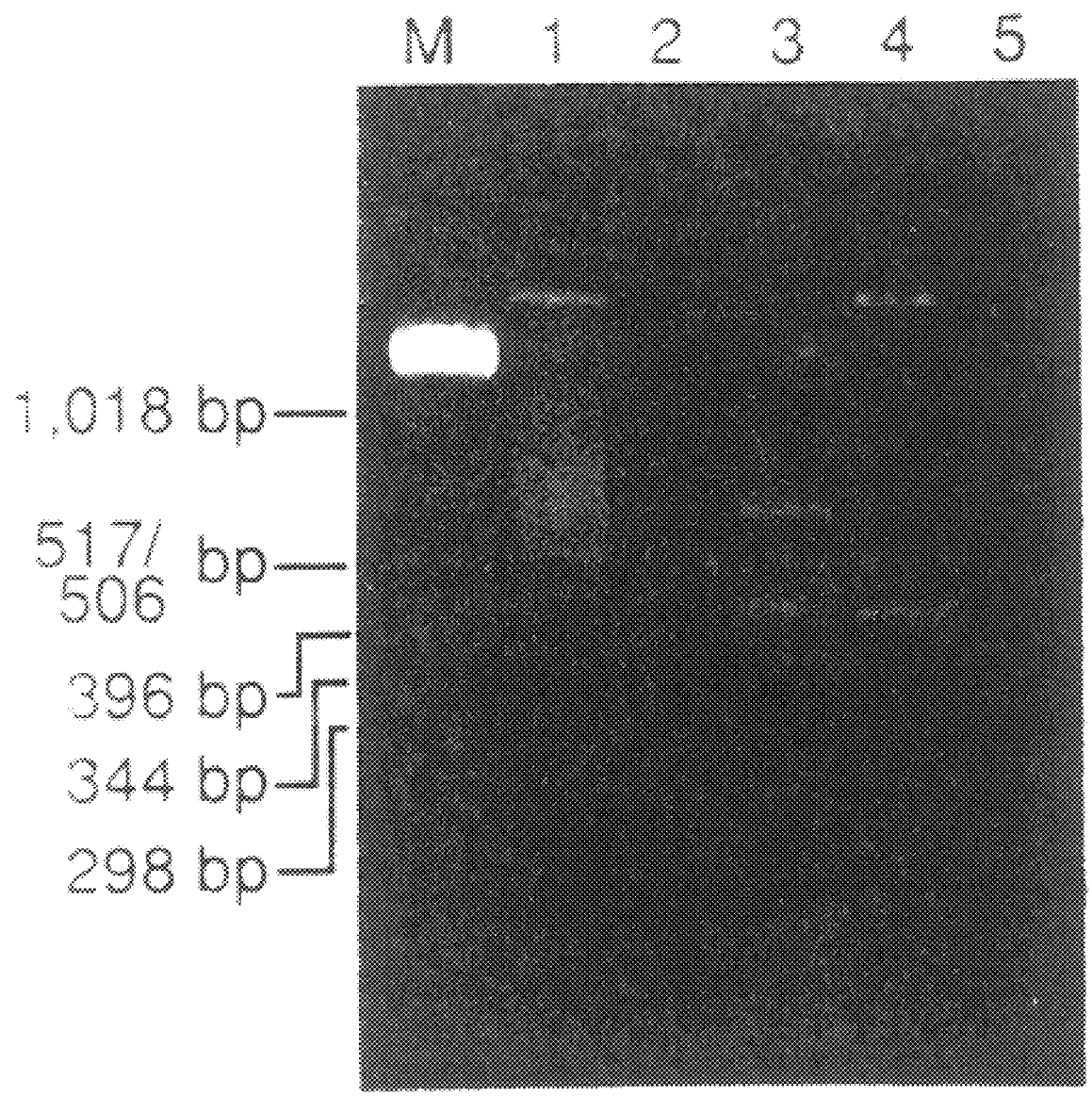
FIG. 1: Agarose gel electrophoresis of RDA products from AIDS-KS tissue and uninvolved tissue. RDA was performed on DNA extracted from KS skin tissue and uninvolved normal skin tissue obtained at autopsy from a homosexual man with AIDS-KS. Lane 1 shows the initial PCR amplified genomic representation of the AIDS-KS DNA after Bam HI digestion. Lanes 2–4 show that subsequent cycles of ligation, amplification, hybridization and digestion of the RDA products resulted in amplification of discrete bands at 380, 450, 540 and 680 bp. RDA of the extracted AIDS-KS DNA performed against itself resulted in a single band at 540 bp (lane 5). Bands at 380 bp and 680 bp correspond to KS330Bam and KS627Bam respectively after removal of 28 bp priming sequences. Bands at 450 and 540 bp hybridized nonspecifically to both KS and non-KS human DNA. Lane M is a molecular weight marker.

The following standard abbreviations are used throughout the specification to indicate specific nucleotides:

| C = cytosine | A = adenosine |
|---|---|
| T = thymidine | G = guanosine |

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

By a nucleic acid sequence "homologous to" or "complementary to", it is meant a nucleic acid that selectively hybridizes, duplexes or binds to viral DNA sequences encoding proteins or portions thereof when the DNA sequences encoding the viral protein are present in a human genomic or cDNA library. A DNA sequence which is homologous to a target sequence can include sequences which are shorter or longer than the target sequence so long as they meet the functional test set forth. Hybridization conditions are specified along with the source of the CDNA library.

Typically, the hybridization is done in a Southern blot protocol using a 0.2×SSC, 0.1% SDS, 65° C. wash. The term "SSC" refers to a citrate-saline solution of 0.15M sodium chloride and 20 Mm sodium citrate. Solutions are often expressed as multiples or fractions of this concentration. For example, 6×SSC refers to a solution having a sodium chloride and sodium citrate concentration of 6 times this amount or 0.9M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acid molecules or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap weights, share at least 90 percent sequence identity, preferably at least 95 percent sequence identity, more preferably at least 99 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a herpesvirus peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the herpesvirus of the invention in the presence of a heterogeneous population of proteins and other biologics including viruses other than the herpesvirus. Thus, under designated immunoassay conditions, the specified antibodies bind to the herpesvirus antigens and do not bind in a significant amount to other antigens present in the sample. Specific binding to an antibody under such conditions may require an antibody that is selected for its specificity for a particular protein. For example, antibodies raised to the human herpesvirus immunogen described herein can be selected to obtain antibodies specifically immunoreactive with the herpesvirus proteins and not with other proteins. These antibodies recognize proteins homologous to the human herpesvirus protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane [32] for a description of immunoassay formats and conditions that can be used to determine specific immunoreactivity.

"Biological sample" as used herein refers to any sample obtained from a living organism or from an organism that has died. Examples of biological samples include body fluids and tissue specimens.

I. KAPOSIS'S SARCOMA (KS)—ASSOCIATED HERPESVIRUS

This invention provides an isolated DNA molecule which is at least 30 nucleotides in length and which uniquely defines a herpesvirus associated with Kaposi's sarcoma.

In one embodiment the isolated DNA molecule comprises at least a portion of the nucleic acid sequence as shown in FIGS. 3A–3O (SEQ ID NOs: 1–15). In another embodiment the isolated DNA molecule is a 330 base pair (bp) sequence. In another embodiment the isolated DNA molecule is a 12–50 bp sequence. In another embodiment the isolated DNA molecule is a 30–37 bp sequence. In another embodiment the isolated DNA molecule is a 20 bp sequence.

In another embodiment the isolated DNA molecule is genomic DNA. In another embodiment the isolated DNA molecule is cDNA. In another embodiment a RNA is capable of hybridizing with the isolated DNA molecule. As used herein "genomic" means both coding and non-coding regions of the isolated nucleic acid molecule.

Further, the DNA molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, post-transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

This invention provides for a replicable vector comprising the isolated DNA molecule of the DNA virus. The vector includes, but is not limited to: a plasmid, cosmid, λ phage or yeast artificial chromosome (YAC) which contains at least a portion of the isolated nucleic acid molecule.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Regulatory elements required for expression include promoter or enhancer sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

This invention provides a host cell containing the above vector. The host cell may contain the isolated DNA molecule artificially introduced into the host cell. The host cell may be a eukaryotic or bacterial cell (such as *E. coli*), yeast cells, fungal cells, insect cells and animal cells. Suitable animal cells include, but are not limited to Vero cells, HeLa cells, Cos cells, CV1 cells and various primary mammalian cells.

This invention provides an isolated herpesvirus associated with Kaposi's sarcoma. In one embodiment the herpesvirus comprises at least a portion of a nucleotide sequence as shown in FIGS. 3A–3O (SEQ ID NOs: 1–15).

In one embodiment the herpesvirus may be a DNA virus. In another embodiment the herpesvirus may be a Herpesviridae. In another embodiment the herpesvirus may be a gammaherpesvirinae. The classification of the herpesvirus may vary based on the phenotypic or molecular characteristics which are known to those skilled in the art.

This invention provides an isolated DNA virus wherein the viral DNA is about 270 kb in size, wherein the viral DNA encodes a thymidine kinase, and wherein the viral DNA is capable of selectively hybridizing to a nucleic acid probe selected from the group consisting of SEQ ID NOs 10–12. Further, the isolated DNA virus may be a herpesvirus having one of the nucleic acid sequences in the group consisting of SEQ ID NOs 10–12. In one embodiment the viral DNA is in a range of 190–270 kb in size. In another embodiment the viral DNA is 220–270 kb in size.

The KS-associated human herpesvirus of the invention is associated with KS and is involved in the etiology of the disease. The taxonomic classification of the virus has not yet been made and will be based on phenotypic or molecular characteristics known to those of skill in the art. However, the novel KS-associated virus is a DNA virus that appears to be related to the Herpesviridae family and the gammaherpesvirinae subfamily, on the basis of nucleic acid homology.

A. Sequence Identity of the Viral DNA and its Proteins

The human herpesvirus of the invention is not limited to the virus having the specific DNA sequences described herein. The KS-associated human herpesvirus DNA shows substantial sequence identity, as defined above, to the viral DNA sequences described herein. DNA from the human herpesvirus typically selectively hybridizes to one or more of the following three nucleic acid probes:

Probe 1 (SEQ ID NO:10)
AGCCGAAAGG ATTCCACCAT TGTGCTCGAA TCCAACGGAT

TTGACCCCGT GTTCCCCATG GTCGTGCCGC AGCAACTGGG

GCACGCTATT CTGCAGCAGC TGTTGGTGTA CCACATCTAC

TCCAAAATAT CGGCCGGGGC CCCGGATGAT GTAAATATGG

CGGAACTTGA TCTATATACC ACCAATGTGT CATTTATGGG

GCGCACATAT CGTCTGGACG TAGACAACAC GGA

Probe 2 (SEQ ID NO:11):
GAAATTACCC ACGAGATCGC TTCCCTGCAC ACCGCACTTG

GCTACTCATC AGTCATCGCC CCGGCCCACG TGGCCGCCAT

AACTACAGAC ATGGGAGTAC ATTGTCAGGA CCTCTTTATG

ATTTTCCCAG GGGACGCGTA TCAGGACCGC CAGCTGCATG

ACTATATCAA AATGAAAGCG GGCGTGCAAA CCGGCTCACC

GGGAAACAGA ATGGATCACG TGGGATACAC TGCTGGGGTT

CCTCGCTGCG AGAACCTGCC CGGTTTGAGC CATGGTCAGC

TGGCAACCTG CGAGATAATT CCCACGCCGG TCACATCTGA

CGTTGCCT

Probe 3 (SEQ ID NO:12):
AACACGTCAT GTGCAGGAGT GACATTGTGC CGCGGAGAAA

CTCAGACCGC ATCCCGTAAC CACACTGAGT GGGAAAATCT

GCTGGCTATG TTTTCTGTGA TTATCTATGC CTTAGATCAC

AACTGTCACC CG

Hybridization of a viral DNA to the nucleic acid probes listed above is determined by using standard nucleic acid hybridization techniques as described herein. In particular, PCR amplification of a viral genome can be carried out using the following three sets of PCR primers:

1) AGCCGAAAGGATTCCACCAT;

TCCGTGTTGTCTACGTCCAG (SEQ ID NO:13)

2) GAAATTACCCACGAGATCGC;

AGGCAACGTCAGATGTGA (SEQ ID NO:14)

3) AACACGTCATGTGCAGGACTGAC;

CGGGTGACAGTTGTGATCTAAGG (SEQ ID NO:15)

In PCR techniques, oligonucleotide primers, as listed above, complementary to the two 3' borders of the DNA region to be amplified are synthesized. The polymerase chain reaction is then carried out using the two primers. See *PCR Protocols: A Guide to Methods and Applications* [74]. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein.

Oligonucleotides for use as probes or PCR primers are chemically synthesized according to the solid phase phosphoramidite triester method first described by Beaucage and Carruthers [19] using an automated synthesizer, as described in Needham-VanDevanter [69]. Purification of oligonucleotides is by either native acrylamide gel electrophoresis or by anion-exchange HPLC as described in Pearson, J. D. and Regnier, F. E. [75A]. The sequence of the synthetic oligonucleotide can be verified using the chemical degradation method of Maxam, A. M. and Gilbert, W. [63].

B. Isolation and Propagation of KS-inducing Strains of the Human Herpesvirus Using conventional methods, the human herpesvirus can be propagated in vitro. For example, standard techniques for growing herpes viruses are described in Ablashi, D. V. [1]. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 μg/ml polybrene for 2 hours at 37° C. prior to infection. Infected cells are observed by demonstrating morphological changes, as well as being positive for antigens from the human herpesvirus by using monoclonal antibodies immunoreactive with the human herpes virus in an immunofluorescence assay.

For virus isolation, the virus is either harvested directly from the culture fluid by direct centrifugation, or the infected cells are harvested, homogenized or lysed and the virus is separated from cellular debris and purified by standard methods of isopycnic sucrose density gradient centrifugation.

One skilled in the art may isolate and propagate the DNA herpesvirus associated with Kaposi's sarcoma (KSHV) employing the following protocol. For body cavity-based lymphomas (BCBL), long-term establishment of a B lymphoid cell line infected with the KSHV from body-cavity based lymphomas (BCBL or BHL-6) is prepared extracting DNA from the Lymphoma tissue using standard techniques [27, 49, 66]. The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at >1×10$^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortilized cells die during course of prolonged cultivation.

Further, the virus may be propagated in a new cell line by removing media supernatant containing the virus from a continuously infected cell line at a concentration of >1×10$^6$ cells/ml. The media is centrifuged at 2000×g for 10 minutes and filtered through a 0.45μ filter to remove cells. The media is applied in a 1:1 volume with cells growing at >1×10$^6$ cells/ml for 48 hours. The cells are washed and pelleted and placed in fresh culture medium, and tested after 14 days of growth.

The KS associated herpesvirus may be isolated from the cell DNA in the following manner. An infected cell line (BHL-6 RCC-1), which can be lysed using standard methods such as hyposmotic shocking and Dounce homogenization, is first pelleted at 2000×g for 10 minutes, the supernatant is removed and centrifuged again at 10,000×g for 15 minutes to remove nuclei and organelles. The supernatant is filtered through a 0.45μ filter and centrifuged again at 100,000×g for 1 hour to pellet the virus. The virus can then be washed and centrifuged again at 100,000×g for 1 hour.

RCC-1 and RCC-1$_{2F5}$ were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

BHL-6 was deposited on Nov. 18, 1994 under ATCC Accession No. CRL pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

C. Immunological Identity of the Virus

The KS-associated human herpesvirus can also be described immunologically. KS-associated human herpesviruses are selectively immunoreactive to antisera generated against a defined immunogen such as the viral major capsid protein depicted in Seq. ID No. 12, herein. Immunoreactivity is determined in an immunoassay using a polyclonal antiserum which was raised to the protein of SEQ ID NOs: 18–20. This antiserum is selected to have low crossreactivity against other herpes viruses and any such crossreactivity is removed by immunoabsorbtion prior to use in the immunoassay.

In order to produce antisera for use in an immunoassay, the protein of SEQ ID NOs: 18–20 is isolated as described herein. For example, recombinant protein can be produced in a mammalian cell line. An inbred strain of mice such as balb/c is immunized with the protein of SEQ ID NOs: 18–20 using a standard adjuvant, such as Freund's adjuvant, and a standard mouse immunization protocol (see [32], supra). Alternatively, a synthetic peptide derived from the sequences disclosed herein and conjugated to a carrier protein can be used an immunogen.

Polyclonal sera are collected and titered against the immunogen protein in an immunoassay, for example, a solid phase immunoassay with the immunogen immobilized on a solid support. Polyclonal antisera with a titer of 10$^4$ or greater are selected and tested for their cross reactivity against other viruses of the gammaherpesvirinae subfamily, particularly human herpes virus types 1–7, by using a standard immunoassay as described in [32], supra. These other gammaherpesvirinae virus can be isolated by standard techniques for isolation herpes viruses as described herein.

The ability of the above viruses to compete with the binding of the antisera to the immunogen protein is determined. The percent crossreactivity for other viruses is calculated, using standard calculations. Those antisera with less than 10% crossreactivity with each of the other viruses listed above is selected and pooled. The cross-reacting antibodies are then removed from the pooled antisera by immunoabsorption with the above-listed viruses.

The immunoabsorbed and pooled antisera are then used in a competitive binding immunoassay procedure as described above to compare an unknown virus preparation to the specific KS herpesvirus preparation described herein and containing the nucleic acid sequence described in SEQ ID NOs: 18–20. In order to make this comparison, the immunogen protein of SEQ ID NOs: 18–20 is the labeled antigen and the virus preparations are each assayed at a wide range of concentrations. The amount of each virus preparation required to inhibit 50% of the binding of the antisera to the labeled immunogen protein is determined. Those viruses that specifically bind to an antibody generated to an immunogen consisting of the protein of SEQ ID NOs: 18–20 are those virus where the amount of virus needed to inhibit 50% of the binding to the protein does not exceed an established amount. This amount is no more than 10 times the amount of the virus that is needed for 50% inhibition for the KS-associated herpesvirus containing the DNA sequence of Seq. ID No. 1. Thus, the KS-associated herpesviruses of the invention can be defined by immunological comparison to the specific strain of the KS-associated herpesvirus for which nucleic acid sequences are provided herein.

This invention provides, a nucleic acid molecule of at least 14 nucleotides capable of specifically hybridizing with the isolated DNA molecule. In one embodiment, the molecule is DNA. In another embodiment, the molecule is RNA. In another embodiment the nucleic acid molecule may be 14–20 nucleotides in length. In another embodiment the nucleic acid molecule may be 16 nucelotides in length.

This invention provides, a nucleic acid molecule of at least 14 nucleotides capable of specifically hybridizing with a nucleic acid molecule which is complementary to the isolated DNA molecule. In one embodiment, the molecule is DNA. In another embodiment, the molecule is RNA.

The nucleic acid molecule of at least 14 nucleotides may hybridize with moderate stringency to at least a portion of a nucleic acid molecule with a sequence shown in FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L (SEQ ID NOs: 1–12).

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide comcentration, and the extent of base mismatching, the combination of parameters is more important than the absolute measure of any one. For Example high stringency may be attained for example by overnight hybridization at about 68° C. in a 6× SSC solution, washing at room temperature with 6× SSC solution, followed by washing at about 68° C. in a 6× SSC in a 0.6× SSX solution.

Hybridization with moderate stringency may be attained for example by: 1) filter pre-hybridizing and hybridizing with a solution of 3× sodium chloride, sodium citrate (SSC), 50% formamide, 0.1M Tris buffer at Ph 7.5, 5× Denhardt's solution; 2.) pre-hybridization at 37° C. for 4 hours; 3) hybridization at 37° C. with amount of labelled probe equal to 3,000,000 cpm total for 16 hours; 4) wash in 2× SSC and 0.1% SDS solution; 5) wash 4× for 1 minute each at room temperature at 4× at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectivly hybridizing it is meant that a probe binds to a given target in a manner that is detectable in a different manner from non-target sequence under high stringency conditions of hybridization. in a different "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., [81] or Ausubel, F., et al., [8].

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the pathogenic organism or disease marker to which the relevant sequence listing relates.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

DNA virus nucleic acid rearrangements/mutations may be detected by Southern blotting, single stranded conformational polymorphism gel electrophoresis (SSCP), PCR or other DNA based techniques, or for RNA species by Northern blotting, PCR or other RNA-based techniques.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, [19], or by the triester method according to Matteucci, et al., [62], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

This invention provides for an isolated DNA molecule which encodes at least a portion of a Kaposi's sarcoma associated herpesvirus: virion polypeptide 23, major capsid protein, capsid proteins, thymidine kinase, or tegument protein.

This invention also provides a method of producing a polypeptide encoded by isolated DNA molecule, which comprises growing the above host vector system under suitable conditions permitting production of the polypeptide and recovering the polypeptide so produced.

This invention provides an isolated peptide encoded by the isolated DNA molecule associated with Kaposi's sarcoma. In one embodiment the peptide may be a polypeptide. Further, this invention provides a host cell which expresses the polypeptide of isolated DNA molecule.

In one embodiment the isolated peptide or polypeptide is encoded by at least a portion of an isolated DNA molecule. In another embodiment the isolated peptide or polypeptide is encoded by at least a portion of a nucleic acid molecule with a sequence as shown in FIG. 3A, FIG. 3C, FIG. 3D, FIG. 3E, FIG. 3F, FIG. 3G, FIG. 3H, FIG. 3I, FIG. 3J, FIG. 3K, or FIG. 3L (SEQ ID NOs: 1–12).

Further, the isolated peptide or polypeptide encoded by the isolated DNA molecule may be linked to a second nucleic acid molecule to form a fusion protein by expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the peptide or polypeptide encoded by the isolated DNA molecule. In one embodiment the antibody is a monoclonal antibody. In another embodiment the antibody is a polyclonal antibody.

The antibody or DNA molecule may be labelled with a detectable marker including, but not limited to: a radioactive label, or a colorimetric, a luminescent, or a fluorescent marker, or gold. Radioactive labels include, but are not limited to: $^3H$, $^{14}C$, $^{32}P$, $^{33}P$, $^{35}S$, $^{36}Cl$, $^{51}Cr$, $^{57}Co$, $^{59}Co$, $^{59}Fe$, $^{90}Y$, $^{125}I$, $^{131}I$, and $^{186}Re$. Fluorescent markers include but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody or nucleic acid molecule complex may be detected by a second antibody which may be linked to an enzyme, such as alkaline phosphatase or horseradish peroxidase. Other enzymes which may be employed are well known to one of ordinary skill in the art.

This invention provides a method to select specific regions on the polypeptide encoded by the isolated DNA molecule of the DNA virus to generate antibodies. The protein sequence may be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the isolated DNA molecule of the DNA virus in living animals, in humans, or in biological tissues or fluids isolated from animals or humans.

II. IMMUNOASSAYS

The antibodies raised against the viral strain or peptides may be detectably labelled, utilizing conventional labelling techniques well-known to the art. Thus, the antibodies may be radiolabelled using, for example, radioactive isotopes such as $^3H$, $^{125}I$, $^{131}I$, and $^{35}S$.

The antibodies may also be labelled using fluorescent labels, enzyme labels, free radical labels, or bacteriophage labels, using techniques known in the art. Typical fluorescent labels include fluorescein isothiocyanate, rhodamine, phycoerythrin, phycocyanin, alophycocyanin, and Texas Red.

Since specific enzymes may be coupled to other molecules by covalent links, the possibility also exists that they might be used as labels for the production of tracer materials. Suitable enzymes include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

Once labeled, the antibody may be employed to identify and quantify immunologic counterparts (antibody or antigenic polypeptide) utilizing techniques well-known to the art.

A description of a radioimmunoassay (RIA) may be found in *Laboratory Techniques in Biochemistry and Molecular Biology* [52], with particular reference to the chapter entitled "An Introduction to Radioimmune Assay and Related Techniques" by Chard, T., incorporated by reference herein.

A description of general immunometric assays of various types can be found in the following U.S. Pat. No. 4,376,110 (David et al.) or U.S. Pat. No. 4,098,876 (Piasio).

A. Assays for Viral Antigens

In addition to the detection of the causal agent using nucleic acid hybridization technology, one can use immunoassays to detect for the virus, specific peptides, or for antibodies to the virus or peptides. A general overview of the applicable technology is in Harlow and Lane [32], incorporated by reference herein.

In one embodiment, antibodies to the human herpesvirus can be used to detect the agent in the sample. In brief, to produce antibodies to the agent or peptides, the sequence being targeted is expressed in transfected cells, preferably bacterial cells, and purified. The product is injected into a mammal capable of producing antibodies. Either monoclonal or polyclonal antibodies (as well as any recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane [32] at pages 567–573 and 584–589.

Monoclonal antibodies or recombinant antibodies may be obtained by various techniques familiar to those skilled in the art. Briefly, spleen cells or other lymphocytes from an animal immunized with a desired antigen are immortalized, commonly by fusion with a myeloma cell (see, Kohler and Milstein [50], incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. New techniques using recombinant phage antibody expression systems can also be used to generate monoclonal antibodies. See for example: McCafferty, J et al. [64]; Hoogenboom, H. R. et al. [39]; and Marks, J. D. et al. [60].

Such peptides may be produced by expressing the specific sequence in a recombinantly engineered cell such as bacteria, yeast, filamentous fungal, insect (especially employing baculoviral vectors), and mammalian cells. Those of skill in the art are knowledgeable in the numerous expression systems available for expression of herpes virus protein.

Briefly, the expression of natural or synthetic nucleic acids encoding viral protein will typically be achieved by operably linking the desired sequence or portion thereof to a promoter (which is either constitutive or inducible), and incorporated into an expression vector. The vectors are suitable for replication or integration in either prokaryotes or eukaryotes. Typical cloning vectors contain antibiotic resistance markers, genes for selction of transformants, inducible or regulatable promoter regions, and translation terminators that are useful for the expression of viral genes.

Methods for the expression of cloned genes in bacteria are also well known. In general, to obtain high level expression of a cloned gene in a prokaryotic system, it is advisable to construct expression vectors containing a strong promoter to direct mRNA transcription. The inclusion of selection markers in DNA vectors transformed in *E. coli* is also useful. Examples of such markers include genes specifying resistance to antibiotics. See [81] supra, for details concerning selection markers and promoters for use in *E. coli*. Suitable eukaryote hosts may include plant cells, insect cells, mammalian cells, yeast, and filamentous fungi.

Methods for characterizing naturally processed peptides bound to MHC (major histocompatibility complex) I molecules have been developed. See, Falk et al. [24], and PCT publication No. WO 92/21033 published Nov. 26, 1992, both of which are incorporated by reference herein. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey, et al. [45], incorporated by reference herein, and of the human MHC class I molecule, HLA-A2.1 type by mass spectrometry (Hunt, et al. [40], incorporated by reference herein). See also, Rötzschke and Falk [79], incorporated by reference herein for a general review of the characterization of naturally processed peptides in MHC class I. Further, Marloes, et al. [61], incorporated by reference herein, describe how class I binding motifs can be applied to the identification of potential viral immunogenic peptides in vitro.

The peptides described herein produced by recombinant technology may be purified by standard techniques well known to those of skill in the art. Recombinantly produced viral sequences can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired peptide.

The proteins may be purified to substantial purity by standard techniques well known in the art, including selective precipitation with such substances as ammonium sulfate, column chromatography, immunopurification methods, and others. See, for instance, Scopes, R. [84], incorporated herein by reference.

B. Serological Tests for the Presence of Antibodies to the Human Herpesvirus

This invention further embraces diagnostic kits for detecting the presence of a KS agent in biological samples, such as serum or solid tissue samples, comprising a container containing antibodies to the human herpesvirus, and instructional material for performing the test. Alternatively, inactivated viral particles or peptides or viral proteins derived from the human herpesvirus may be used in a diagnostic kit to detect for antibodies specific to the KS associated human herpesvirus.

Diagnostic kits for detecting the presence of a KS agent in tissue samples, such as skin samples or samples of other affected tissue, comprising a container containing a nucleic acid sequence specific for the human herpesvirus and instructional material for detecting the KS-associated herpesvirus are also included. A container containing nucleic acid primers to any one of such sequences is optionally included as are antibodies to the human herpesvirus as described herein.

Antibodies reactive with antigens of the human herpesvirus can also be measured by a variety of immunoassay methods that are similar to the procedures described above for measurement of antigens. For a review of immunological and immunoassay procedures applicable to the measurement of antibodies by immunoassay techniques, see *Basic and Clinical Immunology* 7th Edition [12], and [32], supra.

In brief, immunoassays to measure antibodies reactive with antigens of the KS-associated human herpesvirus can be either competitive or noncompetitive binding assays. In competitive binding assays, the sample analyte competes with a labeled analyte for specific binding sites on a capture agent bound to a solid surface. Preferably the capture agent is a purified recombinant human herpesvirus protein produced as described above. Other sources of human herpesvirus proteins, including isolated or partially purified naturally occurring protein, may also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of the human herpesvirus antigens.

Hemagglutination Inhibition (HI) and Complement Fixation (CF) which are two laboratory tests that can be used to detect infection with human herpesvirus by testing for the presence of antibodies against the virus or antigens of the virus.

Serological methods can be also be useful when one wishes to detect antibody to a specific variant. For example, one may wish to see how well a vaccine recipient has responded to the new variant. Alternatively, one may take serum from a patient to see which variant the patient responds to the best.

This invention provides an antagonist capable of blocking the expression of the peptide or polypeptide encoded by the isolated DNA molecule. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of the isolated DNA molecule with a nucleotide sequence as shown in FIG. 3A, FIG. 3B, FIG. 3C, FIG. 3D, FIG. 3E, FIG. 3F, FIG. 3G, FIG. 3H, FIG. 3I, FIG. 3J, FIG. 3K or FIG. 3L (SEQ ID NOs: 1–12).

This invention provides an antisense molecule capable of hybridizing to the isolated DNA molecule. In one embodiment the antisense molecule is DNA. In another embodiment the antisense molecule is RNA.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that MRNA with an antisense nucleic acid or cleaving it with a ribozyme.

Antisense nucleic acids are DNA or RNA molecules that are complementary to at least a portion of a specific MRNA molecule. In the cell, they hybridize to that MRNA, forming a double stranded molecule. The cell does not translate an MRNA in this double-stranded form. Therefore, antisense nucleic acids interfere with the expression of MRNA into protein. Oligomers of about fifteen nucleotides and molecules that hybridize to the AUG initiation codon are particularly efficient, since they are easy to synthesize and are likely to pose fewer problems than larger molecules upon introduction to cells.

This invention provides a transgenic nonhuman mammal which comprises at least a portion of the isolated DNA molecule introduced into the mammal at an embryonic stage. Methods of producing a transgenic nonhuman mammal are known to those skilled in the art.

This invention provides a cell line containing the isolated KS associated herpesvirus of the subject invention. In one embodiment the isolated DNA molecule is artificially introduced into the cell. Cell lines include, but are not limited to: fibroblasts, such as HFF, NIH/3T3; Epithelial cells, such as 5637; lymphocytes, such as FCB; T-cells, such as CCRF-CEM (ATCC CCL 119); B-cells, such as BJAB and Raji (ATCC CCL 86); and myeloid cells such as K562 (ATCC CCL 243); Vero cells and carcinoma cells. Methods of producing such cell lines are known to those skilled in the art. In one embodiment the isolated KS associated herpesvirus is introduced into a RCC-1 cell line.

III. IN VITRO DIAGNOSTIC ASSAYS FOR THE DETECTION OF KS

This invention provides a method of diagnosing Kaposi's sarcoma in a subject which comprises: (a) obtaining a nucleic acid molecule from a tumor lesion of the subject; (b) contacting the nucleic acid molecule with a labelled nucleic acid molecule of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

In one embodiment the DNA molecule from the tumor lesion is amplified before step (b). In another embodiment PCR is employed to amplify the nucleic acid molecule. Methods of amplifying nucleic acid molecules are known to those skilled in the art.

A person of ordinary skill in the art will be able to obtain appropriate DNA sample for diagnosing Kaposi's sarcoma in the subject. The DNA sample obtained by the above described method may be cleaved by restriction enzyme. The uses of restriction enzymes to cleave DNA and the conditions to perform such cleavage are well-known in the art.

In the above described methods, a size fractionation may be employed which is effected by a polyacrylamide gel. In one embodiment, the size fractionation is effected by an agarose gel. Further, transferring the DNA fragments into a solid matrix may be employed before a hybridization step. One example of such solid matrix is nitrocellulose paper.

This invention provides a method of diagnosing Kaposi's sarcoma in a subject which comprises: (a) obtaining a nucleic acid molecule from a suitable bodily fluid of the subject; (b) contacting the nucleic acid molecule with a labelled nucleic acid molecules of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

This invention provides a method of diagnosing a DNA virus in a subject, which comprises (a) obtaining a suitable bodily fluid sample from the subject, (b) contacting the suitable bodily fluid of the subject to a support having already bound thereto a Kaposi's sarcoma antibody, so as to bind the Kaposi's sarcoma antibody to a specific Kaposi's sarcoma antigen, (c) removing unbound bodily fluid from the support, and (d) determining the level of Kaposi's sarcoma antibody bound by the Kaposi's sarcoma antigen, thereby diagnosing the subject for Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto a Kaposi's sarcoma antigen, so as to bind Kaposi's sarcoma antigen to a specific Kaposi's sarcoma antibody, (c) removing unbound bodily fluid from the support, and (d) determining the level of the Kaposi's sarcoma antigen bound by the Kaposi's sarcoma antibody, thereby diagnosing Kaposi's sarcoma.

This invention provides a method of detecting expression of a DNA virus associated with Kaposi's sarcoma in a cell which comprises obtaining total cDNA obtained from the cell, contacting the cDNA so obtained with a labelled DNA molecule under hybridizing conditions, determining the presence of cDNA hybridized to the molecule, and thereby detecting the expression of the DNA virus. In one embodiment mRNA is obtained from the cell to detect expression of the DNA virus.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the bodily fluid sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other methods are known to those skilled in the art. Further, a subject infected with a DNA virus associated with Kaposi's sarcoma may be diagnosed with the above described methods.

The detection of the human herpesvirus and the detection of virus-associated KS are essentially identical processes. The basic principle is to detect the virus using specific ligands that bind to the virus but not to other proteins or nucleic acids in a normal human cell or its environs. The ligands can either be nucleic acid or antibodies. The ligands can be naturally occurring or genetically or physically modified such as nucleic acids with non-natural or antibody derivatives, i.e., Fab or chimeric antibodies. Serological tests for detection of antibodies to the virus may also be performed by using protein antigens obtained from the human herpesvirus, and described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS is present.

A. Nucleic Acid Assays

The diagnostic assays of the invention can be nucleic acid assays such as nucleic acid hybridization assays and assays which detect amplification of specific nucleic acid to detect for a nucleic acid sequence of the human herpesvirus described herein.

Accepted means for conducting hybridization assays are known and general overviews of the technology can be had from a review of: *Nucleic Acid Hybridization: A Practical Approach* [72]; *Hybridization of Nucleic Acids Immobilized on Solid Supports* [41]; *Analytical Biochemistry* [4] and Innis et al., *PCR Protocols* [74], supra, all of which are incorporated by reference herein.

If PCR is used in conjunction with nucleic acid hybridization, primers are designed to target a specific portion of the nucleic acid of the herpesvirus. For example, the primers set forth in SEQ. ID NOs: 10–12 may be used to target detection of regions of the herpesvirus genome encoding ORF 25 homologue—ORF 32 homologue. From the information provided herein, those of skill in the art will be able to select appropriate specific primers.

Target specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of the human herpesvirus of the invention, nucleic acid probes are about 50 to about 1000 nucleotides, most preferably about 200 to about 400 nucleotides.

A sequence is "specific" for a target organism of interest if it includes a nucleic acid sequence which when detected is determinative of the presence of the organism in the presence of a heterogeneous population of proteins and other biologics. A specific nucleic acid probe is targeted to that portion of the sequence which is determinative of the organism and will not hybridize to other sequences especially those of the host where a pathogen is being detected.

The specific nucleic acid probe can be RNA or DNA polynucleotide or oligonucleotide, or their analogs. The probes may be single or double stranded nucleotides. The probes of the invention may be synthesized enzymatically, using methods well known in the art (e.g., nick translation, primer extension, reverse transcription, the polymerase chain reaction, and others) or chemically (e.g., by methods such as the phosphoramidite method described by Beaucage and Carruthers [19], or by the triester method according to Matteucci, et al. [62], both incorporated herein by reference).

The probe must be of sufficient length to be able to form a stable duplex with its target nucleic acid in the sample, i.e., at least about 14 nucleotides, and may be longer (e.g., at least about 50 or 100 bases in length). Often the probe will be more than about 100 bases in length. For example, when probe is prepared by nick-translation of DNA in the presence of labeled nucleotides the average probe length may be about 100–600 bases.

As noted above, the probe will be capable of specific hybridization to a specific KS-associated herpes virus nucleic acid. Such "specific hybridization" occurs when a probe hybridizes to a target nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, [81], supra, Ausubel, F., et al. [8] [hereinafter referred to as Sambrook], Methods in Enzymology [67] or *Hybridization with Nucleic Acid Probes* [42] all of which are incorporated herein by reference.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

A probe can be identified as capable of hybridizing specifically to its target nucleic acid by hybridizing the probe to a sample treated according the protocol of this invention where the sample contains both target virus and animal cells (e.g., nerve cells). A probe is specific if the probe's characteristic signal is associated with the herpesvirus DNA in the sample and not generally with the DNA of the host cells and non-biological materials (e.g., substrate) in a sample.

The following stringent hybridization and washing conditions will be adequate to distinguish a specific probe (e.g., a fluorescently labeled DNA probe) from a probe that is not specific: incubation of the probe with the sample for 12 hours at 37° C. in a solution containing denatured probe, 50% formamide, 2× SSC, and 0.1% (w/v) dextran sulfate, followed by washing in 1× SSC at 70° C. for 5 minutes; 2× SSC at 37° C. for 5 minutes; 0.2× SSC at room temperature for 5 minutes, and $H_2O$ at room temperature for 5 minutes. Those of skill will be aware that it will often be advantageous in nucleic acid hybridizations (i.e., in situ, Southern, or other) to include detergents (e.g., sodium dodecyl sulfate), chelating agents (e.g., EDTA) or other reagents (e.g., buffers, Denhardt's solution, dextran sulfate) in the hybridization or wash solutions. To test the specificity of the virus specific probes, the probes can be tested on host cells containing the KS-associated herpesvirus and compared with the results from cells containing non-KS-assocated virus.

It will be apparent to those of ordinary skill in the art that a convenient method for determining whether a probe is specific for a KS-associated viral nucleic acid utilizes a Southern blot (or Dot blot) using DNA prepared from one or more KS-associated human herpesviruses of the invention. Briefly, to identify a target specific probe DNA is isolated from the virus. Test DNA either viral or cellular is transferred to a solid (e.g., charged nylon) matrix. The probes are labelled following conventional methods. Following denaturation and/or prehybridization steps known in the art, the probe is hybridized to the immobilized DNAs under stringent conditions. Stringent hybridization conditions will depend on the probe used and can be estimated from the calculated $T_m$ (melting temperature) of the hybridized probe (see, e.g., Sambrook for a description of calculation of the $T_m$). For radioactively-labeled DNA or RNA probes an example of stringent hybridization conditions is hybridization in a solution containing denatured probe and 5× SSC at 65° C. for 8–24 hours followed by washes in 0.1× SSC, 0.1% SDS (sodium dodecyl sulfate) at 50–65° C. In general, the temperature and salt concentration are chosen so that the post hybridization wash occurs at a temperature that is about 5° C. below the $T_M$ of the hybrid. Thus for a particular salt concentration the temperature may be selected that is 5° C. below the $T_M$ or conversely, for a particular temperature, the salt concentration is chosen to provide a $T_M$ for the hybrid that is 5° C. warmer than the wash temperature. Following stringent hybridization and washing, a probe that hybridizes to the KS-associated viral DNA but not to the non-KS associated viral DNA, as evidenced by the presence of a signal associated with the appropriate target and the absence of a signal from the non-target nucleic acids, is identified as specific for the KS associated virus. It is further appreciated that in determining probe specificity and in utilizing the method of this invention to detect KS-associated herpesvirus, a certain amount of background signal is typical and can easily be distinguished by one of skill from a specific signal. Two fold signal over background is acceptable.

A preferred method for detecting the KS-associated herpesvirus is the use of PCR and/or dot blot hybridization. The presence or absence of an KS agent for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer may be used for the detection of message in samples of RNA or reverse transcriptase PCR and cDNA can be detected by methods described above. This procedure is also well known in the art. See [81] incorporated by reference herein.

An alternative means for determining the presence of the human herpesvirus is in situ hybridization, or more recently, in situ polymerase chain reaction. In situ PCR is described in Neuvo et al. [71], Intracellular localization of polymerase chain reaction (PCR)-amplified Hepatitis C cDNA; Bagasra et al. [10], Detection of Human Immunodeficiency virus type 1 provirus in mononuclear cells by in situ polymerase chain reaction; and Heniford et al. [35], Variation in cellular EGF receptor mRNA expression demonstrated by in situ reverse transcriptase polymerase chain reaction. In situ hybridization assays are well known and are generally described in *Methods Enzymol.* [67] incorporated by reference herein. In an in situ hybridization, cells are fixed to a solid support, typically a glass slide. The cells are then contacted with a hybridization solution at a moderate temperature to permit annealing of target-specific probes that are labelled. The probes are preferably labelled with radioisotopes or fluorescent reporters.

The above described probes are also useful for in-situ hybridization or in order to locate tissues which express this gene, or for other hybridization assays for the presence of this gene or its MRNA in various biological tissues. In-situ hybridization is a sensitive localization method which is not dependent on expression of antigens or native vs. denatured conditions.

Oligonucleotide (oligo) probes, synthetic oligonucleotide probes or riboprobes made from KSHV phagemids/plasmids, are relatively homogeneous reagents and successful hybridization conditions in tissue sections is readily transferable from one probe to another. Commercially synthesized oligonucleotide probes are prepared against the identified genes. These probes are chosen for length (45–65 mers), high G-C content (50–70%) and are screened for uniqueness against other viral sequences in GenBank.

Oligonucleotides are 3'end-labeled with [α-$^{35}$S]dATP to specific activities in the range of $1 \times 10^{10}$ dpm/ug using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 μm intervals and thawed onto 3-aminopropyltriethoxysilane treated slides and allowed to air dry. The slides are then be fixed in 4% freshly prepared paraformaldehyde, rinsed in water. Formalin-fixed, paraffin embedded KS tissues cut at 6 μm and baked onto glass slides can also be used. The sections are then deparaffinized in xylenes and rehydrated through graded alcohols. Prehybridization in 20 mM Tris Ph 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (Ph 7.4), 3x SSC, 1x Denhardt's solution, 100 ug/ml salmon sperm DNA, 125 ug/ml yeast tRNA and the oligo probe ($10^6$ cpm/ml) at 42° C. overnight. The slides are washed twice with 2x SSC and twice with 1x SSC for 15 minutes each at room temperature and visualized by autoradiography. Briefly, sections are dehydrated through graded alcohols containing 0.3M ammonium acetate and air dried. The slides are dipped in Kodak NTB2 emulsion, exposed for days to weeks, developed, and counterstained with hematoxylin and eoxin. Alternative immunohistochemical protocols may be employed which are known to those skilled in the art.

IV. TREATMENT OF HUMAN HERPESVIRUS-INDUCED KS

This invention provides a method of treating a subject with Kaposi's sarcoma, comprising administering to the subject an effective amount of the antisense molecule capable of hybridizing to the isolated DNA molecule under conditions such that the antisense molecule selectively enters a tumor cell of the subject, so as to treat the subject.

This invention provides a method for treating a subject with Kaposi's sarcoma (KS) comprising administering to the subject having a human herpesvirus-associated KS a pharmaceutically effective amount of an antiviral agent in a pharmaceutically acceptable carrier, wherein the agent is effective to treat the subject with KS-associated human herpes virus.

Further, this invention provides a method of prophylaxis or treatment for Kaposi's sarcoma (KS) by administering to a patient at risk for KS, an antibody that binds to the human herpesvirus in a pharmaceutically acceptable carrier. In one embodiment the antiviral drug is used to treat a subject with the DNA herpesvirus of the subject invention.

The use of combinations of antiviral drugs and sequential treatments are useful for treatment of herpesvirus infections and will also be useful for the treatment of herpesvirus-induced KS. For example, Snoeck et al. [88], found additive or synergistic effects against CMV when combining anti-herpes drugs (e.g., combinations of zidovudine [3'-azido-3'-deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbonyl)-thiocarbonohydrazone is described in U.S. Pat. No. 5,175, 165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. [56].

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. [11]) describes the use of thymilydate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophalactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach, S. L., et al. [28]) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

A. Antiviral Agents

The antiherpesvirus agents that will be useful for treating virus-induced KS can be grouped into broad classes based on their presumed modes of action. These classes include agents that act (i) by inhibition of viral DNA polymerase, (ii) by targeting other viral enzymes and proteins, (iii) by miscellaneous or incompletely understood mechanisms, or (iv) by binding a target nucleic acid (i.e., inhibitory nucleic acid therapeutics). Antiviral agents may also be used in combination (i.e., together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of Viral DNA Polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside analogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al. [11]).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al. [95]) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq [22] and in other references cited supra and infra, all of which are incorporated by reference herein.

Anti-herpesvirus medications suitable for treating viral induced KS include, but are not limited to, nucleoside analogs including acyclic nucleoside phosphonate analogs (e.g., phosphonylmethoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1-β-D-arabinofuranosylcytosine (ara-C); HPMPC [(S)-1-[3-hydroxy-2-(phosphonylmethoxy)propyl[cytosine (e.g., GS 504 Gilead Science)] and its cyclic form (cHPMPC); HPMPA [(S)-9-(3-hydroxy-2-phosphonylmethoxypropyl)adenine] and its cyclic form (cHPMPA); (S)-HPMPDAP [(S)-9-(3-hydroxy-2-phosphonylmethoxypropyl)-2,6-diaminopurine]; PMEDAP [9-(2-phosphonyl-methoxyethyl)-2,6-diaminopurine]; HOE 602 [2-amino-9-(1,3-bis(isopropoxy)-2-propoxymethyl)purine]; PMEA [9-(2-phosphonylmethoxyethyl)adenine]; bromovinyldeoxyuridine (Burns and Sandford. [21]); 1-β-D-arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E)-5-(2-iodovinyl)-2'-deoxyuridine] and its carbocyclic analogue, C-IVDU (Balzarini et al. [11])]; and 5-mercutithio analogs of 2'-deoxyuridine (Holliday, J., and Williams, M. V. [38]); acyclovir [9-([2-hydroxyethoxy]methyl)guanine; e.g., Zovirax (Burroughs Wellcome)]; penciclovir (9-[4-hydroxy-2-(hydroxymethyl)butyl]-guanine); ganciclovir [(9-[1,3-dihydroxy-2 propoxymethyl]-guanine) e.g., Cymevene, Cytovene (Syntex), DHPG (Stals et al. [89]]; isopropylether derivatives of ganciclovir (see, e.g., Winkelmann et al. [94]); cygalovir; famciclovir [2-amino-9-(4-acetoxy-3-(acetoxymethyl)but-1-yl)purine (Smithkline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclobutane ring (e.g., cyclobut-A [(+-)-9-[1β,2α,3β)-2,3-bis(hydroxymethyl)-1-cyclobutyl]adenine], cyclobut-G [(+-)-9-[1β,2α,3β)-2,3-bis(hydroxymethyl)-1-cyclobutyl]guanine], BHCG [(R)-(1α,2β,1α)-9-(2,3-bis(hydroxymethyl)cyclobutyl]guanine), and an active isomer of racemic BHCG, SQ 34,514 [1R-1α,2β,3α)-2-amino-9-[2,3-bis(hydroxymethyl)cyclobutyl]-6H-purin-6-one (see, Braitman et al.(1991) [20]]. Certain of these antiherpesviral agents are discussed in Gorach et al. [28]; Saunders et al. [82]; Yamanaka et al., [96]; Greenspan et al. [29], all of which are incorporated by reference herein.

Triciribine and triciribine monophosphate are potent inhibitors against herpes viruses. (Ickes et al. [43], incorporated by reference herein), HIV-1 and HIV-2 (Kucera et al. [51], incorporated by reference herein) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain terminator by the viral DNA polymerase during viral replication. It has therapeutic activity against a broad range of herpesviruses, Herpes simplex Types 1 and 2, Varicella-Zoster, Cytomegalovirus, and Epstein-Barr Virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble [73]. Treatment protocols for ganciclovir are 5 mg/kg twice a day IV or 2.5 mg/kg three times a day for 10–14 days. Maintenance doses are 5–6 mg/kg for 5–7 days.

Also of interest is HPMPC. HPMPC is reported to be more active than either acyclovir or ganciclovir in the chemotherapy and prophylaxis of various HSV-1, HSV-2, TK-HSV, VZV or CMV infections in animal models ([22], supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g., FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2'-deoxyuridine derivatives, e.g., BTDU [5-5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythro-oxetanosyl)guanine]. Although OXT-G is believed to act by inhibiting viral DNA synthesis its mechanism of action has not yet been elucidated. These and other compounds are described in Andrei et al. [5] which is incorporated by reference herein. Additional antiviral purine derivatives useful in treating herpesvirus infections are disclosed in U.S. Pat. No. 5,108,994 (assigned to Beecham Group P.L.C.). 6-Methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Agents That Target Viral Proteins Other Than DNA Polymerase or Other Viral Functions Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target of, e.g., 1-[2-(hydroxymethyl) cylcoalkylmethyl]-5-substituted -uracils and -guanines as described in, e.g., U.S. Pat. Nos. 4,863,927 and 4,782,062 (Tolman et al.; Merck)) as well as other enzymes. It will be apparent to one of ordinary skill in the art that there are additional viral proteins, both characterized and as yet to be discovered, that can serve as target for antiviral agents.

iv) Other Agents and Modes of Antiviral Action

Kutapressin is a liver derivative available from Schwarz Parma of Milwaukee, Wis. in an injectable form of 25 mg/ml. The recommended dosage for herpesviruses is from 200 to 25 mg/ml per day for an average adult of 150 pounds.

Poly(I)-Poly($C_{12}$U), an accepted antiviral drug known as Ampligen from HEM Pharmaceuticals of Rockville, Md. has been shown to inhibit herpesviruses and is another antiviral agent suitable for treating KS. Intravenous injection is the preferred route of administration. Dosages from about 100 to 600 mg/m$^2$ are administered two to three times weekly to adults averaging 150 pounds. It is best to administer at least 200 mg/m$^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A,79296 and A,73209 (Abbott) for varicella zoster, and Compound 882C87 (Burroughs Wellcome) [see, The Pink Sheet 55(20) May 17, 1993].

Interferon is known inhibit replication of herpes viruses. See [73], supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9-(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894,458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiherpes viral agents. U.S. Pat. No. 5,306,722 (Kim et al.; Bristol-Meyers Squibb) describes thymidine kinase inhibitors useful for treating HSV infections and for inhibiting herpes thymidine kinase. Other anitherpesvirus compositions are described in U.S. Pat. Nos. 5,286,649 and 5,098,708 (Konishi et al., Bristol-Meyers Squibb) and U.S. Pat. No. 5,175,165 (Blumenkopf et al.; Burroughs Wellcome). U.S. Pat. No. 4,880,820 (Ashton et al.; Merck) describes the antiherpes virus agent (S)-9-(2,3-dihydroxy-1-propoxymethyl)guanine.

U.S. Pat. No. 4,708,935 (Suhadolnik et al.; Research Corporation) describes a 3'-deoxyadenosine compound effective in inhibiting HSV and EBV. U.S. Pat. No. 4,386,076 (Machida et al.; Yamasa Shoyu Kabushiki Kaisha) describes use of (E)-5-(2-halogenovinyl)-arabinofuranosyluracil as an antiherpesvirus agent. U.S. Pat.

No. 4,340,599 (Lieb et al.; Bayer Aktiengesellschaft) describes phosphonohydroxyacetic acid derivatives useful as antiheroes agents. U.S. Pat. Nos. 4,093,715 and 4,093,716 (Lin et al. Research Corporation) describe 5'-amino-5'-deoxythymidine and 5-iodo-5'-amino-2',5'-dideoxycytidine as potent inhibitors of herpes simplex virus. U.S. Pat. No. 4,069,382 (Baker et al.; Parke, Davis & Company) describes 9-(5-O-Acyl-beta-D-arabinofuranosyl)adenine compounds useful as antiviral agents. U.S. Pat. No. 3,927,216 (Witkowski et al.) describes the use of 1,2,4-triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein Barr virus.

v) Inhibitory Nucleic Acid Therapeutics

Also contemplated here are inhibitory nucleic acid therapeutics which can inhibit the activity of herpesviruses in patients with KS. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene, C. and Toulme, J. [34], which is hereby incorporated by reference and is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al. [93] and Harel-Bellan, A., et al. [31A]. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

This invention relates to the targeting of inhibitory nucleic acids to sequences the human herpesvirus of the invention for use in treating KS. An example of an antiherpes virus inhibitory nucleic acid is ISIS 2922 (ISIS Pharmaceuticals) which has activity against CMV [see, *Biotechnology News* 14(14) p. 5].

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

iii) Administration

The subjects to be treated or whose tissue may be used herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. IMMUNOLOGICAL APPROACHES TO THERAPY

Having identified a primary causal agent of KS in humans as a novel human herpesvirus, there are immunosuppressive therapies that can modulate the immunologic dysfunction that arises from the presence of viral infected tissue. In particular, agents that block the immunological attack of the viral infected cells will ameliorate the symptoms of KS and/or reduce the disease progress. Such therapies include antibodies that specifically block the targeting of viral infected cells. Such agents include antibodies which bind to cytokines that upregulate the immune system to target viral infected cells.

The antibody may be administered to a patient either singly or in a cocktail containing two or more antibodies, other therapeutic agents, compositions, or the like, including, but not limited to, immuno-suppressive agents, potentiators and side-effect relieving agents. Of particular interest are immuno-suppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference,* 41st Ed. (1987), Publisher Edward R. Barnhart, N.J.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. VACCINES AND PROPHYLAXIS FOR KS

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administering to the subject in an effective amount to vaccinate a subject against Kaposi's sarcoma.

This invention provides a method of immunizing a subject against a disease caused by the DNA herpesvirus associated with Kaposi's sarcoma which comprises administering to the subject an effective immunizing dose of the isolated herpesvirus vaccine.

A. Vaccines

The invention also provides substances suitable for use as vaccines for the prevention of KS and methods for administering them. The vaccines are directed against the human herpesvirus of the invention, and most preferably comprise antigen obtained from the KS-associated human herpesvirus.

Vaccines can be made recombinantly. Typically, a vaccine will include from about 1 to about 50 micrograms of antigen or antigenic protein or peptide. More preferably, the amount of protein is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049 which is incorporated by reference herein. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional crosslinkers as binding agents as detailed, for example, by Means and Feeney, "A recent review of protein modification techniques," Bioconjugate Chem. 1:2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocomprised and normal children (Hardy, I., et al. [30]; Hardy, I. et al. [31]; Levin, M. J. et al. [54]; Gershon, A. A. [26]. Vaccines against Herpes simplex Types 1 and 2 are also commercially available with some success in protection against primary disease, but have been less successful in preventing the establishment of latent infection in sensory ganglia (Roizman, B. [78]; Skinner, G. R. et al. [87]).

Vaccines against the human herpesvirus can be made by isolating extracellular viral particles from infected cell cultures, inactivating the virus with formaldehyde followed by ultracentrifugation to concentrate the viral particles and remove the formaldehyde, and immunizing individuals with 2 or 3 doses containing $1 \times 10^9$ virus particles (Skinner, G. R. et al. [86]). Alternatively, envelope glycoproteins can be expressed in E. coli or transfected into stable mammalian cell lines, the proteins can be purified and used for vaccination (Lasky, L. A. [53]). MHC—binding peptides from cells infected with the human herpesvirus can be identified for vaccine candidates per the methodology of [61], supra.

The antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lidid X, Corynebacterium parvum (Propionibacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 µg to about 100 µg protein per patient. A preferable range is from about 1 µg to about 50 µg per dose. A more preferred range is about 15 µg to about 45 µg. A suitable dose size is about 0.5 ml. Accordingly, a dose for intramuscular injection, for example, would comprise 0.5 ml containing 45 µg of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral proteins from the human herpesvirus. For example, it is known in the protein art that certain amino acid residues can be substituted with amino acids of similar size and polarity without an undue effect upon the biological activity of the protein. The human hepresvirus proteins have significant tertiary structure and the epitopes are usually conformational. Thus, modifications should generally preserve conformation to produce a protective immune response.

B. Antibody Prophylaxis

Therapeutic, intravenous, polyclonal or monoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-1, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

C. Monitoring therapeutic efficacy

This invention provides a method for monitoring the therapeutic efficacy of treatment for Kaposi's sarcoma, which comprises determining in a first sample from a subject with Kaposi's sarcoma the presence of the isolated DNA molecule, administering to the subject a therapeutic amount of an agent such that the agent is contacted to the cell in a sample, determining after a suitable period of time the amount of the isolated DNA molecule in the second sample from the treated subject, and comparing the amount of isolated DNA molecule determined in the first sample with the amount determined in the second sample, a difference indicating the effectiveness of the agent, thereby monitoring the therapeutic efficacy of treatment for Kaposi's sarcoma. As defined herein "amount" is viral load or copy number. Methods of determining viral load or copy number are known to those skilled in the art.

VII. SCREENING ASSAYS FOR PHARMACEUTICAL AGENTS OF INTEREST IN ALLEVIATING THE SYMPTOMS OF KS

Since an agent involved in the causation or progression of KS has been identified and described here, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus proteins or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada, H. et al. [7]; Kikuta et al. [48] both incorporated by reference herein). Infected cultures and their supernatants can be assayed for the total amount of virus including the presence of the viral genome by quantitative PCR, by dot blot assays, or by using immunologic methods. For example, a culture of susceptible cells could be infected with the human herpesvirus in the presence of various concentrations of drug, fixed on slides after a period of days, and examined for viral antigen by indirect immunofluorescence with monoclonal antibodies to viral peptides ([48], supra. Alternatively, chemically adhered MT-4 cell monolayers can be used for an infectious agent assay using indirect immunofluorescent antibody staining to search for focus reduction (Higashi, K. et al. [36], incorporated by reference herein).

As an alternative to whole cell in vitro assays, purified enzymes isolated from the human herpesvirus can be used as targets for rational drug design to determine the effect of the potential drug on enzyme activity, such as thymidine phosphotransferase or DNA polymerase. The genes for these two enzymes are provided herein. A measure of enzyme activity indicates effect on the agent itself.

Drug screens using herpes viral products are known and have been previously described in EP 0514830 (herpes proteases) and WO 94/04920 ($U_L13$ gene product).

This invention provides an assay for screening anti-KS chemotherapeutics. Infected cells can be incubated in the presence of a chemical agent that is a potential chemotherapeutic against KS (e.g. acyclo-guanosine). The level of virus in the cells is then determined after several days by IFA for antigens or Southern blotting for viral genome or Northern blotting for MRNA and compared to control cells. This assay can quickly screen large numbers of chemical compounds that may be useful against KS.

Further, this invention provides an assay system that is employed to identify drugs or other molecules capable of binding to the DNA molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Experiment 1: Representational difference analysis (RDA) to identify and characterize unique DNA sequences in KS tissue To search for foreign DNA sequences belonging to an infectious agent in AIDS-KS, representational difference analysis (RDA) was employed to identify and characterize unique DNA sequences in KS tissue that are either absent or present in low copy number in non-diseased tissue obtained from the same patient [58]. This method can detect adenovirus genome added in single copy to human DNA but has not been used to identify previously uncultured infectious agents. RDA is performed by making simplified "representations" of genomes from diseased and normal tissues from the same individual through PCR amplification of short restriction fragments. The DNA representation from the diseased tissue is then ligated to a priming sequence and hybridized to an excess of unligated, normal tissue DNA representation. Only unique sequences found in the diseased tissue have priming sequences on both DNA strands and are preferentially amplified during subsequent rounds of PCR amplification. This process can be repeated using different ligated priming sequences to enrich the sample for unique DNA sequences that are only found in the tissue of interest.

DNA (10 μg) extracted from both the KS lesion and unaffected tissue were separately digested to completion with Bam HI (20 units/μg) at 37° C. for 2 hours and 2 μg of digestion fragments were ligated to NBam12 and NBam24 priming sequences [primer sequences described in 58]. Thirty cycles of PCR amplification were performed to amplify "representations" of both genomes. After construction of the genomic representations, KS tester amplicons between 150 and 1500 bp were isolated from an agarose gel and NBam priming sequences were removed by digestion with Bam HI. To search for unique DNA sequences not found in non-KS driver DNA, a second set of priming sequences (JBam12 and JBam24) was ligated onto only the KS tester DNA amplicons (FIG. 1, lane 1). 0.2 μg of ligated KS lesion amplicons were hybridized to 20 μg of unligated, normal tissue representational amplicons. An aliquot of the hybridization product was then subjected to 10 cycles of PCR amplification using JBam24, followed by mung bean nuclease digestion. An aliquot of the mung bean-treated difference product was then subjected to 15 more cycles of PCR with the JBam24 primer (FIG. 1, lane 2). Amplification products were redigested with Bam HI and 200 ng of the digested product was ligated to RBam12 and RBam24 primer sets for a second round of hybridization and PCR amplification (FIG. 1, lane 3). This enrichment procedure was repeated a third time using the JBam primer set (FIG. 1, lane 4). Both the original driver and the tester DNA samples (Table 2, Patient A) were subsequently found to contain the AIDS-KS specific sequences KS330Bam and KS627Bam indicating that RDA can be successfully employed when the target sequences are present in unequal copy number in both tissues.

The initial round of DNA amplification-hybridization from KS and normal tissue resulted in a diffuse banding pattern (FIG. 1, lane 2), but four bands at approximately 380, 450, 540 and 680 bp were identifiable after the second amplification-hybridization (FIG. 1, lane 3). These bands became discrete after a third round of amplification-hybridization (FIG. 1, lane 4) Control RDA, performed by hybridizing DNA extracted from AIDS-KS tissue against itself, produced a single band at approximately 540 bp (FIG. 1, lane 5). The four KS-associated bands (designated KS330Bam, KS390Bam, KS480Bam, KS627Bam after digestion of the two flanking 28 bp ligated priming sequences with Bam HI) were gel purified and cloned by insertion into the pCRII vector. PCR products were cloned in the pCRII vector using the TA cloning system (Invitrogen Corporation, San Diego, Calif.).

Experiment 2: Determination of the specificity of AIDS-KS unique sequences.

To determine the specificity of these sequences for AIDS-KS, random-primed $^{32}$P-labeled inserts were hybridized to Southern blots of DNA extracted from cryopreserved tissues obtained from patients with and without AIDS. All AIDS-KS specimens were examined microscopically for morphologic confirmation of KS and immunohistochemically for Factor VIII, Ulex europaeus and CD34 antigen expression. One of the AIDS-KS specimens was apparently mislabeled since KS tissue was not detected on microscopic examination but was included in the KS specimen group for purposes of statistical analysis. Control tissues used for comparison to the KS lesions included 56 lymphomas from patients with and without AIDS, 19 hyperplastic lymph nodes from patients with and without AIDS, 5 vascular tumors from nonAIDS patients and 13 tissues infected with opportunistic infections that commonly occur in AIDS patients. Control DNA was also extracted from a consecutive series of 49 surgical biopsy specimens from patients without AIDS. Additional clinical and demographic information on the specimens was not collected to preserve patient confidentiality.

The tissues, listed in Table 1, were collected from diagnostic biopsies and autopsies between 1983 and 1993 and stored at −70° C. Each tissue sample was from a different patient, except as noted in Table 1. Most of the 27 KS specimens were from lymph nodes dissected under surgical conditions which diminishes possible contamination with normal skin flora. All specimens were digested with Bam HI prior to hybridization.

KS390Bam and KS408Bam hybridized nonspecifically to both KS and non-KS tissues and were not further characterized. 20 of 27 (74%) AIDS-KS DNAs hybridized with variable intensity to both KS330Bam and KS627Bam, and one additional KS specimen hybridized only to KS627Bam by Southern blotting (FIG. 2 and Table 1). In contrast to AIDS-KS lesions, only 6 of 39 (15%) non-KS tissues from patients with AIDS hybridized to the KS330Bam and KS627Bam inserts (Table 1).

Specific hybridization did not occur with lymphoma or lymph node DNA from 36 persons without AIDS or with control DNA from 49 tissue biopsy specimens obtained from a consecutive series of patients. DNA extracted from several vascular tumors, including a hemangiopericytoma, two angiosarcomas and a lymphangioma, were also negative by Southern blot hybridization. DNA extracted from tissues with opportunistic infections common to AIDS patients, including 7 acid-fast bacillus (undetermined species), 1 cytomegalovirus, 1 cat-scratch bacillus, 2 cryptococcus and 1 toxoplasmosis infected tissues, were negative by Southern blot hybridization to KS330Bam and KS627Bam (Table 1).

TABLE 1

Southern blot hybridization for KS330Bam and KS627Bam and PCR amplification for KS330$_{234}$ in human tissues from individual patients.

| Tissue | n | KS330Bam Southern hybridization n(%) | KS627Bam Southern hybridization n(%) | KS330$_{234}$ PCR positive |
|---|---|---|---|---|
| AIDS-KS | 27* | 20 (74) | 21 (78) | 25 (93) |
| AIDS lymphomas | 27† | 3 (11) | 3 (11) | 3 (11) |
| AIDS lymph nodes | 12‡ | 3 (25) | 3 (25) | 3 (25) |
| Non-AIDS Lymphomas | 29 | 0 (0) | 0 (0) | 0 (0) |
| Non-AIDS lymph nodes | 7 | 0 (0) | 0 (0) | 0 (0) |
| Vascular tumors | 4§ | 0 (0) | 0 (0) | 0 (0) |
| Opportunistic infections | 13Π | 0 (0) | 0 (0) | 0 (0) |
| Consecutive surgical biopsies | 49¶** | 0 (0) | 0 (0) | 0 (0) |

Legend to Table 1:
*Includes one AIDS-KS specimen unamplifiable for p53 exon 6 and one tissue which on microscopic examination did not have any detectable KS tissue present. Both of these samples were negative by Southern blot hybridization to KS330Bam and KS627Bam and by PCR amplification for the KS330$_{234}$ amplicon.
†Includes 7 small non-cleaved cell lymphomas, 20 diffuse large cell and immunoblastic lymphomas. Three of the lymphomas with immunoblastic morphology were positive for KS330Bam and KS627Bam.
‡Includes 13 anaplastic large cell lymphomas, 4 diffuse large cell lymphomas, 4 small lymphocytic lymphomas/chronic lymphocytic leukemias, 3 hairy cell leukemias, 2 monocytoid B-cell lymphomas, 1 follicular small cleaved cell lymphoma, 1 Burkitt's lymphoma, 1 plasmacytoma.
§Includes 2 angiosarcomas, 1 hemangiopericytoma and 1 lymphangioma.
ΠIncludes 2 cryptococcus, 1 toxoplasmosis, 1 cat-scratch bacillus, 1 cytomegalovirus, 1 Epstein-Barr virus, and 7 acid-fast bacillus infected tissues. In addition, pure cultures of Mycobacterium avium-complex were negative by Southern hybridization and PCR, and pure cultures of Mycoplasma penetrans were negative by PCR.
¶Tissues included skin, appendix, kidney, prostate, hernia sac, lung, fibrous tissue, gallbladder, colon, foreskin, thyroid, small bowel, adenoid, vein, axillary tissue, lipoma, heart, mouth, hemorrhoid, pseudoaneurysm and fistula track. Tissues were collected from a consecutive series of biopsies on patients without AIDS but with unknown HIV serostatus.

TABLE 1-continued

Southern blot hybridization for KS330Bam and KS627Bam and PCR amplification for KS330$_{234}$ in human tissues from individual patients.

| Tissue | n | KS330Bam Southern hybridization n(%) | KS627Bam Southern hybridization n(%) | KS330$_{234}$ PCR positive |
|---|---|---|---|---|

**Apparent nonspecific hybridization at approximately 20 Kb occurred in 4 consecutive surgical biopsy DNA samples: one colon and one hernia sac DNA sample hybridized to KS330Bam alone, another hernia sac DNA sample hybridized to KS627Bam alone and one appendix DNA sample hybridized to both KS330Bam and KS627Bam. These samples did not hybridize in the 330–630 bp range expected for these sequences and were PCR negative for KS330$_{234}$.

In addition, DNA from Epstein-Barr virus-infected peripheral blood lymphocytes and pure cultures of Mycobacterium avium-complex were also negative by Southern hybridization. Overall, 20 of 27 (74%) AIDS-KS specimens hybridized to KS330Bam and 21 of 27 (78%) AIDS-KS specimens hybridized to KS627Bam, compared to only 6 of 142 (4%) non-KS human DNA control specimens ($\chi^2$= 85.02, $p<10^{-7}$ and $\chi^2$=92.4, $p<10^{-7}$ respectively).

Figure 2A:
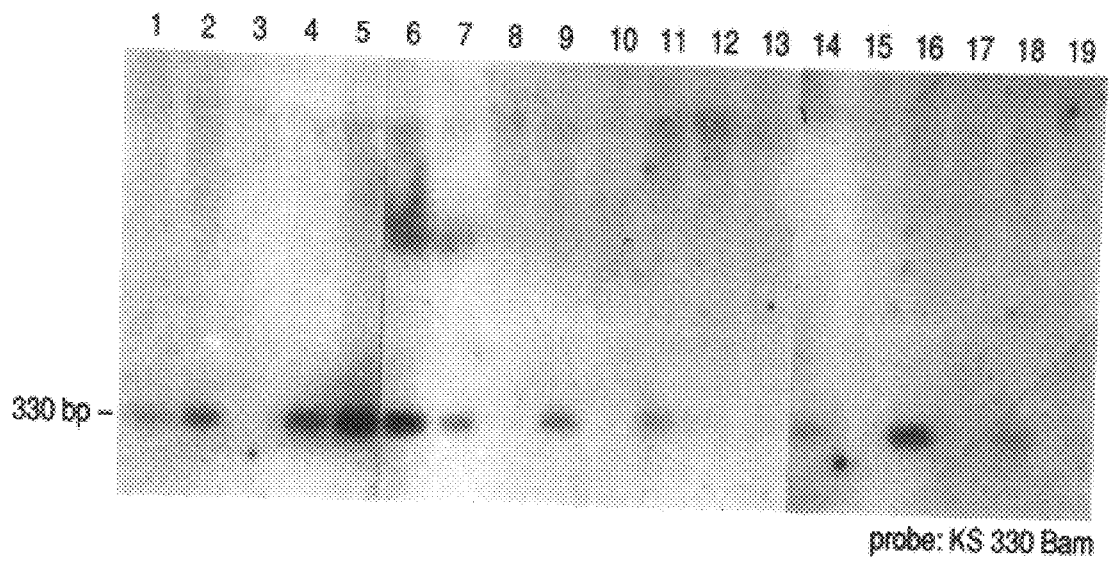
FIGS. 2A–2B: Hybridization of $^{32}$P-labelled KS330Bam (FIG. 2A) and KS627Bam (FIG. 2B) sequences to a representative panel of 19 DNA samples extracted from KS lesions and digested with Bam HI. KS330Bam hybridized to 11 of the 19 and KS627Bam hybridized to 12 of the 19 DNA samples from AIDS-KS lesions. Two additional cases (lanes 12 and 13) were shown to have faint bands with both KS330Bam and KS627Bam probes after longer exposure. One negative specimen (lane 3) did not have microscopically detectable KS in the tissue specimen. Seven of 8 additional KS DNA samples also hybridized to both sequences.
Figure 2B:
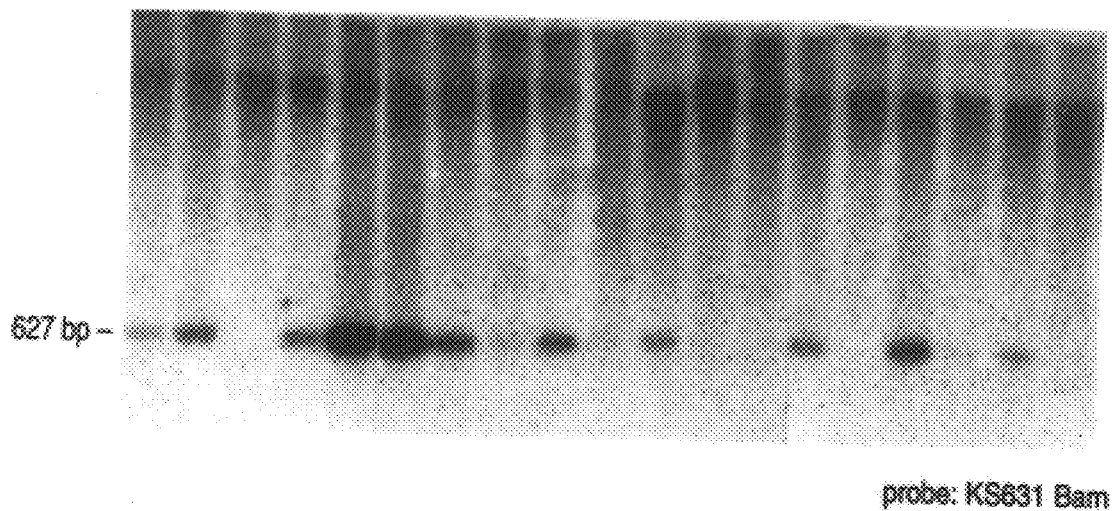

The sequence copy number in the AIDS-KS tissues was estimated by simultaneous hybridization with KS330Bam and a 440 bp probe for the constant region of the T cell receptor β gene [76]. Samples in lanes 5 and 6 of FIGS. 2A–2B showed similar intensities for the two probes indicating an average copy number of approximately two KS330Bam sequences per cell, while remaining tissues had weaker hybridization signals for the KS330Bam probe.

Experiment 3: Characterization of KS330Bam and KS627Bam

To further characterize KS330Bam and KS627Bam, six clones for each insert were sequenced. The Sequenase version 2.0 (United States Biochemical, Cleveland, Ohio) system was used and sequencing was performed according to manufacturer's instructions. Nucleotides sequences were confirmed with an Applied Biosystems 373A Sequencer in the DNA Sequencing Facilities at Columbia University.

KS330Bam is a 330 bp sequence with 51% G:C content (FIG. 3B) and KS627Bam is a 627 bp sequence with a 63% G:C content (FIG. 3C). KS330Bam has 54% nucleotide identity to the BDLF1 open reading frame (ORF) of Epstein-Barr virus (EBV). Further analysis revealed that both KS330Bam and KS627Bam code for amino acid sequences with homology to polypeptides of viral origin. SwissProt and PIR protein databases were searched for homologous ORF using BLASTX [3].

KS330Bam is 51% identical by amino acid homology to a portion of the ORF26 open reading frame encoding the capsid protein VP23 (NCBI g.i. 60348, bp 46024–46935) of herpesvirus saimiri [2], a gammaherpesvirus which causes fulminant lymphoma in New world monkeys. This fragment also has a 39% identical amino acid sequence to the theoretical protein encoded by the homologous open reading frame BDLF1 in EBV (NCBI g.i. 59140, bp 132403–133307) [9]. The amino acid sequence encoded by KS627Bam is homologous with weaker identity (31%) to the tegument protein, gp140 (ORF 29, NCBI g.i. 60396, bp108782–112681) of herpesvirus saimiri.

Sequence data from KS330Bam was used to construct PCR primers to amplify a 234bp fragment designated KS330$_{234}$ (FIG. 3B). The conditions for PCR analyses were as follows: 94° C. for 2 min (1 cycle); 94° C. for 1 min, 58° C. for 1 min, 72° C. for 1 min (35 cycles) ; 72° C. extension for 5 min (1 cycle). Each PCR reaction used 0.1 μg of genomic DNA, 50 pmoles of each primer, 1 unit of Taq polymerase, 100 μM of each deoxynucleotide triphosphate, 50 mM KCl, 10 mM Tris-HCl (pH 9.0), and 0.1% Triton-X-100 in a final volume of 25 μl. Amplifications were carried out in a Perkin-Elmer 480 Thermocycler with 1-s ramp times between steps.

Although Southern blot hybridization detected the KS330Bam sequence in only 20 of 27 KS tissues, 25 of the 27 tissues were positive by PCR amplification for $KS330_{234}$ (FIGS. 4A–4B) demonstrating that KS330Bam is present in some KS lesions at levels below the threshold for detection by Southern blot hybridization. All $KS330_{234}$ PCR products hybridized to a $^{32}P$ end-labelled 25 bp internal oligomer, confirming the specificity of the PCR (FIG. 4B). Of the two AIDS-KS specimens negative for $KS330_{234}$, both specimens appeared to be negative for technical reasons: one had no microscopically detectable KS tissue in the frozen sample (FIGS. 4A–4B, lane 3), and the other (FIGS. 4A–4B, lane 15) was negative in the control PCR amplification for the p53 gene indicating either DNA degradation or the presence of PCR inhibitors in the sample. PCR amplification of the p53 tumor suppressor gene was used as a control for DNA quality. Sequences of p53 primers from P6-5, 5'-ACAGGGCTGGTTGCCCAGGGT-3' (SEQ ID No: 16); and P6-3. 5'-AGTTGCAAACCAGACCTCAG-3' (SEQ ID NO: 17) [25].

Except for the 6 control samples from AIDS patients that were also positive by Southern blot hybridization, none of the other 136 control specimens were positive by PCR for $KS330_{234}$. All of these specimens were amplifiable for the p53 gene, indicating that inadequate PCR amplification was not the reason for lack of detection of $KS330_{234}$ in the control tissues. Samples containing DNA from two candidate KS agents, EBV and Mycoplasma penetrans (ATCC Accession No. 55252), a pathogen commonly found in the genital tract of patients with AIDS-KS [59] were also negative for amplification of $KS330_{234}$. In addition, several KS specimens were tested using commercial PCR primers (Stratagene, La Jolla, Calif.) specific for mycoplasmata and primers specific for the EBNA-2, EBNA-3C and EBER regions of EBV and were negative [57].

Overall, DNA from 25 (93%) of 27 AIDS-KS tissues were positive by PCR compared with DNA from 6 (4%) of 142 control tissues, including 6 (15%) of 39 non-KS lymph nodes and lymphomas from AIDS patients ($\chi^2=38.2$, $p<10^{-6}$), 0 of 36 lymph nodes and lymphomas from non-AIDS patients ($\chi^2=55.2$, $p<10^{-7}$) and 0 of 49 consecutive biopsy specimens ($\chi^2=67.7$, $p<10^{-7}$). Thus, $KS330_{234}$ was found in all 25 amplifiable tissues with microscopically detectable AIDS-KS, but rarely occurred in non-KS tissues, including tissues from AIDS patients.

Of the six control tissues from AIDS patients that were positive by both PCR and Southern hybridization, two patients had KS elsewhere, two did not develop KS and complete clinical histories for the remaining two patients were unobtainable. Three of the six positive non-KS tissues were lymph nodes with follicular hyperplasia taken from patients with AIDS. Given the high prevalence of KS among patients with AIDS, it is possible that undetected microscopic foci of KS were present in these lymph nodes. The other three positive tissue specimens were B cell immunoblastic lymphomas from AIDS patients. It is possible that the putative KS agent is also a cofactor for a subset of AIDS-associated lymphomas [16, 17, 80].

Figure 5:
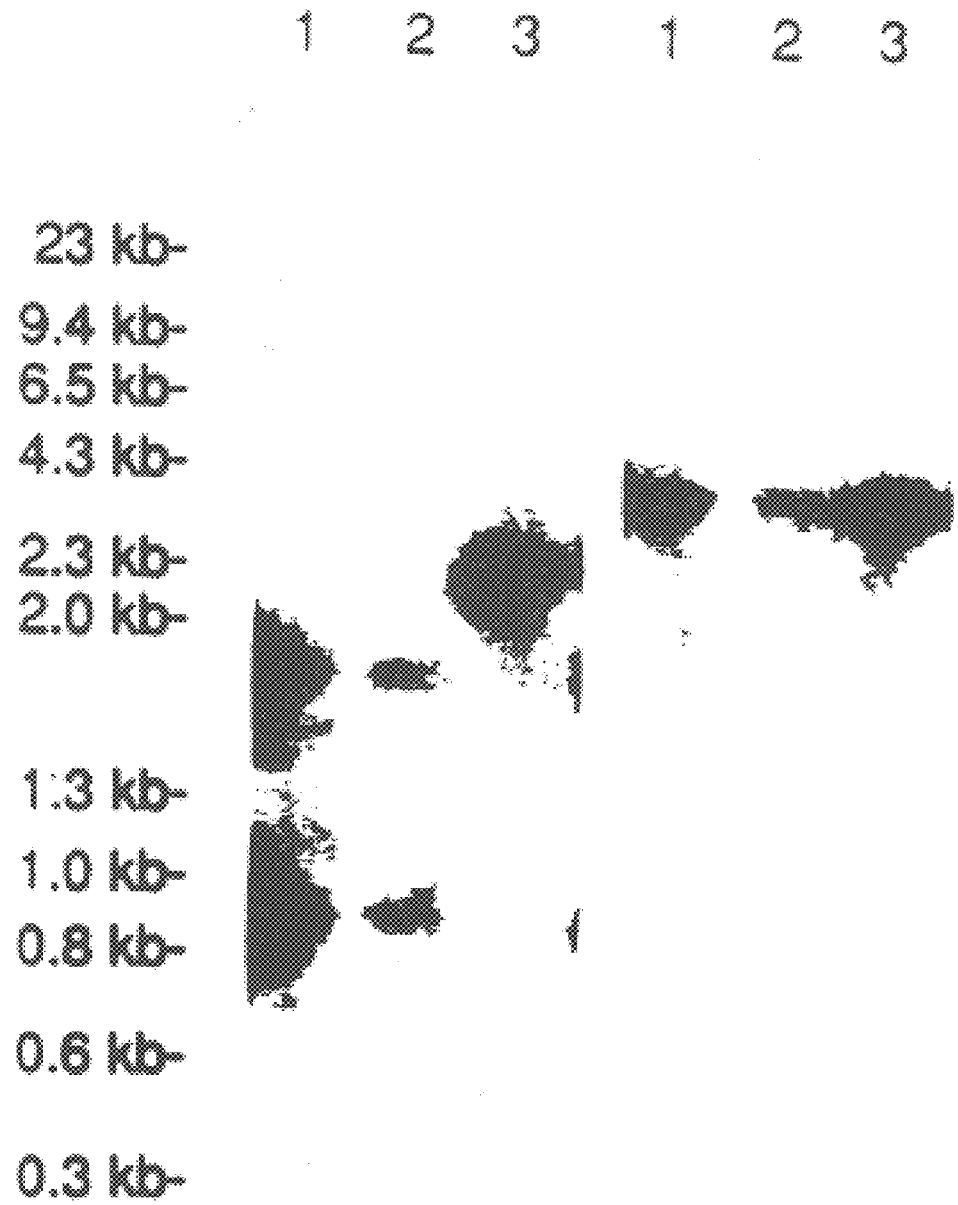
FIG. 5: Southern blot hybridization of KS330Bam and KS627Bam to AIDS-KS genomic DNA extracted from three subjects (lanes 1, 2, and 3) and digested with PvuII. Based on sequence information (FIGS. 3A–3I), restricted sites for Pvu II occur between bp 1504–1505 of the KSHV sequence (FIG. 3A, SEQ ID NO: 1), at bp 134 in KS330Bam (FIG. 3B, SEQ ID NO: 2) and bp 414 in KS627Bam (FIG. 3C, SEQ ID NO: 3). KS330Bam and KS627Bam failed to hybridize to the same fragments in the digests indicating that the two sequences are separated from each other by one or more intervening Bam HI restriction fragments. Digestion with Pvu II and hybridization to KS330Bam resulted in two distinct banding patterns (lanes 1 and 2 vs. lane 3) suggesting variation between KS samples.
Figure 8:
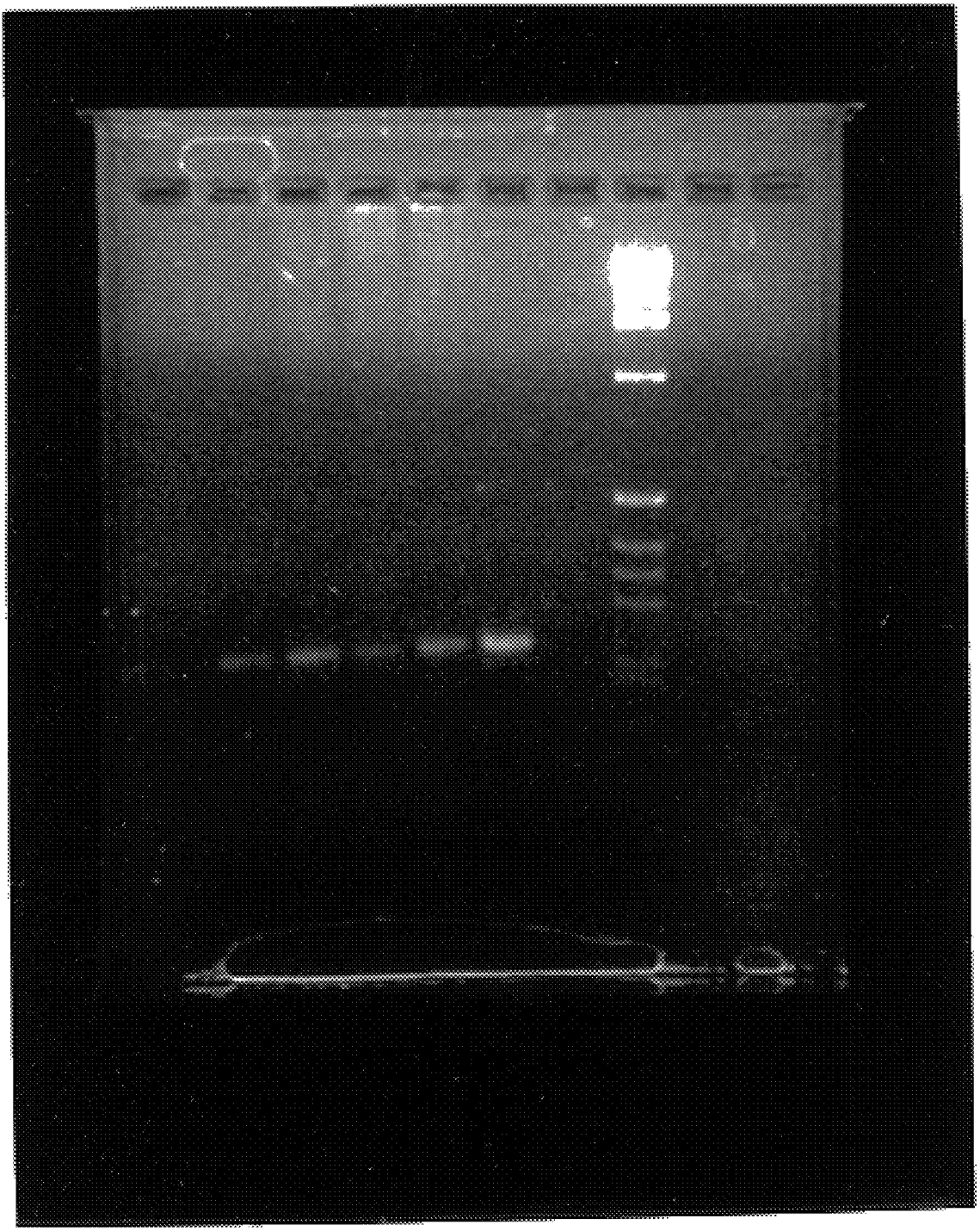
FIG. 8: Subculture of Raji cells co-cultivated with BCBL-1 cells treated with TPA for 2 days. PCR shows that Raji cells are positive for KSHV sequences and indicate that the agent is a transmissible virus.

To determine whether KS330Bam and KS627Bam are portions of a larger genome and to determine the proximity of the two sequences to each other, samples of KS DNA were digested with Pvu II restriction enzymes. Digested genomic DNA from three AIDS-KS samples were hybridized to KS330Bam and KS627Bam by Southern blotting (FIG. 5). These sequences hybridized to various sized fragments of the digested KS DNA indicating that both sequences are fragments of larger genomes. Differences in the KS330Bam hybridization pattern to Pvu II digests of the three AIDS-KS specimens indicate that polymorphisms may occur in the larger genome. Individual fragments from the digests failed to simultaneously hybridize with both KS330Bam and KS627Bam, demonstrating that these two Bam HI restriction fragments are not adjacent to one another.

If KS330Bam and KS627Bam are heritable polymorphic DNA markers for KS, these sequences should be uniformly detected at non-KS tissue sites in patients with AIDS-KS. Alternatively, if KS330Bam and KS627Bam are sequences specific for an exogenous infectious agent, it is likely that some tissues are uninfected and lack detectable KS330Bam and KS627Bam sequences. DNA extracted from multiple uninvolved tissues from three patients with AIDS-KS were hybridized to $^{32}P$-labelled KS330Bam and KS627Bam probes as well as analyzed by PCR using the $KS330_{234}$ primers (Table 2). While KS lesion DNA samples were positive for both bands, unaffected tissues were frequently negative for these sequences. KS lesions from patients A, B and C, and uninvolved skin and muscle from patient A were positive for KS330Bam and KS627Bam, but muscle and brain tissue from patient B and muscle, brain, colon, heart and hilar lymph node tissues from patient C were negative for these sequences. Uninvolved stomach lining adjacent to the KS lesion in patient C was positive by PCR, but negative by Southern blotting which suggests the presence of the sequences in this tissue at levels below the detection threshold for Southern blotting.

TABLE 2

Differential detection of KS330Bam, KS627Bam and $KS330_{234}$ sequences in KS-involved and non-involved tissues from three patients with AIDS-KS.

|  | KS330Bam | KS627Bam | $KS330_{234}$ |
| --- | --- | --- | --- |
| Patient A |  |  |  |
| KS, skin | + | + | + |
| nl skin | + | + | + |
| nl muscle | + | + | + |
| Patient B |  |  |  |
| KS, skin | + | + | + |
| nl muscle | − | − | − |
| nl brain | − | − | − |
| Patient C |  |  |  |
| KS, stomach | + | + | + |
| nl stomach adjacent to KS | − | − | + |
| nl muscle | − | − | − |
| nl brain | − | − | − |
| nl colon | − | − | − |
| nl heart | − | − | − |
| nl hilar lymph nodes | − | − | − |

Experiment 4: Subcloning and sequencing of KSHV

KS330Bam and KS627Bam are genomic fragments of a novel infectious agent associated with AIDS-KS. A genomic library from a KS lesion was made and a phage clone with a 20 kb insert containing the KS330Bam sequence was identified. The 20 kb clone digested with PvuII (which cuts in the middle of the KS330Bam sequence) produced 1.1 kb and 3 kb fragments that hybridized to KS330Bam. The 1.1 kb subcloned insert and ~900 bp from the 3 kb subcloned insert resulting in 9404 bp of contiguous sequence was entirely sequenced. This sequence contains partial and complete open reading frames homologous to regions in gamma herpesviruses.

The KS330Bam sequence is an internal portion of an 918 bp ORF with 55–56% nucleotide identity to the ORF26 and BDLF1 genes of HSVSA and EBV respectively. The EBV and HSVSA translated amino acid sequences for these ORFs demonstrate extensive homology with the amino acid sequence encoded by the KS-associated 918 bp ORF (FIG. 6). In HSVSA, the VP23 protein is a late structural protein involved in capsid construction. Reverse transcriptase (RT)-PCR of mRNA from a KS lesion is positive for transcribed KS330Bam mRNA and that indicates that this ORF is transcribed in KS lesions. Additional evidence for homology between the KS agent and herpesviruses comes from a comparison of the genomic organization of other potential ORFs on the 9404 bp sequence (FIG. 3A) The 5' terminus of the sequence is composed nucleotides having 66–67% nucleotide identity and 68–71% amino acid identity to corresponding regions of the major capsid protein (MCP) ORFs for both EBV and HSVSA. This putative MCP ORF of the KS agent lies immediately 5' to the BDLF1/ORF26 homolog which is a conserved orientation among herpesvirus subfamilies for these two genes. At the 3' end of this sequence, the reading frame has strong amino acid and nucleotide homology to HSVSA ORF 27. Thus, KS-associated DNA sequences at four loci in two separate regions with homologies to gamma herpesviral genomes have been identified.

Figure 9:
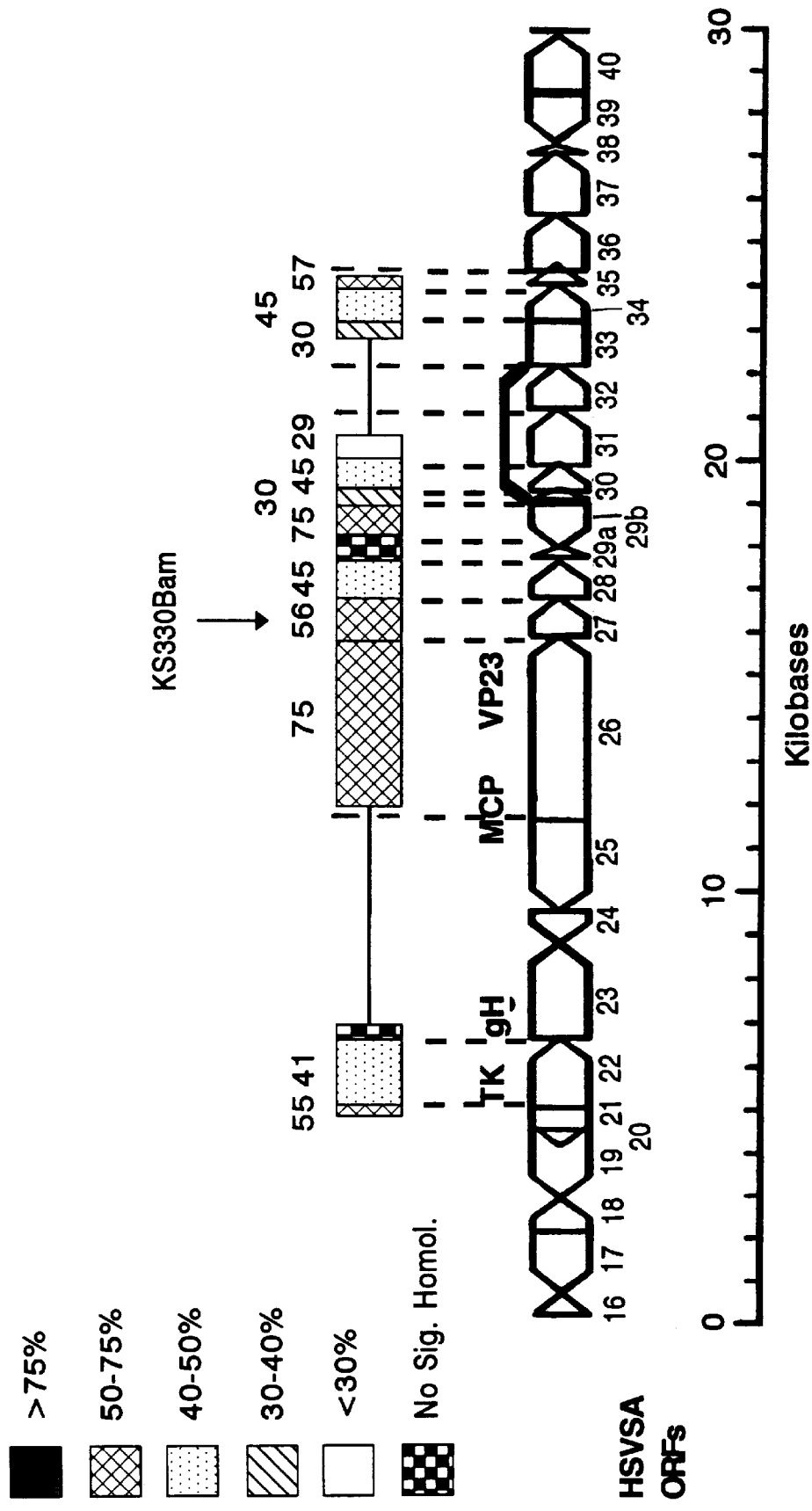
FIG. 9: Map of the KSHV 20 kb sequence and a PvuII digest of the KS330Bam region are shown. Numbers (e.g. 5F) refer to sequenced fragment termini. For the BamHI/NotI digest, fragments have been aligned based on homology of sequenced terminal regions to EBV and HSVSA. Homologies were determined by BLASTX search. In all cases where homologies to gamma herpesviruses were found, highest homologies were to either EBV or HSVSA with the exception of 4R which has highest homology to the gamma herpesvirus bovine herpesvirus 4. All homologies shown have poisson p values $<10^{-6}$ but in no case have identical sequences to known herpesviruses been found.

In addition to fragments obtained from Pvu II digest of the 20 kg phae insert described above, fragments obtained from a BamHI/NotI digest were also subcloned into pBluescript (Stratagene, La Jolla, Calif.). The termini of these subcloned fragments were sequenced and were also found to be homologous to nucleic acid sequence EBV and HSVSA genes. These homologs have been used to develope a preliminary map of subcloned fragments (FIG. 9). Thus, sequencing has revealed that the KS agent maintains co-linear homology to gamma herpesviruses over the length of the 20 kg phage insert.

Experiment 5: Determination of the phylogeny of KSHV

Regions flanking KS330Bam were sequenced and characterized by directional walking. This was performed by the following strategy: 1) KS genomic libraries were made and screened using the KS330Bam fragment as a hybridization probe, 2) DNA inserts from phage clones positive for the KS330Bam probe were isolated and digested with suitable restriction enzyme(s), 3) the digested fragments were subcloned into pBluescript (Stratagene, La Jolla, Calif.), and 4) the subclones were sequenced. Using this strategy, the major capsid protein (MCP) ORF homolog was the first important gene locus identified. Using sequenced unique 3' and 5' end-fragments from positive phage clones as probes, and following the strategy above a KS genomic library are screened by standard methods for additional contiguous sequences.

For sequencing purposes, restriction fragments are subcloned into phagemid pbluescript KS+, pbluescript KS−, pBS+, or pBS31 (Stratagene) or into plasmid pUC18 or pUC19. Recombinant DNA was purified through CsCl density gradients or by anion-exchange chromatography (Qiagen).

Nucleotide sequenced by standard screening methods of cloned fragments of KSHV were done by direct sequencing of double-stranded DNA using oligonucleotide primers synthesized commercially to "walk" along the fragments by the dideoxy-nucleotide chain termination method. Junctions between clones are confirmed by sequencing overlapping clones.

Targeted homologous genes in regions flanking KS330Bam include, but are not limited to: Il-10 homolog, thymidine kinase (TK), gp85, gp35, and MCP. TK is an early protein of the herpesviruses functionally linked to DNA replication and a target enzyme for anti-herpesviral nucleosides. TK phosphorylates acyclic nucleosides such as acyclovir which in turn inhibit viral DNA polymerase chain extension. Determining the sequence of this gene will aid in the prediction of chemotherapeutic agents useful against KSHV. TK is encoded by the EBV BXLF1 ORF located ~9700 bp rightward of BDLF1 and by the HSVSA ORF 21 ~9200 bp rightward of the ORF 26. A subcloned fragment of KS5 was identified with strong homology to the EBV and HSVSA TK open reading frames (FIG. 3F, SEQ ID NO: 6).

gp85 is a late glycoprotein involved in membrane fusion homologous to gH in HSV1. In EBV, this protein is encoded by BLXF2 ORF located ~7600 bp rightward of BDLF1, and in HSVSA it is encoded by ORF 22 located ~7100 bp rightward of ORF26.

gp35 is a late EBV glycoprotein found in virion and plasma membrane. It is encoded by BDLF3 ORF which is 1300 bp leftward of BDLF1 in EBV. There is no BDLF3 homolog in HSVSA. A subcloned fragment has already been identified with strong homology to the EBV gp35 open reading frame.

Major capsid protein (MCP) is a conserved 150 KDa protein which is the major component of herpesvirus capsid. Antibodies are generated against the MCP during natural infection with most herpesviruses. The terminal 1026 bp of this major capsid gene homolog in KSHV have been sequenced.

Targeted homologous genes/loci in regions flanking KS627Bam include, but are not limited to: terminal reiterated repeats, LMPI, EBERs and Ori P. Terminal reiterated sequences are present in all herpesviruses. In EBV, tandomly reiterated 0.5 Kb long terminal repeats flank the ends of the linear genome and become joined in the circular form. The terminal repeat region is immediately adjacent to BNRF1 in EBV and ORF 75 in HSVSA. Since the number of terminal repeats varies between viral strains, identification of terminal repeat regions may allow typing and clonality studies of KSHV in KS legions. Sequencing through the terminal repeat region may determine whether this virus is integrated into human genome in KS.

LMPI is an latent protein important in the transforming effects of EBV in Burkitt's lymphoma. This gene is encoded by the EBV BNRF1 ORF located ~2000 bp rightward of tegument protein ORF BNRF1 in the circularized genome. There is no LMP1 homolog in HSVSA.

EBERs are the most abundant RNA in latently EBV infected cells and Ori-P is the origin of replication for latent EBV genome. This region is located between ~4000–9000 bp leftward of the BNRF1 ORF in EBV; there are no corresponding regions in HSVSA.

The data indicates that the KS agent is a new human herpesvirus related to gamma herpesviruses EBV and HSVSA. The results are not due to contamination or to incidental co-infection with a known herpesvirus since the sequences are distinct from all sequenced herpesviral genomes (including EBV, CMV, HHV6 and HSVSA) and are associated specifically with KS in three separate comparative studies. Furthermore, PCR testing of KS DNA with primers specific for EBV-1 and EBV-2 failed to demonstrate these viral genomes in these tissues. Although KSHV is homologous to EBV regions, the sequence does not match any other known sequence and thus provides evidence for a new viral genome, related to but distinct from known members of the herpesvirus family.

Experiment 6: Serological studies

Indirect immunofluorescence assay (IFA)

Virus-containing cells are coated to a microscope slide. The slides are treated with organic fixatives, dried and then incubated with patient sera. Antibodies in the sera bind to the cells, and then excess nonspecific antibodies are washed off. An antihuman immunoglobulin linked to a fluorochrome, such as fluorescein, is then incubated with the slides, and then excess fluorescent immunoglobulin is washed off. The slides are then examined under a microscope and if the cells fluoresce, then this indicates that the sera contains antibodies directed against the antigens present in the cells, such as the virus.

An indirect immunofluorescence assay (IFA) was performed on the Body Cavity-Based Lymphoma cell line (BCBL-1), which is a naturally transformed EBV infected (nonproducing) B cell line, using 4 KS patient sera and 4 control sera (from AIDS patients without KS). Initially, both sets of sera showed similar levels of antibody binding. To remove nonspecific antibodies directed against EBV and lymphocyte antigens, sera at 1:25 dilution were pre-adsorbed using $3 \times 10^6$ 1% parafomaldehyde-fixed Raji cells per ml of sera. BCBL1 cells were fixed with ethanol/acetone, incubated with dilutions of patient sera, washed and incubated with fluoroscein-conjugated goat anti-human IgG. Indirect immunofluorescent staining was determined.

Table 3 shows that unabsorbed case and control sera have similar end-point dilution indirect immunofluorescence assay (IFA) titers against the BCBL1 cell line. After Raji adsorption, case sera have four-fold higher IFA titers against BCBL1 cells than control sera. Results indicated that pre-adsorption against paraformaldehyde-fixed Raji cells reduces fluorescent antibody binding in control sera but do not eliminate antibody binding to KS case sera. These results indicate that subjects with KS have specific antibodies directed against the KS agent that can be detected in serological assays such as IFA, Western blot and Enzyme immunoassays (Table 3).

TABLE 3

Indirect immunofluorescence end-point titers for KS case and non-KS control sera against the BCBL-1 cell line

| Sera No. | Status* | Pre-adsorption | Post-adsorption** |
|---|---|---|---|
| 1 | KS | ≧1:400 | ≧1:400 |
| 2 | KS | 1:100 | 1:100 |
| 3 | KS | 1:200 | 1:100 |
| 4 | KS | ≧1:400 | 1:200 |
| 5 | Control | ≧1:400 | 1:50 |
| 6 | Control | 1:50 | 1:50 |
| 7 | Control | 1:100 | 1:50 |
| 8 | Control | 1:200 | 1:50 |

Legend Table 3:
*KS = autopsy-confirmed male, AIDS patient Control = autopsy-confirmed female, AIDS patient, no KS
**Adsorbed against RAJI cells treated with 1% paraformaldehyde Immunoblotting ("western blot")

Virus-containing cells or purified virus (or a portion of the virus, such as a fusion protein) is electrophoresed on a polyacrylamide gel to separate the protein antigens by molecular weight. The proteins are blotted onto a nitrocellulose or nylon membrane, then the membrane is incubated in patient sera. Antibodies directed against specific antigens are developed by incubating with a anti-human immunoglobulin attached to a reporter enzyme, such as a peroxidase. After developing the membrane, each antigen reacting against antibodies in patient sera shows up as a band on the membrane at the corresponding molecular weight region.

Enzyme immunoassay ("EIA or ELISA")

Virus-containing cells or purified virus (or a portion of the virus, such as a fusion protein) is coated to the bottom of a 96-well plate by various means (generally incubating in alkaline carbonate buffer). The plates are washed, then the wells are incubated with patient sera. Antibodies in the sera directed against specific antigens stick on the plate. The wells are washed again to remove nonspecific antibody, then they are incubated with a antihuman immunoglobulin attached to a reporter enzyme, such as a peroxidase. The plate is washed again to remove nonspecific antibody and then developed. Wells containing antigen that is specifically recognized by antibodies in the patients sera change color and can be detected by an ELISA plate reader (a spectrophotomer).

All three of these methods can be made more specific by pre-incubating patient sera with uninfected cells to adsorb out cross-reacting antibodies against the cells or against other viruses that may be present in the cell line, such as EBV. Cross-reacting antibodies can potentially give a falsely positive test result (i.e. the patient is actually not infected with the virus but has a positive test result because of cross-reacting antibodies directed against cell antigens in the preparation). The importance of the infection experiments with Raji is that if Raji cells, or another well-defined cell line, can be infected, then the patient's sera can be pre-adsorbed against the uninfected parental cell line and then tested in one of the assays. The only antibodies left in the sera after pre-adsorbtion that bind to antigens in the preparation should be directed against the virus.

Experiment 7: Transmission studies

Co-infection experiments

BCBL1 cells were co-cultivated with Raji cell lines separated by a 0.45 μ tissue filter insert. Approximately, $1-2 \times 10^6$ BCBL1 and $2 \times 10^6$ Raji cells were co-cultivated for 2–20 days in supplemented RPMI alone, in 10 μg/ml 5'-bromodeoxyuridine (BUdR) and 0.6 μg/ml 5'-flourodeoxyuridine or 20 ng/ml 12-O-tetradecanoylphorbol-13-acetate (TPA). After 2,8,12 or 20 days co-cultivation, Raji cells were removed, washed and placed in supplemented RPMI 1640 media. A Raji culture co-cultivated with BCBL1 in 20 ng/ml TPA for 2 days survived and has been kept in continuous suspension culture for >10 weeks. This cell line, designated RCC1 (Raji Co-Culture, No. 1) remains PCR positive for the $KS330_{234}$ sequence after multiple passages. This cell line is identical to its parental Raji cell line by flow cytometry using EMA, B1, B4 and BerH2 lymphocyte-flow cytometry (approximately 2%). RCC1 periodically undergo rapid cytolysis suggestive of lytic reproduction of the agent. Thus, RCC1 is a Raji cell line newly infected with KSHV.

The results indicate the presence of a new human virus, specifically a herpesvirus in KS lesions. The high degree of association between this agent and AIDS-KS (>90%), and the low prevalence of the agent in non-KS tissues from immunocompromised AIDS patients, indicates that this agent has a causal role in AIDS-KS [47, 68].

Experiment 8: Purification of KSHV

DNA is extracted using standard techniques from the RCC-1 or $RCC-1_{2F5}$ cell line [27, 49, 66]. The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at >1×10$^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortilized cells die during course of prolonged cultivation.

Further, the virus may be propagated in a new cell line by removing media supernatant containing the virus from a continuously infected cell line at a concentration of >1×10$^6$ cells/ml. The media is centrifuged at 2000 xg for 10 minutes and filtered through a 0.45 $\mu$ filter to remove cells. The media is applied in a 1:1 volume with cells growing at >1×10$^6$ cells/ml for 48 hours. The cells are washed and pelleted and placed in fresh culture medium, and tested after 14 days of growth.

The herpesvirus may be isolated from the cell DNA in the following manner. An infected cell line, which can be lysed using standard methods such as hyposmotic shocking and Dounce homogenization, is first pelleted at 2000 xg for 10 minutes, the supernatant is removed and centrifuged again at 10,000 xg for 15 minutes to remove nuclei and organelles. The supernatant is filtered through a 0.45 $\mu$ filter and centrifuged again at 100,000 xg for 1 hour to pellet the virus. The virus can then be washed and centrifuged again at 100,000 xg for 1 hour.

REFERENCES:

1. Ablashi, D. V., et al. *Virology* 184:545–552.
2. Albrecht, J. C., et al. (1992) *J. Virol.* 66:5047.
3. Altshul, S. F., et al. (1990) *J. Molec. Biol.* 215:403.
4. *Analytical Biochemistry* (1984) 238:267–284.
5. Andrei, et al. (1992) *Eur. J. Clin. Microbiol. Infect. Dis.* 11(2):143–51.
6. Archibald, C. P., et al. (1992) *Epidemiol.* 3:203.
7. Asada, H., et al (1989) *J. Clin. Microbiol.* 27(10):2204.
8. Ausubel, F., et al. (1987) *Current Protocols in Molecular Biology,* New York.
9. Baer, R. J., et al. (1984) *Nature* 310:207.
10. Bagasra, et al. (1992) *J. New England Journal of Medicine* 326(21):1385–1391.
11. Balzarini, et al. (1990) *Mol. Pharm.* 37,402–7.
12. *Basic and Clinical Immunology* 7th Edition D. Stites and A. Terr ed.
13. Beral, V., et al. (1990) *Lancet* 335:123.
14. Beral, V., et al. (1991) *Brit. Med. J.* 302:624.
15. Beral, V., et al. (1992) *Lancet* 339:632.
16. Bendsoe, N., et al. (1990) *Eur. J. Cancer* 26:699.
17. Biggar, R. J., et al. (1994) *Am. J. Epidemiol.* 139:362.
18. Bovenzi, P., et al. (1993) *Lancet* 341:1288.
19. Beaucage and Carruthers (1981) *Tetrahedron Lett.* 22:1859–1862.
20. Braitman, et al. (1991) *Antimicrob. Agents and Chemotherapy* 35(7):1464–8.
21. Burns and Sanford, (1990) *J. Infect. Dis.* 162(3) :634–7.
22. De Clercq, (1993) *Antimicrobial Chemotherapy* 32, Suppl. A, 121–132.
23. Drew, W. L., et al. (1982) *Lancet* ii:125.
24. Falk, et al. (1991) *Nature* 351:290.
25. Gaidano, G., et al. (1991) *Proc. Natl. Acad. Sci. USA* 88:5413.
26. Gershon, A. A., (1992) *J. Inf. Des.* 166(Suppl):563.
27. Glick, J. L., (1980) *Fundamentals of Human Lymphoid Culture,* Marcel Dokker, New York.
28. Gorbach, S. L., et al. (1992) *Infectious Disease* Ch.35:289, W. B. Saunders, Philadelphia, Pa.
29. Greenspan, et al. (1990) *J. Acquir. Immune Defic. Syndr.* 3 (6):571.
30. Hardy, I., et al. (1990) *Inf. Dis. Clin. N. Amer.* 4(1):159.
31. Hardy, I., et al. (1991) *New Engl. J. Med.* 325 (22):1545.
31A. Harel-Bellan, A., et al. (1988) *Exp. Med.* 168:2309–2318
32. Harlow and Lane, (1988) *Antibodies, A Laboratory Manual,* Cold Spring Harbor Publication, New York.
33. Haverkos, H. W., et al. (1985) *Sexually Transm. Dis.* 12:203.
34. Helene, C. and Toulme, J. (1990) *Biochim. Biophys. Acta.* 1049:99–125.
35. Heniford, et al. (1993) *Nucleic Acids Research* 21(14):3159–3166.
36. Higashi, K., et al. (1989) *J. Clin. Micro.* 27(10):2204.
37. Holmberg, S. D., et al. (1990) *Cancer Detection and Prevention* 14:331.
38. Holliday, J., and Williams, M. V., (1992) *Antimicrob. Agents Chemother.* 36(9):1935.
39. Hoogenboom, H. R., et al. (1991) *Nuc. Acids Res.* 19:4133.
40. Hunt, et al. (1991) *Eur. J. Immunol.* 21:2963–2970.
41. *Hybridization of Nucleic Acids Immobilized on Solid Supports* Meinkoth, J. and Wahl, G.
42. *Hybridization with Nucleic Acid Probes* pp. 495–524, (1993) Elsevier, Amsterdam.
43. Ickes, et al. (1994) *Antiviral Research* 23, Seventh International Conf. on Antiviral Research, Abstract No. 122, Supp. 1.
44. Jahan, N., et al. (1989) *AIDS Research and Human Retroviruses* 5:225.
45. Jardetzkey, et al. (1991) *Nature* 353:326.
46. Johnston, G. S., et al. (1990) *Cancer Detection and Prevention* 14:337.
47. Jung, J. U., et al. (1991) *Proc. Natl. Acad. Sci. USA* 88:7051.
48. Kikuta, et al. (1989) *Lancet* Oct. 7:861.
49. Knowles, D. M., et al. (1989) *Blood* 73:792–798.
50. Kohler and Milstein, (1976) *Eur. J. Immunol.* 6:511–519.
51. Kucera, et al. (1993) *AIDS Res. Human Retroviruses* 9:307–314.
52. *Laboratory Techniques in Biochemistry and Molecular Biology* (1978) North Holland Publishing Company, New York.
53. Lasky, L. A., (1990) *J. Med. Virol.* 31(1):59.
54. Levin, M. J., et al. (1992) *J. Inf. Dis.* 166(2):253.
55. Lifson, A. R., et al. (1990) *Am. J. Epidemiol.* 131:221.
56. Lin, et al. (1991) *Antimicrob Agents Chemother* 35(11):2440–3.
57. Lin, J. C., et al. (1993) *Blood* 81:3372.
58. Lisitsyn, N., et al. (1993) *Science* 259:946.
59. Lo, S -C., et al. (1992) *Internat. J. Systematic Bacteriol.* 42:357.
60. Marks, J. D., et al. (1991) *J. Mol Biol.* 222:581–597.
61. Marloes, et al. (1991) *Eur. J. Immunol.* 21:2963–2970.
62. Matteucci, et al. (1981) *Am. Chem. Soc.* 103:3185.
63. Maxam, A. M. and Gilbert, W. *Methods in Enzymology* (1980) Grossman, L. and Moldave, D., eds., Academic Press, New York, 65:499–560.
64. McCafferty, J., et al. (1990) *Nature* 348:552.
65. Means and Feeney, (1990) *Bioconjugate Chem.* A recent reveiw of protein modification techniques, 1:2–12.
66. Metcalf, D. (1984) *Clonal Culture of Hematopoeitic Cells:Techniques and Applications,* Elvier, New York.

67. *Methods in Enzymology* Vol. 152, (1987) Berger, S. and Kimmel, A. ed., Academic Press, New York
68. Miller, G., *Virology* (1990) B. N. Fields, D. M. Knipe eds., Raven Press, New York, 2:1921.
69. Needham-VanDevanter, D. R., et al., (1984) *Nucelic Acids Res.* 12:6159–6168.
70. Needleman and Wunsch, (1970) *J. Mol. Biol.* 48:443.
71. Neuvo, et al. (1993) *American Journal of Surgical Pathology* 17(7), 683–690.
72. *Nucleic Acid Hybridization: A Practical Approach* (1985) Ed. Hames, B. D. and Higgins, S. J., IRL Press.
73. Oren and Soble, (1991) *Clinical Infectious Diseases* 14:741–6.
74. *PCR Protocols: A Guide to Methods and Applications.* (1990) Innis, M., Gelfand D., Sninsky, J. and White, T., eds., Academic Press, San Diego.
75. Pearson and Lipman, (1988) *Proc. Natl. Acad. Sci. (USA)* 85:2444.
75A. Pearson, J. D., and Regnier, F. E., (1983) *J. Chrom.* 255:137–14976.
76. Pellici, P. G., et al. (1985) *J. Exp. Med.* 162:1015.
77. Peterman, T. A., et al. (1991) Cancer Surveys *Imperial Cancer Research Fund, London,* 10:23–37.
78. Roizman, B. (1991) *Rev. Inf. Disease* 13 Suppl. 11:S892.
79. Rötzschke and Falk, (1991) *Immunol. Today* 12:447.
80. Safai, B., et al. (1980) *Cancer* 45:1472.
81. Sambrook, et al. (1989) *Molecular Cloning: A Laboratory Manual* (2nd ed.), Cold Spring Harbor Laboratory, Vols. 1–3.
82. Saunders, et al. (1990) *J. Acquir. Immune Defic. Syndr.* 3 (6):571.
83. Schecter, M. T., et al. (1991) *Am. J. Epidemiol.* 134:485.
84. Scopes, R., (1982) *Protein Purification: Principles and Practice* Springer-Verlag, N.Y.
85. Siddiqui, A., et al. (1983) *Proc. Natl. Acad. Sci. USA* 80:4861.
86. Skinner, G. R., et al. (1991) *Comp. Immuno. Microbiol. Inf. Dis.* 14(2):13.
87. Skinner, G. R., et al. (1992) *Med. Microbiol. Immunol.* 180(6):305. Smith and Waterman (1981) *Adv. Appl. Math.* 2:482.
88. Snoeck, et al. (1992) *Eur. J. Clin. Micro. Infect. Dis.* 11(12):1144–55.
89. Stals, et al. (1993) *Antimicrobial Agents Chemother.* 37(2):218–23.
90. van den Berg, F. et al. (1989) *J. Clin. Pathol.* 42:128.
91. Vogel, J., et al. (1988) *Nature* 335:606.
92. Wang, R. H. -Y., et al. (1993) *Clin. Infect. Dis.* 17:724.
93. Wickstrom, E. L., et al. (1988) *PNAS (USA)* 85:1028–1032.
94. Winkelmann, et al. (1988) *Drug Res.* 38, 1545–48.
95. Winkler, et al. (1990) *Antiviral Research* 14:61–74.
96. Yamandaka, et al. (1991) *Mol. Pharmacol.* 40(3):446.

---

What is claimed is:

1. A method of diagnosing Kaposi's sarcoma associated herpesvirus infection of a subject which comprises (a) obtaining a suitable sample from the subject, (b) contacting the suitable sample to a Kaposi's sarcoma associated herpesvirus antigen, so as to bind Kaposi's sarcoma associated herpesvirus antibody to a specific Kaposi's sarcoma associated herpesvirus antigen, (c) determining the level of Kaposi's sarcoma associated herpesvirus antibody bound to the Kaposi's sarcoma associated herpesvirus antigen, thereby diagnosing Kaposi's sarcoma associated herpesvirus infection of the subject.

2. The method of claim 1, wherein the Kaposi's sarcoma associated herpesvirus antigen is bound to a support.

3. The method of claim 2, wherein the unbound sample is removed.

4. The method of claim 3, wherein the suitable sample is serum, plasma, cerebrospinal fluid, lymphocytes, urine, transudates, exudates, bone marrow cells, or supernatant from a cell culture.

5. The method of claim 4, wherein the level of antibody bound by the antigen is determined by an immunoassay.

6. The method of claim 5, wherein the immunoassay is ELISA.

7. The method of claim 5, wherein the immunoassay is IFA.

8. The method of claim 5, wherein the immunoassay is Western blotting.

9. The method of claim 1 to diagnose a subject with Kaposi's sarcoma.

10. A kit for diagnosing Kaposi's sarcoma associated herpesvirus infection comprising a Kaposi's sarcoma associated herpesvirus antigen.

11. The kit of claim 10, further comprising a means for determining the level of antibody bound by the Kaposi' sarcoma associated herpesvirus antigen.

12. The kit of claim 11, wherein the Kaposi' sarcoma associated herpesvirus antigen is bound to a support.

13. A method of diagnosing Kaposi's sarcoma associated herpesvirus infection of a subject which comprises (a) obtaining a suitable sample from the subject, (b) contacting the suitable sample to a Kaposi's sarcoma associated herpesvirus antibody, so as to bind Kaposi's sarcoma associated herpesvirus antigen to a specific Kaposi's sarcoma associated herpesvirus antibody, (c) determining the level of Kaposi's sarcoma associated herpesvirus antigen bound to the Kaposi's sarcoma associated herpesvirus antibody, thereby diagnosing Kaposi's sarcoma associated herpesvirus infection of the subject.

14. The method of claim 13, wherein the Kaposi's sarcoma associated herpesvirus antibody is bound to a support.

15. The method of claim 14, wherein the unbound sample is removed.

16. The method of claim 15, wherein the suitable sample is serum, plasma, cerebrospinal fluid, lymphocytes, urine, transudates, exudates, bone marrow cells, or supernatant from a cell culture.

17. The method of claim 16, wherein the level of antigen bound by the antibody is determined by an immunoassay.

18. The method of claim 17, wherein the immunoassay is ELISA.

19. The method of claim 17, wherein the immunoassay is IFA.

20. The method of claim 17, wherein the immunoassay is Western blotting.

21. The method of claim 13 to diagnose a subject with Kaposi's sarcoma.

22. A kit for diagnosing Kaposi's sarcoma associated herpesvirus infection comprising a Kaposi's sarcoma associated herpesvirus antibody.

23. The kit of claim 22, further comprising a means for determining the level of antigen bound by the Kaposi' sarcoma associated herpesvirus antibody.

24. The kit of claim 23, wherein the Kaposi' sarcoma associated herpesvirus antibody is bound to a support.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 9404 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:1:

```
GAGCGCTGCC ATGGAGGCGA CCTTGGAGCA ACGACCTTTC CCGTACCTCG CCACGGAGGC         60

CAACCTCCTA ACGCAGATTA AGGAGTCGGC TGCCGACGGA CTCTTCAAGA GCTTTCAGCT        120

ATTGCTCGGC AAGGACGCCA GAGAAGGCAG TGTCCGTTTC GAAGCGCTAC TGGGCGTATA        180

TACCAATGTG GTGGAGTTTG TTAAGTTTCT GGAGACCGCC CTCGCCGCCG CTTGCGTCAA        240

TACCGAGTTC AAGGACCTGC GGAGAATGAT AGATGGAAAA ATACAGTTTA AAATTTCAAT        300

GCCCACTATT GCCCACGGAG ACGGGAGGAG GCCCAACAAG CAGAGACAGT ATATCGTCAT        360

GAAGGCTTGC AATAAGCACC ACATCGGTGC GGAGATTGAG CTTGCGGCCG CAGACATCGA        420

GCTTCTCTTC GCCGAGAAAG AGACGCCCTT GGACTTCACA GAGTACGCGG GTGCCATCAA        480

GACGATTACG TCGCTTTGC AGTTTGGTAT GGACGCCCTA GAACGGGGC TAGTGGACAC          540

GGTTCTCGCA GTTAAACTTC GGCACGCTCC ACCCGTCTTT ATTTTAAAGA CGCTGGGCA        600

TCCCGTCTAC TCTGAGAGGG GCCTCAAAAA GTGCGTCAAG TCTGACATGG TATCCATGTT        660
```

-continued

```
CAAGGCACAC CTCATAAACA TTCATTTTTT TCTAGATAAG GCCGAGCTCA TGACAAGGGG      720

GAAGCAGTAT GTCCTAACCA TGCTCTCCGA CATGCTGGCC GCGGTGTGCG AGGATACCGT      780

CTTTAAGGGT GTCAGCACGT ACACCACGGC CTCTGGGCAG CAGGTGGCCG GCGTCCTGGA      840

GACGACGGAC AGCGTCATGA GACGGCTGAT GAACCTGCTG GGGCAAGTGG AAAGTGCCAT      900

GTCCGGGCCC GCGGCCTACG CCAGCTACGT TGTCAGGGGT GCCAACCTCG TCACCGCCGT      960

TAGCTACGGA AGGGCGATGA GAAACTTTGA ACAGTTTATG GCACGCATAG TGGACCATCC     1020

AACGTCTGCG TCTGTGGAAG GTGACAAGGC CGCTCTCCGG AGACACGACG AGATTCAGAG     1080

AACCCGCATC GCCGCCTCTC TCGTCAAGAT AGGGGATAAG TTTGTGGCCA TTGAAAGTTT     1140

GCAGCGCATG TACAACGAGA CTCAGTTTCC CTGCCCACTG AACCGGCGCA TCCAGTACAC     1200

CTATTTCTTC CCTGTTGGCC TTCACCTTCC CGTGCCCCGC TACTCGACAT CCGTCTCAGT     1260

CAGGGGCGTA GAATCCCCGG CCATCCAGTC GACCGAGACG TGGGTGGTTA ATAAAAACAA     1320

CGTGCCTCTT TGCTTCGGTT ACCAAAACGC CCTCAAAAGC ATATGCCACC CTCGAATGCA     1380

CAACCCCACC AGTCAGCCGC CGGCACAAAA CCAAGCTTTT CCCGATCCCG ACGGGGACA      1440

TGGGTACGGT CTCAGGTATG AGCAGACGCC AAACATGAAC CTATTCAGAA CGTTCCACCA     1500

GTATTACATG GGGAAAAACG TGGCATTTGT TCCCGATGTG GCCCAAAAAG CGCTCGTAAC     1560

CACGGAGGAT CTACTGCACC CAACCTCTCA CCGTCTCCTC AGATTGGAGG TCCACCCCTT     1620

CTTTGATTTT TTTGTGCACC CCTGTCCTGG AGCGAGAGGA TCGTACCGCG CCACCCACAG     1680

AACAATGGTT GGAAATATAC CACAACCGGT CGCTCCAAGG GAGTTTCAGG AAAGTAGAGG     1740

GGCGCAGTTC GACGCTGTGA CGAATATGAC ACACGTCATA GACCAGCTAA CTATTGACGT     1800

CATACAGGAG ACGGCATTTG ACCCCGCGTA TCCCCTGTTC TGCTATGTAA TCGAAGCAAT     1860

GATTCACGGA CAGGAAGAAA AATTCGTGAT GAACATGCCC CTCATTGCCC TGGTCATTCA     1920

AACCTACTGG GTCAACTCGG GAAAACTGGC GTTTGTGAAC AGTTATCACA TGGTTAGATT     1980

CATCTGTACG CATATGGGGA TTGGAAGCAT CCCTAAGGAG GCGCACGGCC ACTACCGGAA     2040

AATCTTAGGC GAGCTCATCG GCCTTGAGCA GGCGCTTCTC AAGCTCGCGG GACACGAGAC     2100

GGTGGGTCGG ACGCCGATCA CACATCTGGT TTCGGCTCTC CTCGACCCGC ATCTGCTGCC     2160

TCCCTTTGCC TACCACGATG TCTTTACGGA TCTTATGCAG AAGTCATCCA GACAACCCAT     2220

AATCAAGATC GGGGATCAAA ACTACGACAA CCCTCAAAAT AGGGCGACAT TCATCAACCT     2280

CAGGGGTCGC ATGGAGGACC TAGTCAATAA CCTTGTTAAC ATTACCAGA CAAGGGTCAA      2340

TGAGGACCAT GACGAGAGAC ACGTCCTGGA CGTGGCGCCC CTGGACGAGA ATGACTACAA     2400

CCCGGTCCTC GAGAAGCTAT TCTACTATGT TTTAATGCCG GTGTGCAGTA ACGGCCACAT     2460

GTGCGGTATG GGGGTCGACT ATCAAAACGT GGCCCTGACG CTGACTTACA ACGGCCCCGT     2520

CTTTGCGGAC GTCGTGAACG CACAGGATGA TATTCTACTG CACCTGGAGA ACGGAACCTT     2580

GAAGGACATT CTGCAGGCAG GCGACATACG CCGACGGTGG ACATGATCAG GGTGCTGTGC     2640

ACCTCGTTTC TGACGTGCCC TTTCGTCACC CAGGCCGCTC GCGTGATCAC AAAGCGGGAC     2700

CCGGCCCAGA GTTTTGCCAC GCACGAATAC GGGAAGGATG TGGCGCAGAC CGTGCTTGTT     2760

AATGGCTTTG GTGCGTTCGC GGTGGCGGAC CGCTCTGCCG AGGCGGCGGA GACTATGTTT     2820

TATCCGGTAC CCTTTAACAA GCTCTACGCT GACCCGTTGG TGGCTGACAC ACTGCATCCG     2880

CTCCTGCCAA ACTATGTCAC CAGGCTCCCC AACCAGAGAA ACGCGGTGGT CTTTAACGTG     2940

CCATCCAATC TCATGGCAGA ATATGAGGAA TGGCACAAGT CGCCCGTCGC GGCGTATGCC     3000
```

```
GCGTCTTGTC AGGCCACCCC GGGCGCCATT AGCGCCATGG TGAGCATGCA CCAAAAACTA      3060

TCTGCCCCCA GTTTCATTTG CCAGGCAAAA CACCGCATGC ACCCTGGTTT TGCCATGACA      3120

GTCGTCAGGA CGGACGAGGT TCTAGCAGAG CACATCCTAT ACTGCTCCAG GGCGTCGACA      3180

TCCATGTTTG TGGGCTTGCC TTCGGTGGTA CGGCGCGAGG TACGTTCGGA CGCGGTGACT      3240

TTTGAAATTA CCCACGAGAT CGCTTCCCTG CACACCGCAC TTGGCTACTC ATCAGTCATC      3300

GCCCCGGCCC ACGTGGCCGC CATAACTACA GACATGGGAG TACATTGTCA GGACCTCTTT      3360

ATGATTTTCC CAGGGGACGC GTATCAGGAC CGCCAGCTGC ATGACTATAT CAAAATGAAA      3420

GCGGGCGTGC AAACCGGCTC ACCGGGAAAC AGAATGGATC ACGTGGGATA CACTGCTGGG      3480

GTTCCTCGCT GCGAGAACCT GCCCGGTTTG AGTCATGGTC AGCTGGCAAC CTGCGAGATA      3540

ATTCCCACGC CGGTCACATC TGACGTTGCC TATTTCCAGA CCCCCAGCAA CCCCCGGGGG      3600

CGTGCGGCGT CGGTCGTGTC GTGTGATGCT TACAGTAACG AAAGCGCAGA GCGTTTGTTC      3660

TACGACCATT CAATACCAGA CCCCGCGTAC GAATGCCGGT CCACCAACAA CCCGTGGGCT      3720

TCGCAGCGTG GCTCCCTCGG CGACGTGCTA TACAATATCA CCTTTCGCCA GACTGCGCTG      3780

CCGGGCATGT ACAGTCCTTG TCGGCAGTTC TTCCACAAGG AAGACATTAT GCGGTACAAT      3840

AGGGGGTTGT ACACTTTGGT TAATGAGTAT TCTGCCAGGC TTGCTGGGGC CCCCGCCACC      3900

AGCACTACAG ACCTCCAGTA CGTCGTGGTC AACGGTACAG ACGTGTTTTT GGACCAGCCT      3960

TGCCATATGC TGCAGGAGGC CTATCCCACG CTCGCCGCCA GCCACAGAGT TATGCTTGCC      4020

GAGTACATGT CAAACAAGCA GACACACGCC CCAGTACACA TGGGCCAGTA TCTCATTGAA      4080

GAGGTGGCGC CGATGAAGAG ACTATTAAAG CTCGGAAACA AGGTGGTGTA TTAGCTAACC      4140

CTTCTAGCGT TGGCTAGTCA TGGCACTCGA CAAGAGTATA GTGGTTAACT TCACCTCCAG      4200

ACTCTTCGCT GATGAACTGG CCGCCCTTCA GTCAAAAATA GGGAGCGTAC TGCCGCTCGG      4260

AGATTGCCAC CGTTTACAAA ATATACAGGC ATTGGGCCTG GGGTGCGTAT GCTCACGTGA      4320

GACATCTCCG GACTACATCC AAATTATGCA GTATCTATCC AAGTGCACAC TCGCTGTCCT      4380

GGAGGAGGTT CGCCCGGACA GCCTGCGCCT AACGCGGATG GATCCCTCTG ACAACCTTCA      4440

GATAAAAAAC GTATATGCCC CCTTTTTTCA GTGGGACAGC AACACCCAGC TAGCAGTGCT      4500

ACCCCCATTT TTTAGCCGAA AGGATTCCAC CATTGTGCTC GAATCCAACG GATTTGACCC      4560

CGTGTTCCCC ATGGTCGTGC CGCAGCAACT GGGGCACGCT ATTCTGCAGC AGCTGTTGGT      4620

GTACCACATC TACTCCAAAA TATCGGCCGG GGCCCCGGAT GATGTAAATA TGGCGGAACT      4680

TGATCTATAT ACCACCAATG TGTCATTTAT GGGGCGCACA TATCGTCTGG ACGTAGACAA      4740

CACGGATCCA CGTACTGCCC TGCGAGTGCT TGACGATCTG TCCATGTACC TTTGTATCCT      4800

ATCAGCCTTG GTTCCCAGGG GGTGTCTCCG TCTGCTCACG GCGCTCGTGC GGCACGACAG      4860

GCATCCTCTG ACAGAGGTGT TTGAGGGGGT GGTGCCAGAT GAGGTGACCA GGATAGATCT      4920

CGACCAGTTG AGCGTCCCAG ATGACATCAC CAGGATGCGC GTCATGTTCT CCTATCTTCA      4980

GAGTCTCAGT TCTATATTTA ATCTTGGCCC CAGACTGCAC GTGTATGCCT ACTCGGCAGA      5040

GACTTTGGCG GCCTCCTGTT GGTATTCCCC ACGCTAACGA TTTGAAGCGG GGGGGGTATG      5100

GCGTCATCTG ATATTCTGTC GGTTGCAAGG ACGGATGACG GCTCCGTCTG TGAAGTCTCC      5160

CTGCGTGGAG GTAGGAAAAA AACTACCGTC TACCTGCCGG ACACTGAACC CTGGGTGGTA      5220

GAGACCGACG CCATCAAAGA CGCCTTCCTC AGCGACGGGA TCGTGATATG GCTCGAAAGC      5280

TTCATCGTGG TGCCCTGCCC TCAAATTCTC ACAACGGCTT GAGGATGGTG CTTTTTTGTT      5340

ATTGTTACTT GCAAAATTGT GTGTACCTAG CCCTGTTTCT GTGCCCCCTT AATCCTTACT      5400
```

```
TGGTAACTCC CTCAAGCATT GAGTTTGCCG AGCCCGTTGT GGCACCTGAG GTGCTCTTCC    5460

CACACCCGGC TGAGATGTCT CGCGGTTGCG ATGACGCGAT TTTCTGTAAA CTGCCCTATA    5520

CCGTGCCTAT AATCAACACC ACGTTTGGAC GCATTTACCC GAACTCTACA CGCGAGCCGG    5580

ACGGCAGGCC TACGGATTAC TCCATGGCCC TTAGAAGGGC TTTTGCAGTT ATGGTTAACA    5640

CGTCATGTGC AGGAGTGACA TTGTGCCGCG GAGAAACTCA GACCGCATCC CGTAACCACA    5700

CTGAGTGGGA AAATCTGCTG GCTATGTTTT CTGTGATTAT CTATGCCTTA GATCACAACT    5760

GTCACCCGGA AGCACTGTCT ATCGCGAGCG GCATCTTTGA CGAGCGTGAC TATGGATTAT    5820

TCATCTCTCA GCCCCGGAGC GTGCCCTCGC CTACCCCTTG CGACGTGTCG TGGGAAGATA    5880

TCTACAACGG GACTTACCTA GCTCGGCCTG GAAACTGTGA CCCCTGGCCC AATCTATCCA    5940

CCCCTCCCTT GATTCTAAAT TTTAAATAAA GGTGTGTCAC TGGTTACACC ACGATTAAAA    6000

ACCACTCACT GAGATGTCTT TTTAACCGCT AAGGGATTAT ACCGGGATTT AAAACCGCCC    6060

ACTGATTTTT TTACGCTAAG AGTTGGGTGC TTGGGGGGTT TTGCATTGCT CTGTTGTAAA    6120

CTATATATAA GTTAAACCAA AATTCGCAGG GAGACAAGGT GACGGTGGTG AGAACTCAGT    6180

TGAGAGTCAG AGAATACAGT GCTAATCAGG GTAGATGAGC ATGACTTTCC CCGTCTCCAG    6240

TCACCGGAGG AATGGTGGAC GGCTCCGTCC TGGTGCGAAT GGCCACCAAG CCTCCCGTGA    6300

TTGGTCTTAT AACAGTGCTC TTCCTCCTAG TCATAGGCGC CTGCGTCTAC TGCTGCATTC    6360

GCGTGTTCCT GGCGGCTCGA CTGTGGCGCG CCACCCCACT AGGCAGGGCC ACCGTGGCGT    6420

ATCAGGTCCT TCGCACCCTG GGACCGCAGG CCGGGTCACA TGCACCGCCG ACGGTGGGCA    6480

TAGCTACCCA GGAGCCCTAC CGTACAATAT ACATGCCAGA TTAGAACGGG GTGTGTGCTA    6540

TAATGGATGG CTATGGGGGG GGGCTGTAGA TAATTGAGCG CTGTGCTTTT ATTGTGGGGA    6600

TATGGGCTTG TACATGTGTC TATCATCGGT AGCCATAAAA TGGGCCATGA CAACTGCCAC    6660

AAGTAAGTCG TCCGACATGT GCTTTTGCTT GGCGCTGTAT GACTGCCCTC CATCCCTAAG    6720

CGGGACGCAC TTGATCGCGC GGACCTGTTC TACCAGGTAG GTCACCGGGT CAAATGATAT    6780

TTTGATGGTG TTGGACACCA CCGTCTGGCT GGCGCTCAGG GTGCCGGAGT TCAGAGCGTA    6840

GATGAATGTC TCAAACGCGG AGGATTTCTC GCCTCCCAAC ATGTAAATTG GCCACTGCAG    6900

GGCGCTGCTC TTGTCAGTAT AGTGTAGAAA ATGTATGGGG AGCGGGCATA TTTCGTTAAG    6960

GACGGTTGCA ATGGCCACCC CAGAATCTTG GCTGCTGTTG CCTTCGAACG CGGTTCACGC    7020

GCTCAATTGT GGGGTGGAGC ACAGCGATCG CCTTAATCAT CGTGCATCGG CAGGACGCTA    7080

TCTCGTAAGC AGCTGGCCCA GTGAGGTCGC GCAGGAAGAA ATGCTCCATG CCCAATATGA    7140

GGCTTCTGGT GGGAGTCTGA GTACTCGTGA CAACGGCGCC CACCATGTAC CGGACGCCTC    7200

CGTGTTGTTC GTATACGCGG GGTCGATGTA AACAAACAGC TGTTTTCCAA GGCACTTCTG    7260

AACCTGCTGG GCGGTGTGTC TACCCGACAC ATGTCAAACT GTGTCAGCGC TGCGTCACCC    7320

ACCACGCGGT AAAGCGTACG ATTTGACGAC GCTGCTCCCT CGCCCATTAG TTCGGTGTCG    7380

AATGCCCCCT CCATAAAGAG GTTGGTGGTG GTTTTGATGG ATTCGTCGAT GGTGATGTAC    7440

GTCGGAATGT GCAGTCTGTA ACAAGGACAG GACACTAGTG CGTCTTGCAG GTGGAAATCT    7500

TCTCGGTGGT CCGCACACAC GTAACTGACC ACATTCAGCA TCTTTTCCTG GCGTTCCTG    7560

AGGTTAAGCA GGAAACTCGT GGAGCGGTCT GACGAGTTCA CGGATGATAT AAATATAAGC    7620

TTGGCGTCTT TCTGAAGCAT GAAACCCAGA ATAGCCGGCA GTGCATCCTT TTTAATAAAA    7680

TTCGCCTCGT CTACGTAGAG CAGGTTAAAG GTCTGTCCCC GAATGCTCTG CAGACACGGA    7740
```

-continued

```
AAGACACAAA AGAGGGGCTC ATAAGCGGCT AACAGTAAAG GAGAGGAGGC GAACAGTGCG      7800

TGGCTCTTGG TTCTTGGGAA TAAAAGGGGG CGTGTGTGCC GATCGATCGT ATGGGTGAGC      7860

CAGTGGATCC TGGACATGTG GTGAATGAGA AAGATTTTGA GGAGTGTGAA CAATTTTTCA      7920

GTCAACCCCT TAGGGAGCAA GTGGTCGCGG GGGTCAGGGC ACTCGACGGC CTCGGTCTCG      7980

CTGACTCTCT ATGTCACAAA ACAGAAAGAC TCTGCCTGCT GATGGACCTG GTGGGCACGG      8040

AGTGCTTTGC GAGGGTGTGC CGCCTAGACA CCGGTGCGAA ATGAAGAGTG TGGCGAGTCC      8100

CTTATGTCAG TTCCACGGCG TGTTTTGCCT GTACCAGTGT CGCCAGTGCC TGGCATACCA      8160

CGTGTGTGAT GGGGGCGCCG AATGCGTTCT CCTGCATACG CCGGAGAGCG TCATCTGCGA      8220

ACTAACGGGT AACTGCATGC TCGGCAACAT TCAAGAGGGC CAGTTTTTAG GGCCGGTACC      8280

GTATCGGACT TTGGATAACC AGGTTGACAG GGACGCATAT CACGGGATGC TAGCGTGTCT      8340

GAAACGGGAC ATTGTGCGGT ATTTGCAGAC ATGGCCGGAC ACCACCGTAA TCGTGCAGGA      8400

AATAGCCCTG GGGGACGGCG TCACCGACAC CATCTCGGCC ATTATAGATG AAACATTCGG      8460

TGAGTGTCTT CCCGTACTGG GGGAGGCCCA AGGCGGGTAC GCCCTGGTCT GTAGCATGTA      8520

TCTGCACGTT ATCGTCTCCA TCTATTCGAC AAAAACGGTG TACAACAGTA TGCTATTTAA      8580

ATGCACAAAG AATAAAAAGT ACGACTGCAT TGCCAAGCGG GTGCGGACAA AATGGATGCG      8640

CATGCTATCA ACGAAAGATA CGTAGGTCCT CGCTGCCACC GTTTGGCCCA CGTGGTGCTG      8700

CCTAGGACCT TTCTGCTGCA TCACGCCATA CCCCTGGAGC CCGAGATCAT CTTTTCCACC      8760

TACACCCGGT TCAGCCGGTC GCCAGGGTCA TCCCGCCGGT TGGTGGTGTG TGGGAAACGT      8820

GTCCTGCCAG GGGAGGAAAA CCAACTTGCG TCTTCACCTT CTGGTTTGGC GCTTAGCCTG      8880

CCTCTGTTTT CCCACGATGG GAACTTTCAT CCATTTGACA TCTCGGTACT GCGCATTTCC      8940

TGCCCTGGTT CTAATCTTAG TCTTACTGTC AGATTTCTCT ATCTATCTCT GGTGGTGGCT      9000

ATGGGGGCGG GACGGAATAA TGCGCGGAGT CCGACCGTTG ACGGGGTATC GCCGCCAGAG      9060

GGCGCCGTAG CCCACCCTTT GGAGGAACTG CAGAGGCTGG CGCGTGCTAC GCCGGACCCG      9120

GCACTCACCC GTGGACCGTT GCAGGTCCTG ACCGGCCTTC TCCGCGCAGG GTCAGACGGA      9180

GACCGCGCCA CTCACCACAT GGCGCTCGAG GCTCCGGGAA CCGTGCGTGG AGAAAGCCTA      9240

GACCCGNCTG TTTCACAGAA GGGGGCAGCG CGCACACGCC ACAGGCCACC CCCCGTGCGA      9300

CTGAGCTTCA ACCCCGTCAA TGNCGATGTA CCCGCTACCT GGNGAGACGC CACTAACGTG      9360

TACTCGGGTG CTCCCTACTA TGTGTGTGTT TACGAACGCG GTGG                      9404
```

(2) INFORMATION FOR SEQ ID NO:2:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:2:

```
GGATCCCTCT GACAACCTTC AGATAAAAAA CGTATATGCC CCCTTTTTTC AGTGGGACAG        60

CAACACCCAG CTAGCAGTGC TACCCCCATT TTTTAGCCGA AAGGATTCCA CCATTGTGCT       120

CGAATCCAAC GGATTTGACC CCGTGTTCCC CATGGTCGTG CCGCAGCAAC TGGGGCACGC       180
```

```
TATTCTGCAG CAGCTGTTGG TGTACCACAT CTACTCCAAA ATATCGGCCG GGGCCCCGGA    240

TGATGTAAAT ATGGCGGAAC TTGATCTATA TACCACCAAT GTGTCATTTA TGGGGCGCAC    300

ATATCGTCTG GACGTAGACA ACACGGATCC                                    330

(2) INFORMATION FOR SEQ ID NO:3:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:3:

GGATCCGCTG GCAGGTGGGC GCGCACCTCG TCGGGTAGCT TGGAGACAAA CAGCTCCAGG     60

CCAGTCCGCG CCGTAGCGCC TGCAGGTGCC TCACCACCGG GGCCGGGTCA TGCGATCTGT    120

TTAGTCCGGA GAAGATAGGG CCCTTGGGAA GCCGCTGAAC CAGCTCCAGG GTCTCCAAGA    180

TGCGCACCGG TTGTCGGAGC TGTCGCGATA GAGGTTAGGG TAGGTGTCCG GTCCGTCCGT    240

GGGCTCAAAC CTGCCCAGAC ACACCACTGT CTGCTGGGGG ATCATCCTTC TCAGGGAGAT    300

GCATTCTTTG GAAGTAGTGG TAGAGATGGA GCAGACTGCC AGGGCGTTGC AGGAGTGGTG    360

GCGATGGTGC GCACCGTTTT TAAGAAACCC CCCAGGGTGG GGACTCCCGC TCCCTGCAGC    420

ATCTCGGCCT GCTGTACGTC CTTGGCGAAT ATGGACGAA ATCGGCTGTG CGCACGGGGT     480

CCCAGGGCCG GTCCGGTGGC ATACAGGCCG GTGAGGGCCC CCTGGGTCTG TCCGCCTGGA    540

AACAGGGTGC TGTGAAACAA CAGGTTGCAA GGCCGCGAAT ACCCCTCTGC ACGCTGCTGT    600

GGACGTGGGT GTATGCTCCG TGGATCC                                       627

(2) INFORMATION FOR SEQ ID NO:4:

(i) SEQUENCE CHARACTERISTICS:
        (A) LENGTH: 1558 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:4:

CCGCAGCTCT AATACGACTC ACTATAGGGC GTCGACTCGA TCAAATAGCG ATACAGCTGC     60

CCTCCTGTTG ATGTTGGCCT CCAGAGCCGA CTTAATAAAC TCTCTTTTAG AGTTGGTTGA    120

GTCCATTCTC CTTGATCATG GTGATGATCG CCGGTATGTC ATACGATGGG ATGATTAGAT    180

AGTCGCCCGT AGTTGGACAC CTTTGGGTCT GAACATTGCC TGTTATATAC TGGGTCCCTT    240

TTCCACTCAA CAGTAGGATT CCACCCACGT GGTCCCCTGA CCGCAATTAT GCTATTTTGC    300

TGATATATGT GACACAAGAG GCAGGTGTGG GAAATGTAAG TGTCGGAAGC ATCTATGATT    360

TTCATCTGAC TCACTACCCT TTGTATCCGA GAAGTAGCGA ATGGCGGGCG GCAAGCGCCA    420

TGTCCCGGAA AAATCTCCGT ATAGAAACTT GGTGTACTTC AGGGCATGAT TAACGAACGA    480

CAAAAGATCC CGTTTGGAGC GTACATGTGA CCTGGAAGTA GCACCGGGCC CGGGTAACCG    540
```

```
CAGTGCTGTT TGTACAGGCA ACAGTCGGCC CGACAAAAAG AGGCGGGTCC GTTGAACAGC     600

AGCCATAGCA ACGGAAGGGG GTCGTCAGGA AGAAGACCCT TCCAAGTTCC GGGGTCACAC     660

AGGCCATCTA CAGCCTCCCG AAGGAGCGCA TCCTTATTCA GAGTCAAAGC CCACGTCCAC     720

TCCTCGGTAG TATAGTGGTT GTAGAACACC TGGCCCTTTT CGTGTGTTTC TACGTGAGAC     780

GGGTCCAGTG CGATTTCCTC ACCCGCCGCC CCGAAACCCT GCCCGAGGAC TCTCTGGAGC     840

TTCTCCAGTC TAGGCAAGTG GAGATTACTA AAGTCTGGCC GCAAGGCCGG CCGGCCACTG     900

CAGATTGGCT GGACCTCGGG TCATCACGTT GGAAACCAAG AGGAAGCTGT TCAGGGGAGT     960

TTCTATCANC TTAAATTGTC CAGGTGTGTT CTCGGTAAGG TCCAGGGCAA GTTGTNCGCC    1020

CTTGACGTAC CTACTGGTCA CCTCCGGGTC ACCCTCGGAC ACGAGCGAGC TCAAAGCAAA    1080

CATGCTGCTC AGCCGACACA GGGAGCGTCT TGCCGACAAC CTGGAGGAGA CCGACAAAGA    1140

CGGCGGAGAG AGGTGGGAAC TGAGTGCCCC GACATTCACG CGACACTGTC CCAAAACGGC    1200

ACGGATGGCG CACCCTTTTA TTGGNGTGGT GCACAGAATA AACTCATACA GTTCGGTCCT    1260

GGAAACATAC TGCACACGGG ACCATCCCGC CACGCCCACG TCAGCAAATC CCGACGTGGG    1320

AACCCCCAGA CCGTCCGAGG ACAACGTCCC CGCAAAGNCG CGCCTATTGG AGTCCCTATC    1380

AACATACTTG NAGATGCGGT GTGTGCGCGA GGACGCGCAC GTCTCCACGG NCGATCAACT    1440

GGTCGAGTAC CAGGCGGNCA GAAAAACACA CGACTCCCTG CACGCCTGCT CTGTCTACCG    1500

CGAAACTTCA GGCTTTTCTG GTTAACCTTT CGGTCCTTTC TGAACGGGTG TTACGTTC     1558

(2) INFORMATION FOR SEQ ID NO:5:

(i) SEQUENCE CHARACTERISTICS:
        (A) LENGTH: 2973 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:5:

GCGGCCGCGA GCTCAATTAA CCCTCACTAA AGGGAGTCGA CTCGATCGAG TCGGAGAGTT      60

GGCACAGGCC TTGAGCTCGC TGTGACGTTC TCACGGTGTT GGTTGGGATC AGCTGGTGAC     120

TCAGACAAGT CTTGAGCTCT ACAACGTAAC ATACGGGCTG ATGCCCACCC GATACCAGAA     180

TTACGCAGTC GGCAATTCTG TGCCCTAGAG TCACCTCAAA GAATAATCTG TGGTGTCCAA     240

GGGGAGGGTT CTGGGGCCGG CTACTTAGAA ACCGCCATAG ATCGGGCAGG GTGGAGTACT     300

TGAGGAGCCG GCGGTAGGTG GCCAGGTGGG CCGGTTACCT GCTCTTTTGC GTGCTGCTGG     360

AAGCCTGCTC AGGGATTTCT TAACCTCGGC CTCGGTTGGA CGTACCATGG CAGAAGGCGG     420

TTTTGGAGCG GACTCGGTGG GGCGCGGCGG AGAAAAGGCC TCTGTGACTA GGGGAGGCAG     480

GTGGGACTTG GGGAGCTCGG ACGACGAATC AAGCACCTCC ACAACCAGCA CGGATATGGA     540

CGACCTCCCT GAGGAGAGGA AACCACTAAC GGGAAAGTCT GTAAAAACCT CGTACATATA     600

CGACGTGCCC ACCGTCCCGA CCAGCAAGCC GTGGCATTTA ATGCACGACA ACTCCCTCTA     660

CGCAACGCCT AGGTTTCCGC CCAGACCTCT CATACGGCAC CCTTCCGAAA AAGGCAGCAT     720

TTTTGCCAGT CGGTTGTCAG CGACTGACGA CGACTCGGGA GACTACGCGC CAATGGATCG     780

CTTCGCCTTC CAGAGCCCCA GGGTGTGTGG TCGCCCTCCC CTTCCGCCTC CAAATCACCC     840
```

```
ACCTCCGGCA ACTAGGCCGG CAGACGCGTC AATGGGGAC GTGGGCTGGG CGGATCTGCA      900

GGGACTCAAG AGGACCCCAA AGGGATTTTT AAAAACATCT ACCAAGGGGG GCAGTCTCAA      960

AGCCCGTGGA CGCGATGTAG GTGACCGTCT CAGGGACGGC GGCTTTGCCT TTAGTCCTAG     1020

GGGCGTGAAA TCTGCCATAG GGCAAAACAT TAAATCATGG TTGGGATCG GAGAATCATC     1080

GGCGACTGCT GTCCCCGTCA CCACGCAGCT TATGGTACCG GTGCACCTCA TTAGAACGCC     1140

TGTGACCGTG GACTACAGGA ATGTTTATTT GCTTTACTTA GAGGGGGTAA TGGGTGTGGG     1200

CAAATCAACG CTGGTCAACG CCGTGTGCGG GATCTTGCCC CAGGAGAGAG TGACAAGTTT     1260

TCCCGAGCCC ATGGTGTACT GGACGAGGGC ATTTACAGAT TGTTACAAGG AAATTTCCCA     1320

CCTGATGAAG TCTGGTAAGG CGGGAGACCC GCTGACGTCT GCCAAAATAT ACTCATGCCA     1380

AAACAAGTTT TCGCTCCCCT TCCGGACGAA CGCCACCGCT ATCCTGCGAA TGATGCAGCC     1440

CTGGAACGTT GGGGGTGGGT CTGGGAGGGG CACTCACTGG TGCGTCTTTG ATAGGCATCT     1500

CCTCTCCCCA GCAGTGGTGT TCCCTCTCAT GCACCTGAAG CACGGCGCCT ATCTTTTGAT     1560

CACTTCTTTC AATTACTTTC CATCTTTAGA GCCACAGAAG GCGACGTGGT CGCCATTCTC     1620

ACCCTCTCCA GCGCCGAGTC GTTGCGGCGG GTCAGGGCGA GGGGAAGAAA GAACGACGGG     1680

ACGGTGGAGC AAAACTACAT CAGAGAATTG GCGTGGGCTT ATCACGCCGT GTACTGTTCA     1740

TGGATCATGT TGCAGTACAT CACTGTGGAG CAGATGGTAC AACTATGCGT ACAAACCACA     1800

AATATTCCGG AAATCTGCTT CCGCAGCGTG CGCCTGGCAC ACAAGGAGGA AACTTTGAAA     1860

AACCTTCACG AGCAGAGCAT GCTACCTATG ATACACCGGT GTACTGGATC CCGTGAGACA     1920

TCATCCCGTC GTGATCGAGC TTTGCTTTTG TTTCTTCACA GAGCTGAGAA AATTACAATT     1980

TATCGTAGCC GACGCGGATA AGTTCCACGA CGACGTATGC GGCCTGTGGA CCGAAATCTA     2040

CAGGCAGATC CTGTCCAATC CGGCTATTAA ACCCAGGGCC ATCAACTGGC CAGCATTAGA     2100

GAGCCAGTCT AAAGCAGTTA ATCACCTAGA GGAGACATGC AGGGTCTAGC CTTCTTGGCG     2160

GCCCTTGCAT GCTGGCGATG CATATCGTTG ACATGTGGAG CCACTGGCGC GTTGCCGACA     2220

ACGGCGACGA CAATAACCCG CTCCGCCACG CAGCTCATCA ATGGGAGAAC CAACCTCTCC     2280

ATAGAACTGG AATTCAACGG CACTAGTTTT TTTCTAAATT GGCAAAATCT GTTGAATGTG     2340

ATCACGGAGC CGGCCCTGAC AGAGTTGTGG ACCTCCGCCG AAGTCGCCGA GGACCTCAGG     2400

GTAACTCTGA AAAAGAGGCA AAGTCTTTTT TTCCCCAACA AGACAGTTGT GATCTCTGGA     2460

GACGGCCATC GCTATACGTG CGAGGTGCCG ACGTCGTCGC AAACTTATAA CATCACCAAG     2520

GGCTTTTACT ATAGCGCTCT GCCCGGGCAC CTTGGCGGAT TTGGGATCAA CGCGCGTCTG     2580

GTACTGGGTG ATATCTTCGC ATCAAAATGG TCGCTATTCG CGAGGGACAC CCCAGAGTAT     2640

CGGGCGTTTT ACCCAATGAA TGTCATGGCC GTCAAGTTTT CCATATCCAT TGGCAACAAC     2700

GAGTCCGGCG TAGCGCTCTA TGGAGTGGTG TCGGAAGATT TCGTGGTCGT CACGCTCCAC     2760

AACAGGTCCA AAGAGGCTAA CGAGACGGCG TCCCATCTTC TGTTCGGTCT CCCGGATTCA     2820

CTGCCATCTC TGAAGGGCCA TGCCACCTAT GATGAACTCT CGTTCGCCCG AAACGCAAAA     2880

TATGCGCTAG TGGCGATCCT GCCTAAAGAT TCTTACCAGA CACTCCTTAC AGAGAATTGC     2940

ACTCGCATAT TTCTGAACAT GACGGAGTCG ACG                                 2973

(2) INFORMATION FOR SEQ ID NO:6:

(i) SEQUENCE CHARACTERISTICS:
          (A) LENGTH: 1410 base pairs
          (B) TYPE: nucleic acid
```

(C) STRANDEDNESS: single
            (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:6:

| | | | | | |
|---|---|---|---|---|---|
| GAGTCTCTAA | TCCTGAAGTC | CCGATGCCAC | TGTTGTTCGA | AAAGTTTGGG | ACTCCGGACT | 60 |
| CGTCTACCCT | GCCACTCTAC | GCGGCTAGGC | ACCCGGAACT | ATCGTTGCTA | CGGATCATGC | 120 |
| TCTCACCGCA | CCCCTACGCG | TTAAGAAGCC | ACTTGTGCGT | AGGCGAAGAG | ACCGCATCTC | 180 |
| TTGGCGTTTA | CCTGCACTCC | AAGCCAGTCG | TACGCGGCCA | NGAATTCGAG | GACACGCAGA | 240 |
| TACTACCGGA | GTGCCGGCTG | CCATAACGA | GCGACCAGTC | TTATACCAAC | TTTAAGATTA | 300 |
| TAGATCTGCC | AGCGGGATGC | CGTCGCGTCC | CCATACACGC | CGCGAACAAG | CGTGTCGTCA | 360 |
| TCGACGAGGC | CGCCAACCGC | ATAAAGGTGT | TTGACCCAGA | GTCGCCTTTA | CCGCGTCACC | 420 |
| CCATAACACC | CNNTGCCGGT | CAGACCAGAT | CTATACTGAA | ACACAACATC | GCACAGGTTT | 480 |
| GCGAACGGGA | TATCGTGTCA | CTTAACACAG | ACAACGAGGC | CGCGTCTATG | TTCTACATGA | 540 |
| TTGGACTCAG | GCGGCCGAGA | CTCGGAGAAA | GCCCGGTCTG | TGACTTCAAC | ACCGTTACCA | 600 |
| TCATGGAGCG | TGCTAACAAC | TCGATAACTT | TTCTACCCAA | GCTAAAACTG | AACCGGCTAC | 660 |
| AACACCTGTT | CCTGAAGCAC | GTGTTNNTGC | GCAGCATGGG | GCTGGAAAAC | ATCGTGTCGT | 720 |
| GTTTCTCATC | GCTGTACGGC | GCAGAACTTG | CCCCTGCGAA | AACACACGAG | CGGGAGTTCT | 780 |
| TCGGCGCTCT | GCTAGAAAGA | CTCAAACGTC | GGGTGGAGGA | CGCGGTCTTC | TGCCTGAATA | 840 |
| CCATAGAGGA | TTTCCCGTTT | AGGGAACCCA | TTCGCCAACC | CCCAGATTGT | TCCAAGGTGC | 900 |
| TTATAGAAGC | CATGGAAAAG | TACTTTATGA | TGTGTAGCCC | CAAAGACCGT | CAAAGCGCCG | 960 |
| CATGGCTAGG | TGCAGGGGTG | GTCGAACTGA | TATGTGACGG | CAATCCACTT | TCTGAGGTGC | 1020 |
| TCGGATTTCT | TGCCAAGTAT | ATGCCCATAC | AAAAAGAATG | CACAGGAAAC | CTTTTAAAAA | 1080 |
| TCTACGCTTT | ATTGACCGTC | TAATAAAGGA | TGGAAAACAG | TCTGTAAAGA | AAGTAGATAA | 1140 |
| CCCCCGAGAA | CCCAATAAAA | GAGAGAATTA | GAAACAAAGC | ACTGNNTGCG | CGTCTTCTAT | 1200 |
| ACATGCCCCT | TATCTCCACT | ACGGTCCCGT | TGTCCCTCAG | CCACAAATAA | TGAATGTGTA | 1260 |
| GGTTGTTATT | ATCAAAGAAA | GGTGACTTAT | CTAAAAAGAG | GTTGGTCTGC | ACCCTTTCAT | 1320 |
| TAGTGACATA | CATGAGAGAC | TGCAGGCCAT | CGCTCTCGTC | GTAGCTCATG | ATTACAGAGT | 1380 |
| CACAAAGGGG | GCAACCTCTT | CTTGGTGTGC | | | | 1410 |

(2) INFORMATION FOR SEQ ID NO:7:

(i) SEQUENCE CHARACTERISTICS:
        (A) LENGTH: 529 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:7:

| | | | | | |
|---|---|---|---|---|---|
| CTCTTTTGGG | AAAAGCGGGT | CGACGGTACA | GCGGCGAAGG | TTTAATAATT | GACGGTGGCG | 60 |
| GAGTGTTTAC | GCGCGGACAG | ATAGACACCG | ACAACTACCT | ACCTGCGGTG | GGATCATGGG | 120 |

```
AACTTACCGA TGATTGTGAT AAACCCTGCG AATTCAGGGA GCTACGCTCG CTGTATCTTC      180

CCGCGCTACT AACGTGCACC ATATGTTACA AAGCCATGTT CAGGATAGTG TGCAGGTACC      240

TGGAGTTCTG GGAGTTCGAA CAGTGTTTTC ATGCGTTTCT GGCGGTGTTG CCCCATAGTC      300

TACAACCCAC AATCTATCAA AATTATTTTG CACTCCTGGA GAGCCTGAAG CATCTCTCGT      360

TTTCAATAAT GCCACCCGCA TCCCCAGACG CACAGCTACA TTTTTTAAAG TTTAACATCA      420

GCAGCTTCAT GGCCACGTGG GGGTGGCACG GAGAGCTGGT CTCNNTGCGC CGTGCCATCG      480

CTCACAACGT AGAGCGACTG CCCACCGTGC TGAAGAACGC TTATCGATA                 529

(2) INFORMATION FOR SEQ ID NO:8:

(i) SEQUENCE CHARACTERISTICS:
        (A) LENGTH: 1315 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:8:

AAAGTTTAAC ATCAGCAGCT TCATGGCCAC GTGGGGGTGG CACGGAGAGC TGGTCTNNCT       60

GCGCCGTGCC ATCGCTCACA ACGCAGAGCG ACTGCCCACC GTGCTGAAGA ACCTGTCGAA      120

ACAGAGTAAG CACCAGGACG TCAAGGTTAA CGGACGGGAT CTGGTGGGCT TTCAGCTGGC      180

TCTAAACCAG CTCGTGTCCC GTCTGCACGT AAAAATCCAA CGCAAGGACC CCGGACCAAA      240

GCCATACAGG GTGGTCGTCA GTACCCCAGA TTGTACCTAC TATCTAGTGT ATCCGGGCAC      300

ACCGGCCATC TACAGACTCG TCATGTGTAT GGCAGTGGCA GACTGCATCG GCCACTCGTG      360

CAGCGGACTG CACCCCTGCG CAAACTTTTT AGGCACCCAC GAGACACCGC GTCTCCTGGC      420

GGCGACGCTT TCAAGAATCC GGTACGCGCC GAAAGACCGG CGAGCAGCCA TGAAAGGAAA      480

TTTGCAGGCG TGCTTCCAAC GATACGCGGC CACGGACGCG CGGACTCTGG GCAGCTCTAC      540

AGTGTCAGAC ATGCTGGAAC CCACAAAACA CGTCAGTTTG GAAAACTTCA AGATCACCAT      600

ATTCAACACC AACATGGTGA TTAACACTAA GATAAGCTGC CACGTTCCTA ACACCCTGCA      660

AAAGACTATT TTAAACATCC CCAGATTGAC CAACAATTTT GTTATACGAA AGTACTCCGT      720

AAAGGAACCT TCTTTTACCA TAAGCGTGTT TTTTTCCGAC AACATGTGTC AAGGCACCGC      780

AATAAACATC AACATCAGTG GGGACATGCT GCACTTTCTC TTCGCAATGG GTACGCTGAA      840

ATGCTTTCTG CCAATCAGGC ACATATTTCC TGTATCGATA GCAAATTGGA ACTCCACGTT      900

GGACCTGCAC GGACTGGAAA ACCAGTACAT GGTGAGAATG GGGCGAAAAA ACGTATTTTG      960

GACCACAAAC TTTCCATCTG TGGTCTCCAG CAAGGATGGG CTAAACGTGT CCTGGTTTAA     1020

GGCCGCGACA GCCACGATTT CTAAAGTGTA CGGGCAGCCT CTTGTGGAAC AGATTCGCCA     1080

CGANNTGGCG CCCATTCTCA CGGACCAGCA CGCGCGCATC GACGGAAACA AAATAGAAT      1140

ATTCTCCCTA CTTGAGCACA GAAACCGTTC CCAAATACAG ACGCTACACA AAAGGTTCCT     1200

GGAGTGTCTG GTGGAATGCT GTTCGTTTCT CAGGCTTGAC GTGGCTTGCA TTAGGCGAGC     1260

CGCCGCCCGG GGCCTGTTTG ACTTCTCAAA GAAGATAATC AGTCACACTA AAAGC          1315

(2) INFORMATION FOR SEQ ID NO:9:
```

```
    (i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:9:

GCAATGCAAA CTTCATTTCG TTCGTCGCCA CCACGGGTCA TCGGTTCGCC GCTCTAAAGC      60

CACAAATTGT CCGTCACGCC ATTCGCAAAC TAGGCCTGCA CTGGCGCCAC CGAACGGCCG     120

CGTCCAACGA GCAGACACCG CCAGCCGATC CCCGCGTACG TTGCGTCCGT CCGCTGGTCT     180

AAGCTATGTT ACGAGTTCCG GACGTGAAGG CTAGTCTAGT AGAGNNGCGG CGCGCCTGTC     240

GACAGGCGAG CGCGTGTTTC ACGTCTTGAC CTCTCCGGCG GTGGCGRCCA TGGTGGGAG     299

(2) INFORMATION FOR SEQ ID NO:10:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:10:

AGCCGAAAGG ATTCCACCAT TGTGCTCGAA TCCAACGGAT TTGACCCCGT GTTCCCCATG      60

GTCGTGCCGC AGCAACTGGG GCACGCTATT CTGCAGCAGC TGTTGGTGTA CCACATCTAC     120

TCCAAAATAT CGGCCGGGGC CCCGGATGAT GTAAATATGG CGGAACTTGA TCTATATACC     180

ACCAATGTGT CATTTATGGG GCGCACATAT CGTCTGGACG TAGACAACAC GGA            233

(2) INFORMATION FOR SEQ ID NO:11:

(i) SEQUENCE CHARACTERISTICS:
        (A) LENGTH: 328 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:11:

GAAATTACCC ACGAGATCGC TTCCCTGCAC ACCGCACTTG GCTACTCATC AGTCATCGCC      60

CCGGCCCACG TGGCCGCCAT AACTACAGAC ATGGGAGTAC ATTGTCAGGA CCTCTTTATG     120

ATTTTCCCAG GGGACGCGTA TCAGGACCGC CAGCTGCATG ACTATATCAA AATGAAAGCG     180

GGCGTGCAAA CCGGCTCACC GGGAAACAGA ATGGATCACG TGGGATACAC TGCTGGGGTT     240

CCTCGCTGCG AGAACCTGCC CGGTTTGAGT CATGGTCAGC TGGCAACCTG CGAGATAATT     300

CCCACGCCGG TCACATCTGA CGTTGCCT                                        328
```

(2) INFORMATION FOR SEQ ID NO:12:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:12:

AACACGTCAT GTGCAGGAGT GACATTGTGC CGCGGAGAAA CTCAGACCGC ATCCCGTAAC        60

CACACTGAGT GGGAAAATCT GCTGGCTATG TTTTCTGTGA TTATCTATGC CTTAGATCAC       120

AACTGTCACC CG                                                          132

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:13:

AGCCGAAAGG ATTCCACCAT TCCGTGTTGT CTACGTCCAG                              40

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:14:

GAAATTACCC ACGAGATCGC AGGCAACGTC AGATGTGA                                38

(2) INFORMATION FOR SEQ ID NO:15:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:15:

AACACGTCAT GTGCAGGAGT GACCGGGTGA CAGTTGTGAT CTAAGG                       46

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:16:

ACAGGGCTGG TTGCCCAGGG T                                      21

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:17:

AGTTGCAAAC CAGACCTCAG                                       20

(2) INFORMATION FOR SEQ ID NO:18:

(i) SEQUENCE CHARACTERISTICS:
        (A) LENGTH: 861 amino acids
        (B) TYPE: amino acid
        (C) STRANDEDNESS: single
        (D) TOPOLOGY: linear (ii) MOLECULE TYPE: peptide (iii) HYPOTHETICAL: N (iv) ANTI-SENSE: N (ix) FEATURE:
        (A) NAME/KEY: Peptide
        (B) LOCATION: 1..861
        (D) OTHER INFORMATION:

(xi) SEQUENCE DESCRIPTION: SEQ ID NO:18:

```
Leu Glu Gln Arg Pro Phe Pro Tyr Leu Ala Thr Glu Ala Asn Leu Leu
 1               5                  10                  15

Thr Gln Ile Lys Glu Ser Ala Ala Asp Gly Leu Phe Lys Ser Phe Gln
                20                  25                  30

Leu Leu Leu Gly Lys Asp Ala Arg Glu Gly Ser Val Arg Phe Glu Ala
                35                  40                  45

Leu Leu Gly Val Tyr Thr Asn Val Val Glu Phe Val Lys Phe Leu Glu
        50                  55                  60

Thr Ala Leu Ala Ala Ala Cys Val Asn Thr Glu Phe Lys Asp Leu Arg
65                  70                  75                  80

Arg Met Asp Gly Lys Ile Gln Phe Lys Ile Ser Met Pro Thr Ile Ala
                85                  90                  95

His Gly Asp Gly Arg Arg Pro Asn Lys Gln Arg Gln Tyr Ile Val Met
```

-continued

```
                100                 105                 110
Lys Ala Cys Asn Lys His His Ile Gly Ala Glu Ile Glu Leu Ala Ala
            115                 120                 125
Ala Asp Ile Glu Leu Leu Phe Ala Glu Lys Glu Thr Pro Leu Asp Phe
130                 135                 140
Thr Glu Tyr Ala Gly Ala Ile Lys Thr Ile Thr Gly Ala Leu Gln Phe
145                 150                 155                 160
Gly Met Asp Ala Leu Glu Arg Cys Leu Val Asp Thr Val Leu Ala Val
            165                 170                 175
Lys Leu Arg His Ala Pro Pro Val Phe Ile Leu Lys Thr Leu Gly His
            180                 185                 190
Pro Val Tyr Ser Glu Arg Gly Leu Lys Lys Cys Val Lys Ser Asp Met
            195                 200                 205
Val Ser Met Phe Lys Ala His Leu Ile Asn Ile His Phe Phe Leu Asp
            210                 215                 220
Lys Ala Glu Leu Met Thr Arg Gly Lys Gln Tyr Val Leu Thr Met Leu
225                 230                 235                 240
Ser Asp Met Leu Ala Ala Val Cys Glu Asp Thr Val Phe Lys Gly Val
            245                 250                 255
Ser Thr Tyr Thr Thr Ala Ser Gly Gln Gln Val Ala Gly Val Leu Glu
            260                 265                 270
Thr Thr Asp Ser Val Met Arg Arg Leu Met Asn Leu Leu Gly Gln Val
            275                 280                 285
Glu Ser Ala Met Ser Gly Pro Ala Ala Tyr Ala Ser Tyr Val Val Arg
            290                 295                 300
Gly Ala Asn Leu Val Thr Ala Val Ser Tyr Gly Arg Ala Met Arg Asn
305                 310                 315                 320
Phe Glu Gln Phe Met Ala Arg Ile Val Asp His Pro Thr Ser Ala Ser
            325                 330                 335
Val Glu Gly Asp Lys Ala Ala Leu Arg Arg His Asp Glu Gln Arg Thr
            340                 345                 350
Arg Ile Ala Ala Ser Leu Val Lys Ile Gly Asp Lys Phe Val Ala Ile
            355                 360                 365
Glu Ser Leu Gln Arg Met Tyr Asn Glu Thr Gln Phe Pro Cys Pro Leu
            370                 375                 380
Asn Arg Arg Ile Gln Tyr Thr Tyr Phe Phe Pro Val Gly Leu His Leu
385                 390                 395                 400
Pro Val Pro Arg Tyr Ser Thr Ser Val Ser Val Arg Gly Val Glu Ser
            405                 410                 415
Pro Ala Ile Gln Ser Thr Glu Thr Trp Val Val Asn Lys Asn Asn Val
            420                 425                 430
Pro Leu Cys Phe Gly Tyr Gln Asn Ala Leu Lys Ser Ile Cys His Pro
            435                 440                 445
Arg Met His Asn Pro Thr Ser Gln Pro Ala Gln Asn Gln Ala Phe
            450                 455                 460
Pro Asp Pro Asp Gly Gly His Gly Tyr Gly Leu Arg Tyr Glu Gln Thr
465                 470                 475                 480
Pro Asn Met Asn Leu Phe Arg Thr Phe His Gln Tyr Tyr Met Gly Lys
            485                 490                 495
Asn Val Ala Phe Val Pro Asp Val Ala Gln Lys Ala Leu Val Thr Thr
            500                 505                 510
Glu Asp Leu Leu His Pro Thr Ser His Arg Leu Leu Arg Leu Glu Val
            515                 520                 525
```

His Pro Phe Phe Asp Phe Phe Val His Pro Cys Pro Gly Ala Arg Gly
    530                 535                 540

Ser Tyr Arg Ala Thr His Arg Thr Met Val Gln Asn Ile Pro Gln Pro
545                 550                 555                 560

Val Ala Pro Arg Glu Phe Gln Glu Ser Arg Gly Ala Gln Phe Asp Ala
                565                 570                 575

Val Thr Asn Met Thr His Val Ile Asp Gln Leu Thr Ile Asp Val Ile
                580                 585                 590

Gln Glu Thr Ala Phe Asp Pro Ala Tyr Pro Leu Phe Cys Tyr Val Ile
    595                 600                 605

Glu Ala Met Ile His Gly Gln Glu Glu Lys Phe Val Met Asn Met Pro
610                 615                 620

Leu Ile Ala Leu Val Ile Gln Thr Tyr Trp Val Asn Ser Gly Lys Leu
625                 630                 635                 640

Ala Phe Val Asn Gly Tyr His Met Val Arg Phe Ile Cys Thr His Met
                645                 650                 655

Gly Ile Gly Ser Ile Pro Lys Glu Ala His Gly His Tyr Arg Lys Ile
                660                 665                 670

Leu Gly Glu Leu Ile Gly Leu Glu Gln Ala Leu Leu Lys Leu Ala Gly
    675                 680                 685

His Glu Thr Val Gly Arg Thr Pro Ile Thr His Leu Val Ser Ala Leu
    690                 695                 700

Leu Asp Pro His Leu Leu Pro Pro Phe Ala Tyr His Asp Val Phe Thr
705                 710                 715                 720

Asp Leu Met Gln Lys Ser Ser Arg Gln Pro Ile Ile Lys Ile Gly Asp
                725                 730                 735

Gln Asn Tyr Asp Asn Pro Gln Asn Arg Ala Thr Phe Ile Asn Leu Arg
                740                 745                 750

Gly Arg Met Glu Asp Leu Val Asn Asn Leu Val Asn Ile Tyr Gln Thr
                755                 760                 765

Arg Val Asn Glu Asp His Asp Glu Arg His Val Leu Asp Val Ala Pro
    770                 775                 780

Leu Asp Glu Asn Asp Tyr Asn Pro Val Leu Glu Lys Leu Phe Tyr Tyr
785                 790                 795                 800

Val Leu Met Pro Val Cys Ser Asn Gly His Met Cys Gly Met Gly Val
                805                 810                 815

Asp Tyr Gln Asn Val Ala Leu Thr Leu Thr Tyr Asn Gly Pro Val Phe
                820                 825                 830

Ala Asp Val Val Asn Ala Gln Asp Asp Ile Leu Leu His Leu Glu Asn
    835                 840                 845

Gly Thr Leu Lys Asp Ile Leu Gln Ala Gly Asp Ile Arg
850                 855                 860

(2) INFORMATION FOR SEQ ID NO:19:

(i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: peptide (iii) HYPOTHETICAL: N (iv) ANTI-SENSE: N (ix) FEATURE:
    (A) NAME/KEY: Peptide
    (B) LOCATION: 1..272
    (D) OTHER INFORMATION:

(xi) SEQUENCE DESCRIPTION: SEQ ID NO:19:

```
Pro Thr Val Asp Met Ile Arg Val Leu Cys Thr Ser Phe Leu Thr Cys
1               5                   10                  15

Pro Phe Val Thr Gln Ala Ala Arg Val Ile Thr Lys Arg Asp Pro Ala
            20                  25                  30

Gln Ser Phe Ala Thr His Glu Tyr Gly Lys Asp Val Ala Gln Thr Val
        35                  40                  45

Leu Val Asn Gly Phe Gly Ala Phe Ala Val Ala Asp Arg Ser Ala Glu
    50                  55                  60

Ala Ala Glu Thr Met Phe Tyr Pro Val Pro Phe Asn Lys Leu Tyr Ala
65              70                  75                  80

Asp Pro Leu Val Ala Asp Thr Leu His Pro Leu Leu Pro Asn Tyr Val
            85                  90                  95

Thr Arg Leu Pro Asn Gln Arg Asn Ala Val Val Phe Asn Val Pro Ser
        100                 105                 110

Asn Leu Met Ala Glu Tyr Glu Glu Trp His Lys Ser Pro Val Ala Ala
    115                 120                 125

Tyr Ala Ala Ser Cys Gln Ala Thr Pro Gly Ala Ile Ser Ala Met Val
130                 135                 140

Ser Met His Gln Lys Leu Ser Ala Pro Ser Phe Ile Cys Gln Ala Lys
145                 150                 155                 160

His Arg Met His Pro Gly Phe Ala Met Thr Val Val Arg Thr Asp Glu
                165                 170                 175

Val Leu Ala Glu His Ile Leu Tyr Cys Ser Arg Ala Ser Thr Ser Met
            180                 185                 190

Phe Val Gly Leu Pro Ser Val Val Arg Arg Glu Val Arg Ser Asp Ala
        195                 200                 205

Val Thr Phe Glu Ile Thr His Glu Ile Ala Ser Leu His Thr Ala Leu
    210                 215                 220

Gly Tyr Ser Ser Val Ile Ala Pro Ala His Val Ala Ala Ile Thr Thr
225                 230                 235                 240

Asp Met Gly Val His Cys Gln Asp Leu Phe Met Ile Phe Pro Gly Asp
                245                 250                 255

Ala Tyr Gln Asp Arg Gln Leu His Asp Tyr Ile Lys Met Lys Ala Gly
            260                 265                 270
```

(2) INFORMATION FOR SEQ ID NO:20:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: peptide (iii) HYPOTHETICAL: N (iv) ANTI-SENSE: N (ix) FEATURE:
    (A) NAME/KEY: Peptide
    (B) LOCATION: 1..218
    (D) OTHER INFORMATION:

(xi) SEQUENCE DESCRIPTION: SEQ ID NO:20:

```
Gly Val Pro Arg Cys Glu Asn Leu Pro Gly Leu Ser His Gly Gln Leu
1               5                   10                  15

Ala Thr Cys Glu Ile Leu Pro Thr Pro Val Thr Ser Asp Val Ala Tyr
            20                  25                  30

Phe Gln Thr Pro Ser Asn Pro Arg Gly Arg Ala Ala Ser Val Val Ser
        35                  40                  45

Cys Asp Ala Tyr Ser Asn Glu Ser Ala Glu Arg Leu Phe Tyr Asp His
50                  55                  60

Ser Ile Pro Asp Pro Ala Tyr Glu Cys Arg Ser Thr Asn Asn Pro Trp
65                  70                  75                  80

Ala Ser Gln Arg Gly Ser Leu Gly Asp Val Leu Tyr Asn Ile Thr Phe
            85                  90                  95

Arg Gln Thr Ala Leu Pro Gly Met Tyr Ser Pro Cys Arg Gln Phe Phe
            100                 105                 110

His Lys Glu Asp Ile Met Arg Tyr Asn Arg Gly Leu Tyr Thr Leu Val
        115                 120                 125

Asn Glu Tyr Ser Ala Arg Leu Ala Gly Ala Pro Ala Thr Ser Thr Thr
130                 135                 140

Asp Leu Gln Tyr Val Val Asn Gly Thr Asp Val Phe Leu Asp Gln
145                 150                 155                 160

Pro Cys His Met Leu Gln Glu Ala Tyr Pro Thr Leu Ala Ala Ser His
                165                 170                 175

Arg Val Met Leu Ala Glu Tyr Met Ser Asn Lys Gln Thr His Ala Pro
            180                 185                 190

Val His Met Gly Gln Tyr Leu Ile Glu Glu Val Ala Pro Met Lys Arg
        195                 200                 205

Leu Leu Lys Leu Gly Asn Lys Val Val Tyr
210                 215

(2) INFORMATION FOR SEQ ID NO: 21:

(i) SEQUENCE CHARACTERISTICS:
        (A) LENGTH: 304 amino acids
        (B) TYPE: amino acid
        (C) TOPOLOGY: linear (ii) MOLECULE TYPE: protein (xi) SEQUENCE DESCRIPTION: SEQ ID NO: 21:

Met Leu Thr Asp Lys Thr Ile Ile Val Ser Leu Thr Ser Arg Leu Phe
1               5                   10                  15

Ala Asp Glu Ile Thr Lys Leu Gln Lys Lys Ile Gly Ser Ile Leu Pro
            20                  25                  30

Leu Gln Asp Pro His Lys Leu Gln Ser Leu Asp Thr Leu Gly Leu Asn
        35                  40                  45

Ala Val Cys Ser Arg Asp Val Phe Pro Asp Tyr Val His Met Phe Ser
50                  55                  60

Tyr Leu Ser Lys Cys Thr Leu Ala Ile Leu Glu Glu Val Asn Pro Asp
65                  70                  75                  80

Asn Leu Ile Leu Thr Arg Leu Asp Pro Ser Glu Thr Tyr Gln Ile Lys
            85                  90                  95

Asn Val Tyr Glu Pro Met Phe Gln Trp Asp Gly Phe Ser Asn Leu Thr
            100                 105                 110

Val Ile Pro Pro Val Phe Gly Arg Gln Gln Ala Thr Val Thr Leu Glu
        115                 120                 125
```

```
Ser Asn Gly Phe Asp Leu Val Phe Pro Ser Val Val     Pro Ser Asp Leu
    130                 135                 140

Ala Gln Ala Ile Ile Gly Lys Leu Leu Leu Tyr Asn Leu Tyr Ser Arg
145                 150                 155                 160

Leu Val Glu Ser Asp Pro Glu Ile Asn Ile Glu Val Asn Met Tyr
                165                 170                 175

Thr Thr Asn Val Thr His Met Gly Arg His Tyr Val Leu Asp Ile Asn
                180                 185                 190

His Asn Asn Pro Asn Glu Ala Leu Lys Ser Leu Asp Asp Leu Ala Val
                195                 200                 205

Tyr Thr Lys Ile Leu Ser Ala Leu Ile Pro Arg Ala Lys Leu Arg Val
210                 215                 220

Leu Thr Ile Leu Met Arg His Asp Gln His Glu Leu Leu Asp Val Phe
225                 230                 235                 240

Arg Gly Ile Val Pro Arg Glu Val Tyr Glu Ile Asp Ala Asn Ala Leu
                245                 250                 255

Ser Ile Gly Asp Asp Ile Thr Arg Met Thr Thr Phe Ile Thr Tyr Leu
                260                 265                 270

Gln Ser Leu Ser Ser Ile Phe Asn Leu Gly Ala Lys Leu His Leu Ser
    275                 280                 285

Ser Tyr Ala Ser Glu Thr Gln Thr Ala Thr Cys Trp Ile Ser Tyr Cys
    290                 295                 300

(2) INFORMATION FOR SEQ ID NO: 22:

(i) SEQUENCE CHARACTERISTICS:
        (A) LENGTH: 301 amino acids
        (B) TYPE: amino acid
        (C) TOPOLOGY: linear (ii) MOLECULE TYPE: protein (xi) SEQUENCE DESCRIPTION: SEQ ID NO: 22:

Met Asp Leu Lys Val Val Ser Leu Ser Ser Arg Leu Tyr Thr Asp
1               5                   10                  15

Glu Ile Ala Lys Met Gln Gln Arg Ile Gly Cys Ile Leu Pro Leu Ala
                20                  25                  30

Ser Thr His Gly Thr Gln Asn Val Gln Gly Leu Gly Leu Gly Gln Val
            35                  40                  45

Tyr Ser Leu Glu Thr Val Pro Asp Tyr Val Ser Met Tyr Asn Tyr Leu
50                  55                  60

Ser Asp Cys Thr Leu Ala Val Leu Asp Glu Val Ser Val Asp Ser Leu
65                  70                  75                  80

Ile Leu Thr Lys Ile Val Pro Gly Gln Thr Tyr Ala Ile Lys Asn Lys
                85                  90                  95

Tyr Gln Pro Phe Phe Gln Trp His Gly Thr Gly Ser Lys Ser Val Met
                100                 105                 110

Pro Pro Val Phe Gly Arg Glu His Ala Thr Val Lys Leu Glu Ser Asn
            115                 120                 125

Asp Val Asp Ile Val Phe Pro Met Val Leu Pro Thr Pro Ile Ala Glu
    130                 135                 140

Glu Val Leu Gln Lys Ile Leu Leu Phe Asn Val Tyr Ser Arg Val Val
145                 150                 155                 160

Met Gln Ala Pro Gly Asn Ala Asp Met Leu Asp Val His Met His Leu
                165                 170                 175

Gly Ser Val Ser Tyr Leu Gly His His Tyr Glu Leu Ala Leu Pro Glu
```

-continued

```
                180                 185                 190
Val Pro Gly Pro Leu Gly Leu Ala Leu Leu Asp Asn Leu Ser Leu Tyr
            195                 200                 205
Phe Cys Ile Met Val Thr Leu Leu Pro Arg Ala Ser Met Arg Leu Val
    210                 215                 220
Arg Gly Leu Ile Arg His Glu His His Asp Leu Leu Asn Leu Phe Gln
225                 230                 235                 240
Glu Met Val Pro Asp Glu Ile Ala Arg Ile Arg Leu Asp Asp Leu Ser
                245                 250                 255
Val Ala Asp Asp Leu Ser Arg Met Arg Val Met Met Thr Tyr Leu Gln
            260                 265                 270
Ser Leu Ala Ser Leu Phe  Asn Leu Gly Pro Arg Leu Ala Thr Ala Ala
            275                 280                 285
Tyr Ser Gln Glu Thr Leu Thr Ala Thr Cys Trp Leu Arg
    290                 295                 300
```